(12) United States Patent
Yang et al.

(10) Patent No.: US 11,866,452 B2
(45) Date of Patent: Jan. 9, 2024

(54) BIPHENYL COMPOUND AS IMMUNOMODULATOR, PREPARATION METHOD THEREFOR AND APPLICATION THEREOF

(71) Applicant: SHENZHEN CHIPSCREEN BIOSCIENCES CO., LTD., Guangdong (CN)

(72) Inventors: Qianjiao Yang, Guangdong (CN); Song Shan, Guangdong (CN); Lijun Xin, Guangdong (CN); Desi Pan, Guangdong (CN); Xiaoliang Wang, Guangdong (CN); Yonglian Song, Guangdong (CN); Yu Zhang, Guangdong (CN); Huiyun Huang, Guangdong (CN); Qi Wei, Guangdong (CN); Zhibin Li, Guangdong (CN); Xianping Lu, Guangdong (CN)

(73) Assignee: Shenzhen Chipscreen Biosciences Co., Ltd., Guangdong (CN)

( * ) Notice: Subject to any disclaimer, the term of this patent is extended or adjusted under 35 U.S.C. 154(b) by 0 days.

(21) Appl. No.: 18/029,869

(22) PCT Filed: Oct. 28, 2021

(86) PCT No.: PCT/CN2021/126917
§ 371 (c)(1),
(2) Date: Mar. 31, 2023

(87) PCT Pub. No.: WO2022/089511
PCT Pub. Date: May 5, 2022

(65) Prior Publication Data
US 2023/0365590 A1 Nov. 16, 2023

(30) Foreign Application Priority Data
Oct. 29, 2020 (CN) .......................... 202011178102.4

(51) Int. Cl.
*C07D 519/00* (2006.01)
*A61P 37/02* (2006.01)

(52) U.S. Cl.
CPC ............ *C07D 519/00* (2013.01); *A61P 37/02* (2018.01)

(58) Field of Classification Search
CPC ................................ C07D 519/00; A61P 37/02
See application file for complete search history.

(56) References Cited

FOREIGN PATENT DOCUMENTS

| CN | 110267953 | | 9/2019 |
|----|-----------|---|--------|
| CN | 110267953 | A | 9/2019 |
| CN | 111039942 | | 4/2020 |
| CN | 111039942 | A | 4/2020 |
| CN | 114698376 | B | 10/2022 |
| WO | 2018119224 | A1 | 6/2018 |
| WO | 2019217821 | A1 | 11/2019 |
| WO | WO 2019/217821 | | 11/2019 |
| WO | WO-2019217821 | A1 * | 11/2019 ........... A61K 31/437 |

* cited by examiner

*Primary Examiner* — Michael Barker
*Assistant Examiner* — Jed A Kucharczk
(74) *Attorney, Agent, or Firm* — Haley Guiliano LLP

(57) ABSTRACT

A biphenyl compound represented by formula (I), a preparation method therefor and an application thereof. The present invention also relates to a pharmaceutical composition that comprises the compound as an active ingredient. The compound is a novel small molecule immunomodulator having excellent oral absorption features and can be used for treating and/or preventing various immunity-related diseases.

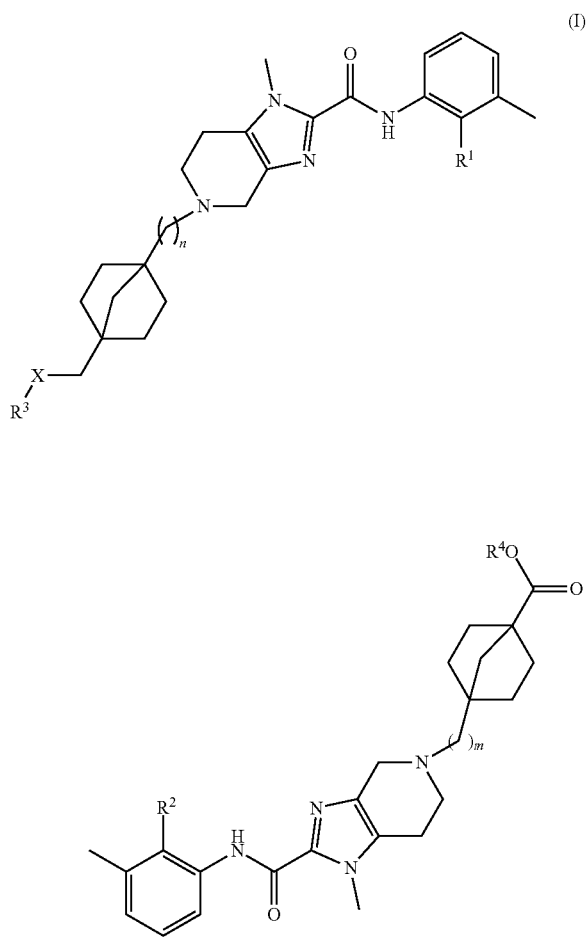

2 Claims, 2 Drawing Sheets

Tissue distribution of Compound I-6 in hPD1/hPD-L1 mice on Day 16 of administration (100 mg/kg, PO)

Tissue distribution of Tumor in hPD1/hPD-L1 mice on Day 16 of administration (100 mg/kg, PO)

BIPHENYL COMPOUND AS IMMUNOMODULATOR, PREPARATION METHOD THEREFOR AND APPLICATION THEREOF

CROSS-REFERENCE TO RELATED APPLICATIONS

This application is a United States National Phase Application filed under 35 U.S.C. § 371 from International Patent Application No. PCT/CN2021/126917, filed on Oct. 28, 2021, which claims the benefit of priority from Chinese Application No. 202011178102.4, filed on Oct. 29, 2020. The contents and disclosure of each of the foregoing applications are incorporated by reference herein in their entireties.

TECHNICAL FIELD

This disclosure belongs to the field of medicinal chemistry, and particularly relates to a biphenyl compound as an immunomodulator and preparation method therefor and use thereof.

BACKGROUND

Tumor immunotherapy is a new treatment method that inhibits or kills tumor cells by stimulating the body's immune system and enhancing its own anti-tumor immunity. This method has achieved a breakthrough after more than 100 years of efforts. In 2013, the journal Science listed tumor immunotherapy as the first of the top ten scientific breakthroughs of the year (Couzin-Frankel J., 2013, *Science*, 342: 1432-1433), and it has become one of the most promising areas of antitumor therapy.

Compared with normal cells, tumor cells have a variety of genetic and epigenetic changes, and the immune system can use the surface antigens produced by tumor cells to distinguish them, thereby triggering an anti-tumor immune response. In the process of T cell anti-tumor immunity, after being activated by T cell receptor (TCR)-mediated antigen recognition signals, it comprehensively regulates T cell effects through co-stimulatory and co-inhibitory signals, including cytotoxic T-lymphocyte associated antigen 4 (CTLA4), programmed death protein 1 (PD-1), V-domain immunoglobulin suppressor of T-cell activation (VISTA), T cell immunoglobulin and mucin domain—containing-3 (TIM3), lymphocyte activation gene 3 (LAG3) and other inhibitory receptors for inhibitory signals, as well as CD28, CD134 (OX40), glucocorticoid-induced TNFR-related protein (GITR), CD137, CD27, HVEM and other activating receptors for stimulatory signals (Mellman I., Coukos G., Dranoff G., 2011, *Nature*, 480: 480-489). Under normal physiological conditions, immunocheckpoints are involved in maintaining immune tolerance to self-antigens and avoiding autoimmune diseases on the one hand, and on the other hand, avoiding excessive activation of immune responses leading to tissue damage. However, in tumor cells, immune killing can be avoided by inhibiting T cell activation through immunocheckpoints. Therefore, it is required to reactivate T cells to attack tumor cells by activating co-stimulatory signals (stepping on the "accelerator") and inhibiting co-inhibitory signals (releasing the "brake"), thereby achieving tumor immunotherapy.

PD-1 is expressed in activated T cells, B cells and myeloid cells. It belongs to the CD28 family and is a type 1 transmembrane glycoprotein on T cells, consisting of 288 amino acids. The molecular structure of PD-1 consists of an extracellular region with immunoglobulin IgV-like (amino acids 35-145), a transmembrane region, and a cytoplasmic tail region with the function of linking signal peptides, and the extracellular region on PD-1 binds to ligands to play important functions (Cheng X., Veverka V, Radhakrishnan A., et al. 2013, *J. Biol. Chem.*, 288: 11771-11785). Programmed death protein ligand 1 (PD-L1) is one of the ligands of PD-1, belongs to the B7 family, and can be persistently expressed in a variety of tumor cells, T cells, and antigen presenting cells (APCs) and a variety of non-hematopoietic cells, and it is also a type1 transmembrane glycoprotein, which consists of 290 amino acids. The interaction of PD-1 and PD-L1 inhibits T cell activation, which is essential for maintaining immune tolerance in normal organisms. In tumor cells or being infected by virus, PD-1 on T cells is induced to be highly expressed, and the expression of PD-L1 is up-regulated, which leads to continuous activation of the PD-1 signaling pathway and inhibits T cell proliferation, resulting in immune escape of tumor cells and pathogens (Fuller M. J., Callendret B., Zhu B., et al. 2013, *Proc. Natl. Acad. Sci. USA.*, 110: 15001-15006; Dolan D. E., Gupta S., 2014, *Cancer Control*, 21: 231-237; Chen L., Han X., 2015, *J. Clin. Invest.*, 125: 3384-3391; Postow M. A., Callahan M. K., Wolchok J. D., 2015, *J. Clin. Oncol.*, 33: 1974-1982). Multiple antibody drugs for PD-1 and PD-L1 approved in recent years have fully proved that blocking PD-1/PD-L1 interaction is a very effective treatment in tumor immunotherapy and for other immune-related diseases.

Studies have found that PD-L1 can interact with CD80 and inhibit the binding of PD-L1 and PD-1 and inhibit the ability of T cell activation. Therefore, the immune activation caused by blocking CD80/PD-L1 interaction may also promote the enhancement of T cell activity, thereby providing new therapeutic opportunities for immune-related diseases (Sugiura D., Maruhashi T., Okazaki 11-mi, et al. 2019, *Science*, 364: 558-566).

So far, important progress has been made in PD-1/PD-L1-targeted antibody drugs. However, all antibody drugs have to be administered by injection, which causes multiple ADMET problems, serious side effects related to the immune system, etc. Compared with antibody drugs, small-molecule immunomodulators have advantages in some way, including oral administration, better tissue penetration, and the ability to minimize side effects by adjusting their pharmacological properties. In addition, small-molecule inhibitors will have a better price advantage.

Clinical studies of PD-1/PD-L1 antibody drugs show that nivolumab has a half time $T_{1/2}$ of 25.2 days and it is dosed every two weeks; pembrolizumab has a half time $T_{1/2}$ of 25 days and it is dosed every three weeks; atezolizumab has a half time $T_{1/2}$ of 27 days and it is dosed every three weeks. The dosing frequencies of the above drugs are all shorter than their drug half-lives, indicating that the continuous exposure of such target drugs in vivo is the key to obtain ideal clinical efficacy. However, the existing small-molecule immunomodulators have low exposure in vivo and short continuous exposure time, which will affect the clinical efficacy.

SUMMARY

One aspect of this disclosure relates to a small-molecule biphenyl compound capable of targeting PD-L1, or its isomers, pharmaceutically acceptable salts, precursors and metabolites.

Another aspect of this disclosure relates to a preparation method of the compound described herein.

Yet another aspect of this disclosure relates to a pharmaceutical composition comprising the compound of this disclosure as an active ingredient, and the clinical application of the compound or the pharmaceutical composition of the present invention for treatment and/or prevention of various other diseases related to the target PD-L1 for tumor immunotherapy and immunity.

As a small-molecule PD-L1 inhibitor, compared with antibodies, it needs to be optimized in terms of target binding strength and continuous exposure time in vivo, so as to narrow the possible gap between the two sides in terms of drug efficacy. Therefore, the inventors expect to develop a novel small-molecule PD-L1 immunomodulator with higher activity and better oral absorption characteristics, especially with sufficient in vivo exposure and continuous exposure time, and better targeting to tumor tissue to meet the unmet clinical needs.

This disclosure overcomes the disadvantage that the existing PD-1/PD-L1 antibody drugs all need to be administrated by injection, and provides a novel small-molecule immunomodulator with excellent oral absorption characteristics, especially the compounds of this disclosure have ideal in vivo exposure and continuous exposure time, can target tumor tissue, and can be enriched in tumor tissue and form a higher exposure concentration in tumor tissue, which is conductive to exert better anti-tumor activity in treatment, so as to achieve better curative effect.

This disclosure relates to a compound of formula (I), or its isomers, pharmaceutically acceptable salts, precursors and metabolites, $C_1$-$C_6$ haloalkoxy $C_1$-$C_6$ alkyl, $C_3$-$C_{14}$ cycloalkyl, 3- to 14-membered heterocycloalkyl, $C_3$-$C_{14}$ cycloalkyl-$C_1$-$C_4$ alkyl, and 3- to 14-membered heterocycloalkyl-$C_1$-$C_4$ alkyl;

$R^4$ is selected from hydrogen and $C_1$-$C_6$ alkyl, wherein the $C_1$-$C_6$ alkyl may be optionally substituted by one or more substituents selected from hydroxyl group, carboxy and halogen;

X is selected from —O—, —S—, and —N($R^a$)—;

$R^a$ is selected from hydrogen, $C_1$-$C_6$ alkyl and $C_1$-$C_6$ haloalkyl;

m is 1, 2 or 3;

n is 1, 2 or 3;

In some embodiments, $R^1$ and $R^2$ can be identically or differently selected from methyl, cyano and halogen;

In some embodiments, $R^1$ and $R^2$ can be identically or differently is selected from methyl, cyano, fluorine and chlorine;

In some embodiments, $R^1$ is selected from $C_1$-$C_6$ alkyl, cyano and halogen;

In some embodiments, $R^2$ is selected from $C_1$-$C_6$ alkyl and halogen;

In some embodiments, $R^1$ is selected from methyl, cyano, fluorine and chlorine;

In some embodiments, $R^2$ is selected from methyl and chlorine;

In some embodiments, $R^3$ is selected from hydrogen, $C_1$-$C_6$ alkyl and $C_1$-$C_6$ haloalkyl;

In some embodiments, $R^3$ is selected from hydrogen, $C_1$-$C_6$ alkyl and $C_1$-$C_6$ fluoroalkyl;

In some embodiments, $R^3$ is selected from methyl, ethyl and —$CHF_2$;

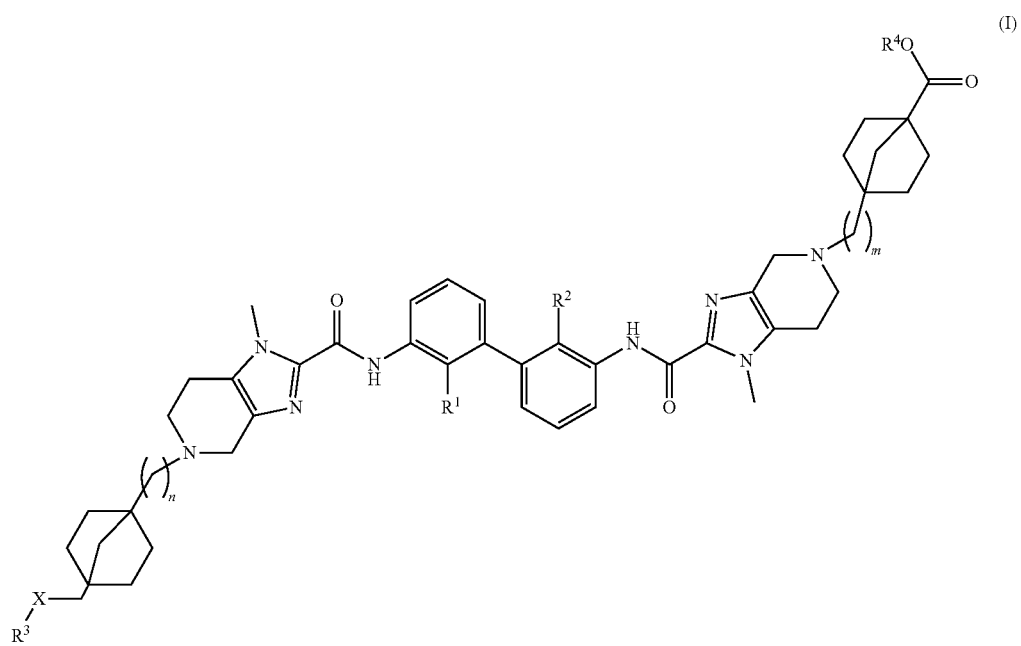

wherein
$R^1$ and $R_2$ can be identically or differently selected from $C_1$-$C_6$ alkyl, cyano and halogen;
$R^3$ is selected from hydrogen, $C_1$-$C_6$ alkyl, $C_2$-$C_6$ alkenyl $C_1$-$C_6$ alkyl, $C_2$-$C_6$ alkynyl $C_1$-$C_6$ alkyl, $C_1$-$C_6$ haloalkyl, $C_1$-$C_6$ alkoxy $C_1$-$C_6$ alkyl, mono-$C_1$-$C_6$ alkylamino $C_1$-$C_6$ alkyl, di-$C_1$-$C_6$ alkylamino $C_1$-$C_6$ alkyl, In some embodiments, $R^4$ is selected from hydrogen and $C_1$-$C_6$ alkyl;

In some embodiments, $R^4$ is selected from hydrogen and methyl;

In some embodiments, X is selected from —O—, and —N($R^a$)—;

In some embodiments, X is selected from —O—;
In some embodiments, $R^a$ is selected from hydrogen and $C_1$-$C_6$ alkyl;
In some embodiments, $R^a$ is methyl;
In some embodiments, m is 1 or 2;
In a preferred aspect, this disclosure relates to a compound of formula (I), or its isomers, pharmaceutically acceptable salts, precursors and metabolites, wherein $R^1$ and $R^2$ can be identically or differently selected from methyl, cyano, fluorine, chlorine and bromine;

$R^3$ is selected from $C_1$-$C_6$ alkyl, $C_2$-$C_6$ alkenyl $C_1$-$C_6$ alkyl, $C_2$-$C_6$ alkynyl $C_1$-$C_6$ alkyl, $C_1$-$C_6$ haloalkyl, $C_1$-$C_6$ alkoxy $C_1$-$C_6$ alkyl, mono-$C_1$-$C_6$ alkylamino $C_1$-$C_6$ alkyl, di-$C_1$-$C_6$ alkylamino $C_1$-$C_6$ alkyl, $C_1$-$C_6$ haloalkoxy $C_1$-$C_6$ alkyl, $C_3$-$C_{14}$ cycloalkyl, 3- to 14-membered heterocycloalkyl, $C_3$-$C_{14}$ cycloalkyl-$C_1$-$C_4$ alkyl, and 3- to 14-membered heterocycloalkyl-$C_1$-$C_4$ alkyl;

$R^4$ is selected from hydrogen and $C_1$-$C_6$ alkyl, wherein the $C_1$-$C_6$ alkyl is optionally substituted by one or more substituents selected from hydroxyl group, and halogen;

X is selected from —O—, and —N($R^a$)—;

$R^a$ is selected from hydrogen, methyl, ethyl, isopropyl and $C_1$-$C_6$ haloalkyl;

m is 1, 2 or 3;

n is 1, 2 or 3;

In some embodiments, $R^1$ and $R^2$ can be identically or differently selected from methyl, cyano, fluorine and chlorine;

In some embodiments, $R^1$ is selected from methyl, cyano, fluorine and chlorine;

In some embodiments, $R^2$ is selected from methyl and chlorine;

In some embodiments, $R^3$ is selected from $C_1$-$C_6$ alkyl and $C_1$-$C_6$ haloalkyl;

In some embodiments, $R^3$ is selected from $C_1$-$C_6$ alkyl and $C_1$-$C_6$ fluoroalkyl;

In some embodiments, $R^3$ is selected from methyl, ethyl and —$CHF_2$;

In some embodiments, $R^4$ is selected from hydrogen and $C_1$-$C_6$ alkyl;

In some embodiments, $R^4$ is selected from hydrogen and methyl;

In some embodiments, $R^a$ is selected from hydrogen, methyl, ethyl and isopropyl;

In some embodiments, $R^a$ is methyl;

In some embodiments, m is 1 or 2;

In some embodiments, X is selected from —O—;

in another preferred aspect, this disclosure relates to a compound of formula (I), or its isomers, pharmaceutically acceptable salts, precursors and metabolites, wherein $R^1$ and $R^2$ can be identically or differently selected from methyl, cyano, fluorine and chlorine;

$R^3$ is selected from $C_1$-$C_6$ alkyl, $C_2$-$C_6$ alkenyl $C_1$-$C_6$ alkyl, $C_2$-$C_6$ alkynyl $C_1$-$C_6$ alkyl, $C_1$-$C_6$ haloalkyl, $C_1$-$C_6$ alkoxy $C_1$-$C_6$ alkyl, mono-$C_1$-$C_6$ alkylamino $C_1$-$C_6$ alkyl, di-$C_1$-$C_6$ alkylamino $C_1$-$C_6$ alkyl, $C_1$-$C_6$ haloalkoxy $C_1$-$C_6$ alkyl, $C_3$-$C_{14}$ cycloalkyl, and 3- to 14-membered heterocycloalkyl;

$R^4$ selected from hydrogen and $C_1$-$C_6$ alkyl, wherein the $C_1$-$C_6$ alkyl is optionally substituted by halogen substituent(s);

X is selected from —O—, and —N($R^a$)—;

$R^a$ is selected from hydrogen, methyl, ethyl and $C_1$-$C_6$ haloalkyl;

m is 1 or 2;

n is 1, 2 or 3;

In some embodiments, $R^1$ is selected from methyl, cyano, fluorine and chlorine;

In some embodiments, $R^2$ is selected from methyl and chlorine;

In some embodiments, $R^3$ is selected from $C_1$-$C_6$ alkyl and $C_1$-$C_6$ haloalkyl;

In some embodiments, $R^3$ is selected from $C_1$-$C_6$ alkyl and $C_1$-$C_6$ fluoroalkyl;

In some embodiments, $R^3$ is selected from methyl, ethyl and —$CHF_2$;

In some embodiments, $R^4$ is selected from hydrogen and $C_1$-$C_6$ alkyl;

In some embodiments, $R^4$ is selected from hydrogen and methyl;

In some embodiments, $R^a$ is selected from hydrogen, methyl and ethyl;

In some embodiments, $R^a$ is methyl;

In some embodiments, X is selected from —O—;

in yet another preferred aspect, this disclosure relates to a compound of formula (I), or its isomers, pharmaceutically acceptable salts, precursors and metabolites, wherein $R^1$ and $R^2$ can be identically or differently selected from methyl, cyano, fluorine and chlorine;

$R^3$ is selected from $C_1$-$C_6$ alkyl, $C_2$-$C_6$ alkenyl $C_1$-$C_6$ alkyl, $C_2$-$C_6$ alkynyl $C_1$-$C_6$ alkyl, $C_1$-$C_6$ haloalkyl, $C_1$-$C_6$ alkoxy $C_1$-$C_6$ alkyl, mono-$C_1$-$C_6$ alkylamino $C_1$-$C_6$ alkyl, di-$C_1$-$C_6$ alkylamino $C_1$-$C_6$ alkyl, and $C_1$-$C_6$ haloalkoxy $C_1$-$C_6$ alkyl;

$R^4$ is selected from hydrogen and $C_1$-$C_6$ alkyl, wherein the $C_1$-$C_6$ alkyl is optionally substituted by substituents selected from fluorine, chlorine and bromine;

X is selected from —O—, and —N($R^a$)—;

$R^a$ is selected from hydrogen, methyl, ethyl, $C_1$-$C_6$ fluoroalkyl and $C_1$-$C_6$ chloroalkyl;

m is 1 or 2;

n is 1, 2 or 3;

In some embodiments, $R^1$ is selected from methyl, cyano, fluorine and chlorine;

In some embodiments, $R^2$ is selected from methyl and chlorine;

In some embodiments, $R^3$ is selected from $C_1$-$C_6$ alkyl and $C_1$-$C_6$ haloalkyl;

In some embodiments, $R^3$ is selected from $C_1$-$C_6$ alkyl and $C_1$-$C_6$ fluoroalkyl;

In some embodiments, $R^3$ is selected from methyl, ethyl and —$CHF_2$;

In some embodiments, $R^4$ is selected from hydrogen and $C_1$-$C_6$ alkyl;

In some embodiments, $R^4$ is selected from hydrogen and methyl;

In some embodiments, $R^a$ is selected from hydrogen, methyl and ethyl;

In some embodiments, $R^a$ is methyl;

In some embodiments, X is selected from —O—;

in a particularly preferred aspect, this disclosure relates to a compound of formula (I), or its isomers, pharmaceutically acceptable salts, precursors and metabolites, wherein $R^1$ and $R^2$ can be identically or differently selected from methyl, cyano, fluorine and chlorine;

$R^3$ is selected from $C_1$-$C_6$ alkyl, $C_2$-$C_6$ alkenyl $C_1$-$C_6$ alkyl, $C_2$-$C_6$ alkynyl $C_1$-$C_6$ alkyl, $C_1$-$C_6$ haloalkyl, $C_1$-$C_6$ alkoxy $C_1$-$C_6$ alkyl, and $C_1$-$C_6$ haloalkoxy $C_1$-$C_6$ alkyl;

$R^4$ is selected from hydrogen and $C_1$-$C_6$ alkyl, wherein the $C_1$-$C_6$ alkyl is optionally substituted substituents selected from by fluorine and chlorine;

X is selected from —O—, and —N($R^a$)—;

m is 1 or 2;

n is 1, 2 or 3;

$R^a$ is methyl;

In some embodiments, $R^1$ is selected from methyl, cyano, fluorine and chlorine;

In some embodiments, $R^2$ is selected from methyl and chlorine;

In some embodiments, $R^3$ is selected from $C_1$-$C_6$ alkyl and $C_1$-$C_6$ haloalkyl;

In some embodiments, $R^3$ is selected from $C_1$-$C_6$ alkyl and $C_1$-$C_6$ fluoroalkyl;

In some embodiments, $R^3$ is selected from methyl, ethyl and —$CHF_2$;

In some embodiments, $R^4$ is selected from hydrogen and $C_1$-$C_6$ alkyl;

In some embodiments, $R^4$ is selected from hydrogen and methyl;

In some embodiments, X is selected from —O—;

in another particularly preferred aspect, this disclosure relates to a compound of formula (I), or its isomers, pharmaceutically acceptable salts, precursors and metabolites, wherein $R^1$ and $R^2$ can be identically or differently selected from methyl, cyano, fluorine and chlorine;

$R^3$ is selected from $C_1$-$C_6$ alkyl, $C_2$-$C_6$ alkenyl $C_1$-$C_6$ alkyl, $C_1$-$C_6$ haloalkyl, $C_1$-$C_6$ alkoxy $C_1$-$C_6$ alkyl, and $C_1$-$C_6$ haloalkoxy $C_1$-$C_6$ alkyl;

$R^4$ is selected from hydrogen and methyl;

X is selected from —O— and —N($R^a$)—;

m is 1 or 2;

n is 1, 2 or 3;

$R^a$ is methyl;

In some embodiments, $R^1$ is selected from methyl, cyano, fluorine and chlorine;

In some embodiments, $R^2$ is selected from methyl and chlorine;

In some embodiments, $R^3$ is selected from $C_1$-$C_6$ alkyl and $C_1$-$C_6$ haloalkyl;

In some embodiments, $R^3$ is selected from $C_1$-$C_6$ alkyl and $C_1$-$C_6$ fluoroalkyl;

In some embodiments, $R^3$ is selected from methyl, ethyl and —$CHF_2$;

In some embodiments, X is selected from —O—.

This disclosure relates to a compound of formula (I), including but not limited to:

| Compound Structural Formula | Compound Name |
|---|---|
| (structure) | 4-(2-(2-(2'-chloro-3'-(5-(3-(4-(methoxymethyl)bicyclo[2.2.1]heptan-1-yl)propyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid |

| Compound Structural Formula | Compound Name |
|---|---|
| 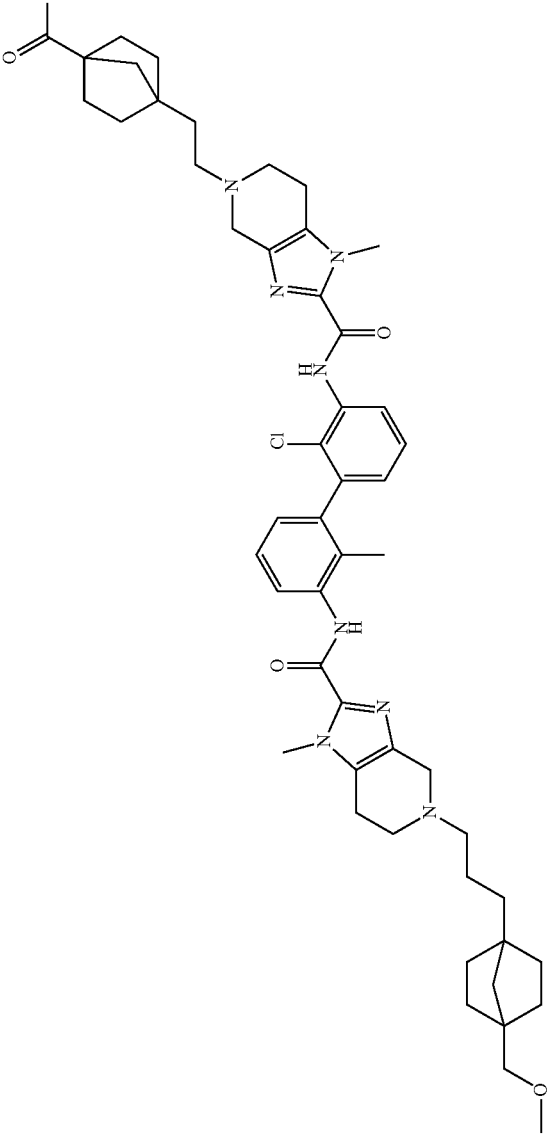 | 4-(2-(2'-chloro-3'-(5-(3-(4-(methoxymethyl)bicyclo[2.2.1]heptan-1-yl)propyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid |

| Compound Structural Formula | Compound Name |
|---|---|
| 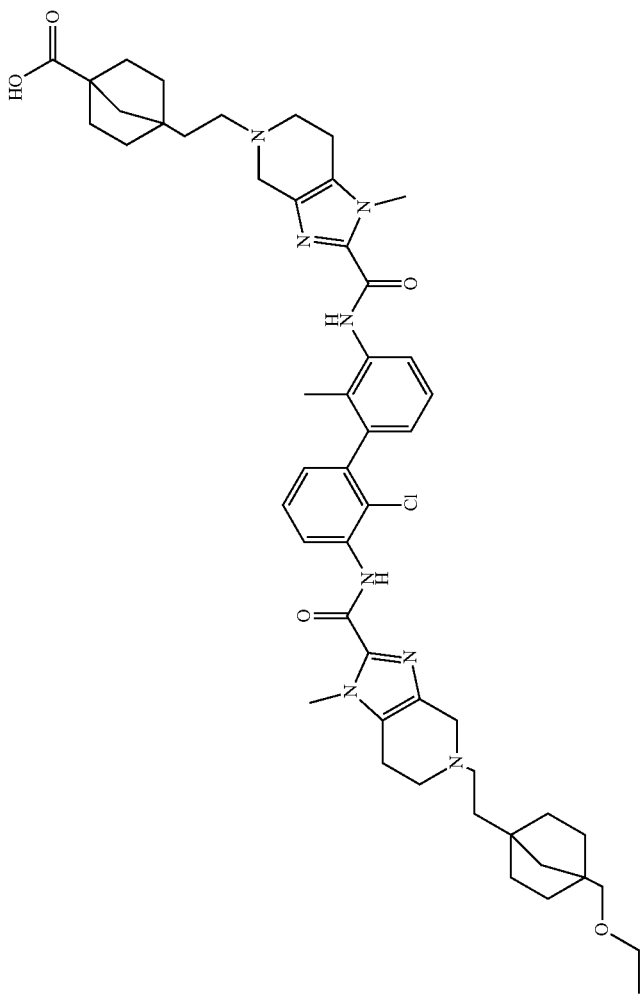 | 4-(2-(2-((2'-chloro-3'-(5-(2-(4-(ethoxymethyl)bicyclo[2.2.1]heptan-1-yl)ethyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid |

| Compound Structural Formula | Compound Name |
|---|---|
| (structure) | 4-(2-(2-(2'-chloro-3'-(5-(2-(4-(methoxymethyl)bicyclo[2.2.1]heptan-1-yl)ethyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid |

| Compound Structural Formula | Compound Name |
|---|---|
| 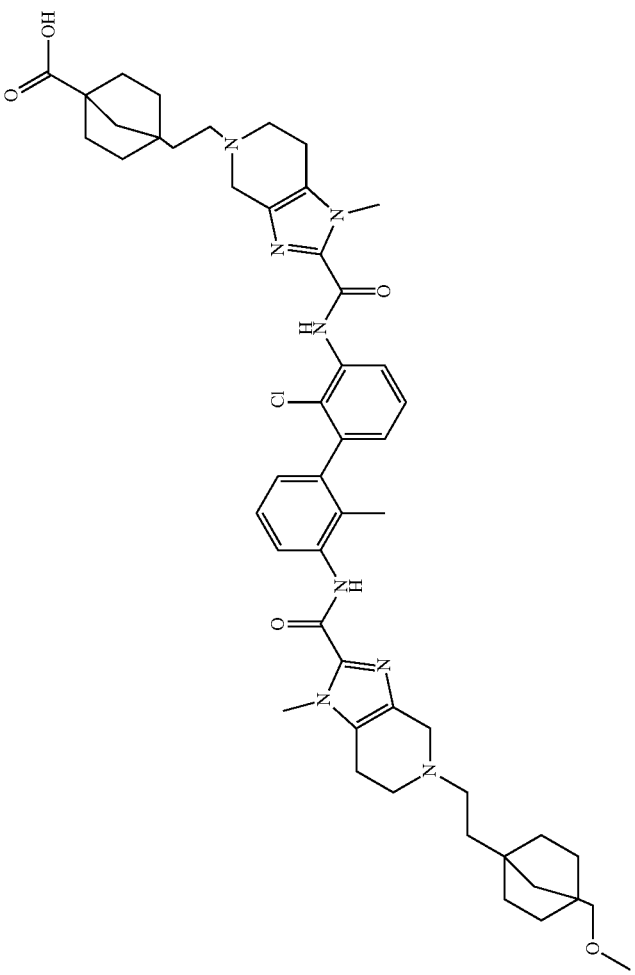 | 4-(2-(2-chloro-3'-(5-(2-(4-(methoxymethyl)bicyclo[2.2.1]heptan-1-yl)ethyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid |

| Compound Structural Formula | Compound Name |
|---|---|
| 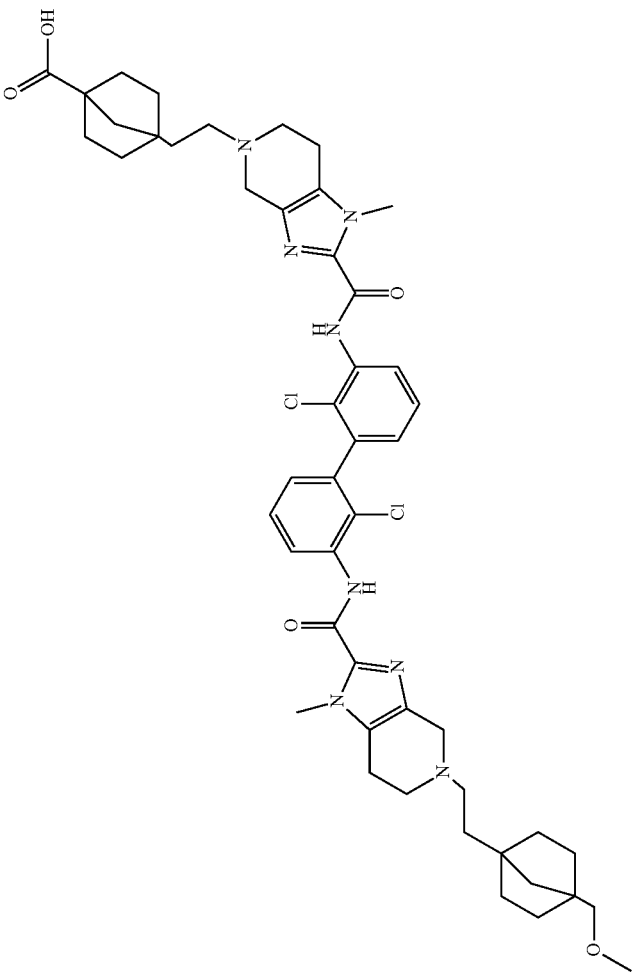 | 4-(2-(2-(2'-(((2,2'-dichloro-3'-(5-(2-(4-(methoxymethyl)bicyclo[2.2.1]heptan-1-yl)ethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid |

| Compound Structural Formula | Compound Name |
|---|---|
| 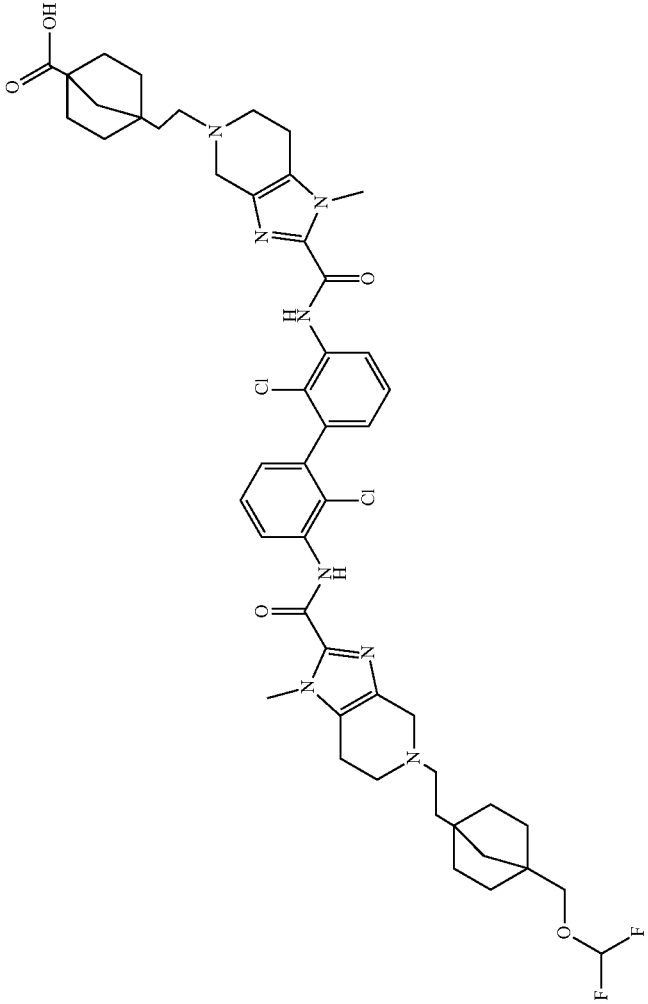 | 4-(2-(2-(2,2'-dichloro-3'-(5-(2-(4-((difluoromethoxy)methyl)bicyclo[2.2.1]heptan-1-yl)ethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid |

| Compound Structural Formula | Compound Name |
|---|---|
| 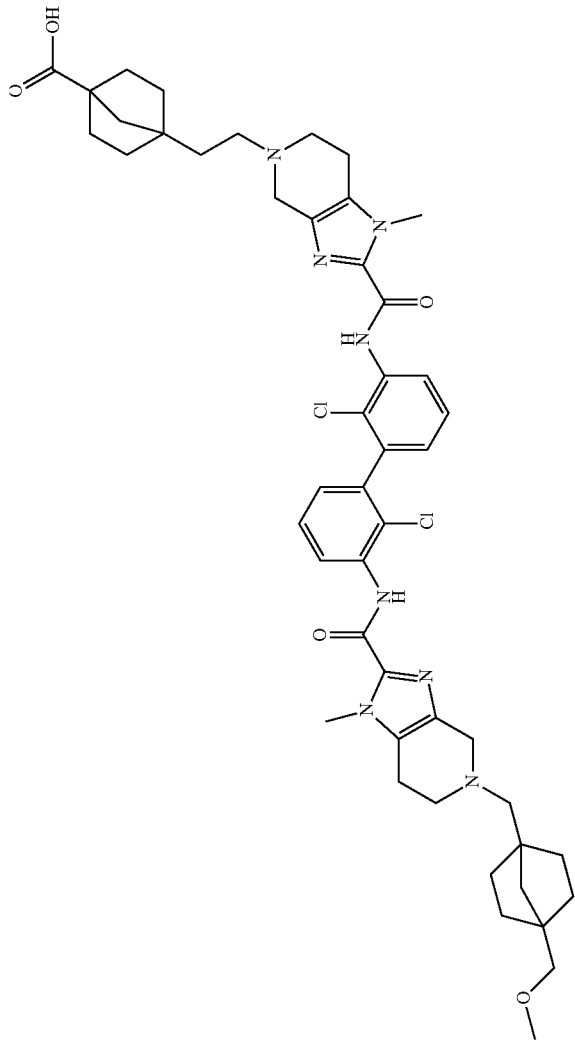 | 4-(2-(2-((2,2'-dichloro-3'-(5-((4-(methoxymethyl)bicyclo[2.2.1]heptan-1-yl)methyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid |

| Compound Structural Formula | Compound Name |
|---|---|
| (structure) | 4-((2-((2,2'-dichloro-3'-(5-((4-(methoxymethyl)bicyclo[2.2.1]heptan-1-yl)methyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)bicyclo[2.2.1]heptane-1-carboxylic acid |
| (structure) | 4-((2-((2-chloro-3'-(5-((4-(methoxymethyl)bicyclo[2.2.1]heptan-1-yl)methyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)methyl)bicyclo[2.2.1]heptane-1-carboxylic acid |

| Compound Structural Formula | Compound Name |
|---|---|
| 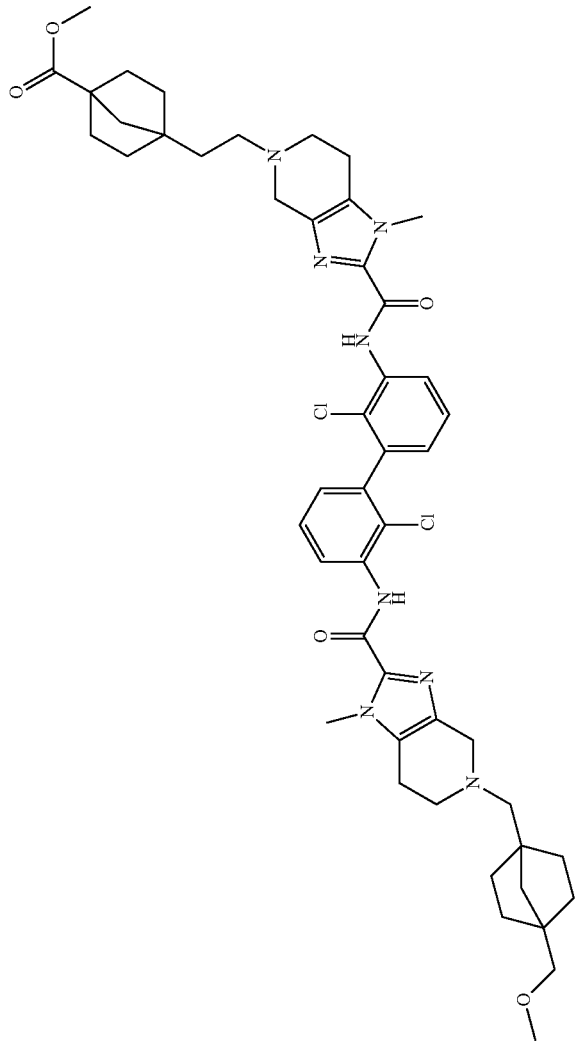 | 4-(2-(2-(2-((2,2'-dichloro-3'-(5-((4-(methoxymethyl)bicyclo[2.2.1]heptan-1-yl)methyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid methyl ester |

| Compound Structural Formula | Compound Name |
|---|---|
| 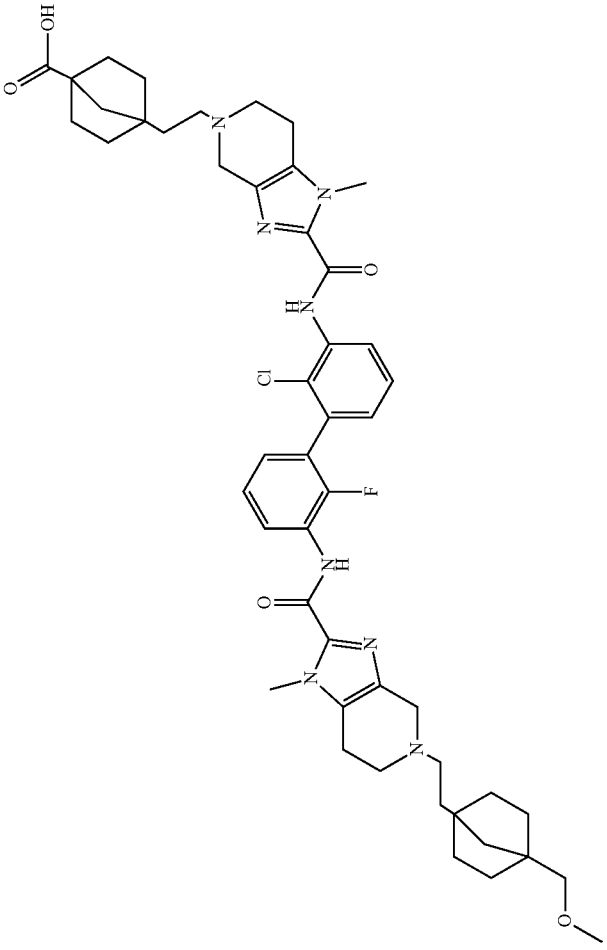 | 4-(2-(2-(2-chloro-2'-fluoro-3'-(5-(2-(4-(methoxymethyl)bicyclo[2.2.1]heptan-1-yl)ethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid |

| Compound Structural Formula | Compound Name |
|---|---|
| -continued | 4-(2-(2-(2-chloro-3'-(5-(2-(4-((difluoromethoxy)methyl)bicyclo[2.2.1]heptan-1-yl)ethyl)-1-methyl-4,5,6,7-tetrahydro-1H-imidazo[4,5-c]pyridine-2-carboxamido)-2'-fluoro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid |

| Compound Structural Formula | Compound Name |
|---|---|
| 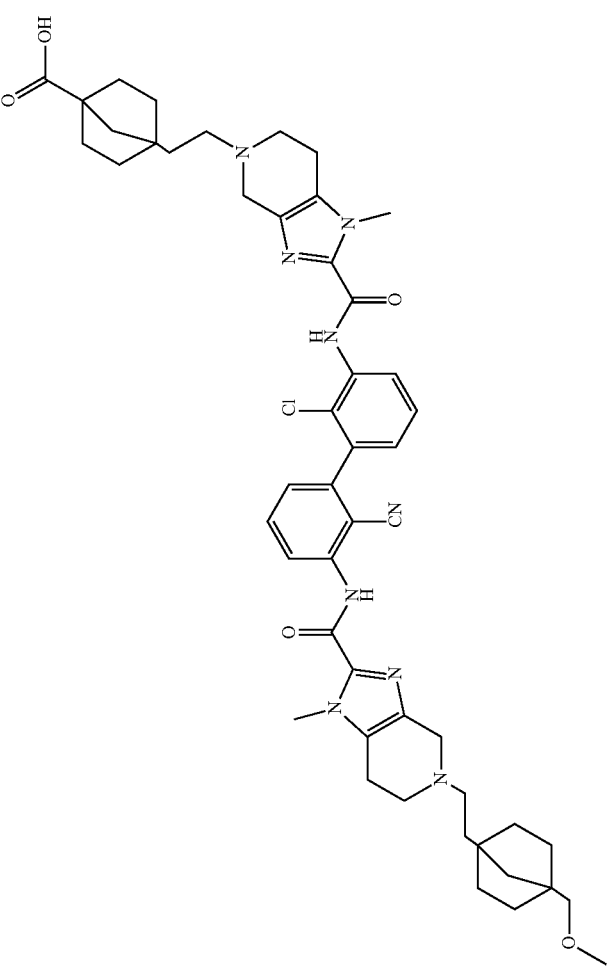 | 4-(2-(2-(2-(2-chloro-2'-cyano-3'-(5-(2-(4-(methoxymethyl)bicyclo[2.2.1]heptan-1-yl)ethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid |

| Compound Structural Formula | Compound Name |
|---|---|
| -continued | |
|  | 4-(2-(2'-cyano-3'-(5-(2-(4-(methoxymethyl)bicyclo[2.2.1]heptan-1-yl)ethyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid |

| Compound Structural Formula | Compound Name |
|---|---|
| -continued | |
| (structure) | 4-((2-chloro-3'-(5-(2-(4-(methoxymethyl)bicyclo[2.2.1]heptan-1-yl)ethyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)methyl)bicyclo[2.2.1]heptane-1-carboxylic acid |

| Compound Structural Formula | Compound Name |
|---|---|
| (structure) | 4-(2-(2'-chloro-3'-(5-((4-(methoxymethyl)bicyclo[2.2.1]heptan-1-yl)methyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid |

Definition of Terms

In each part of this specification, the substituents of the compound of the present invention are disclosed according to the types or scopes of groups. Particularly, this disclosure includes each independent subcombination of each member of the types and scopes of these groups. For example, the term "$C_1$-$C_6$ alkyl" specifically refers to the independently disclosed methyl, ethyl, $C_3$ alkyl, $C_4$ alkyl, $C_5$ alkyl, and $C_6$ alkyl, or the independently disclosed "$C_1$-$C_4$ alkyl" or the independently disclosed "$C_1$-$C_3$ alkyl".

The "halogen" mentioned in this disclosure refers to fluorine, chlorine, bromine or iodine, with priority being fluorine or chlorine or bromine.

The "alkyl" mentioned in this disclosure includes straight-chained or branched alkyls. The "$C_1$-$C_6$ alkyl" mentioned in this disclosure refers to alkyl groups with 1 to 6 carbon atoms, preferably to methyl, ethyl, n-propyl or isopropyl, n-butyl, isobutyl or tert-butyl. The alkyl in the compounds of this disclosure may be optionally substituted or unsubstituted, and the substituents for substitution may include alkyl, halogen, alkoxyl, haloalkyl, cyano, hydroxyl, and the like. Examples of alkyl of this disclosure include methyl, ethyl, n-propyl, isopropyl, n-butyl, isobutyl, tert-butyl, and the like.

The "alkenyl" mentioned in this disclosure refers to a straight-chained or branched monovalent hydrocarbonyl having 2 to 12 carbon atoms, or 2 to 8 carbon atoms, or 2 to 6 carbon atoms, or 2 to 4 carbon atoms, in which at least one position is unsaturated, that is, one C—C bond is a $sp^2$ double bond. The alkenyl group can be independently and optionally substituted by one or more substituents described in this disclosure, including groups with "trans", "cis" or "E", "Z" positioning. The alkenyl can be $C_2$-$C_6$ alkenyl and its specific examples include, but are not limited to, vinyl (—CH=$CH_2$), allyl (—$CH_2$CH=$CH_2$), and the like.

The "alkynyl" mentioned in this disclosure refers to a straight-chained or branched monovalent hydrocarbonyl having 2 to 12 carbon atoms, or 2 to 8 carbon atoms, or 2 to 6 carbon atoms, or 2 to 4 carbon atoms, in which at least one position is unsaturated, that is, one C—C bond is a sp triple bond. The alkynyl group can be independently and optionally substituted by one or more substituents described in this disclosure. The alkynyl can be $C_2$-$C_6$ alkynyl and its specific examples include, but are not limited to, ethynyl (—C≡CH), propargyl (—$CH_2$C≡CH), and the like.

The "alkoxy" mentioned in this disclosure refers to a group of formula O-alkyl, wherein the oxygen atom has the ability to form bonds freely, so the alkoxy can be, such as, "$C_1$-$C_6$ alkoxy", and specifically it can be methoxy, ethoxy, n-propoxy, n-butoxy, isopropoxy, tert-butoxy, cyclopropoxy, and the like.

The "alkylamino" mentioned in this disclosure refers to a group formed by linking the above-mentioned alkyl to an amino group. The alkylamino can be, such as, "$C_1$-$C_6$ alkylamino", and specifically it can be methylamino, ethylamino, dimethylamino, methylisopropylamino, and the like.

The "$C_1$-$C_6$ haloalkyl" and "$C_1$-$C_6$ haloalkoxy" mentioned in this disclosure mean that one or more hydrogen atoms in the alkyl and the alkoxy are substituted by halogen atoms, especially fluorine or chlorine atoms. In some embodiments, substitution with fluorine atom is preferred, and they can be, for example, —$CF_3$, —$CHF_2$, —$CH_2F$, —$CH_2CH_2F$, —$CH_2CHF_2$, —$CH_2CF_3$, —$OCF_3$, —$OCHF_2$, —$OCH_2F$, —$OCH_2CH_2F$, —$OCH_2CHF_2$ or —$OCH_2CF_3$.

The "cycloalkyl" mentioned in this disclosure refers to a hydrocarbonyl monocyclic structure having a specified number of cyclocarbon atoms, which does not contain unsaturated bonds such as double bonds. The cycloalkyl can be $C_3$-$C_{14}$ cycloalkyl and $C_3$-$C_6$ cycloalkyl, for example, cyclopropyl, cyclobutyl, cyclopentyl, and cyclohexyl. The cycloalkyl in the compounds of this disclosure may be optionally substituted or unsubstituted, and the substituents for substitution may include alkyl, halogen, alkoxy, hydrocarbonyl, hydroxyl, and the like.

The "heterocycle" mentioned in this disclosure refers to unsubstituted and substituted monocyclic or polycyclic non-aromatic ring systems, partially unsaturated or fully saturated ring systems containing one or more heteroatoms. The preferred heteroatoms include N, O and S. Monocyclic heterocycles include, but are not limited to, pyrrolidinyl, imidazolindinyl, tetrahydrofuranyl, dihydroimidazolyl, dihydrofuranyl, piperidinyl, morpholinyl, thiomorpholino, perpiperazinyl, and the like. Polycyclic heterocycles include spiro, bridged, and fused heterocycles. The heterocyclic ring may be fused to an aryl group, a heterocyclic group, or a cycloalkyl ring.

From all the above descriptions, it is obvious to those skilled in the art that any group having a compound name, such as "$C_2$-$C_6$ alkenyl $C_1$-$C_6$ alkyl", should refer to the one being conventionally constructed from its derived parts such as a $C_1$-$C_6$ alkyl substituted by a $C_2$-$C_6$ alkenyl, where the $C_1$-$C_6$ alkyl and the $C_2$-$C_6$ alkenyl are defined as above. Other similar compound names such as "$C_2$-$C_6$ alkynyl $C_1$-$C_6$ alkyl" and "$C_3$-$C_{14}$ cycloalkyl-$C_1$-$C_4$-alkyl" can be understood in light of the foregoing.

Unless otherwise specifically defined, the term "substituted" means that one or more hydrogen atoms in a group can be independently substituted by a corresponding number of substituents. Those skilled in the art are able to identify (experimentally or theoretically) possible or impossible substitution position without much effort. The term "substituted" means a substituent including, but not limited to: cyano, carboxyl, halogen, hydroxyl, $C_1$-$C_6$ alkyl, $C_2$-$C_6$ alkenyl, $C_2$-$C_6$ alkenyl, $C_1$-$C_6$ alkoxy, mono-$C_1$-$C_6$ alkylamino $C_1$-$C_6$ alkyl, di-$C_1$-$C_6$ alkylamino $C_1$-$C_6$ alkyl, $C_1$-$C_6$ haloalkyl, $C_1$-$C_6$ alkoxy $C_1$-$C_6$ alkyl, $C_1$-$C_6$ haloalkoxy $C_1$-$C_6$ alkyl, $C_3$-$C_{14}$ cycloalkyl, 3- to 14-membered heterocycloalkyl, $C_3$-$C_{14}$ cycloalkyl-$C_1$-$C_4$ alkyl, and 3- to 14-membered heterocycloalkyl —$C_1$-$C_4$ alkyl.

Stereoisomers in the compounds described herein, when specifically designated by chemical names as (R)- or (S)-isomers, should be understood as (R)-isomers or (S)-isomers in their major configuration, respectively. Any asymmetric carbon atom can exist in the (R)-, (S)- or (R, S)-configuration, preferably in (R)- or (S)-configuration.

The "pharmaceutically acceptable salt" mentioned in the present invention refers to an acid addition salt prepared by the reaction of the compounds of this disclosure with a pharmaceutically acceptable acid, or a salt produced by the reaction of a compound with an acidic group with an alkaline compound. The acid is preferably selected from inorganic acids (such as hydrochloric acid, sulfuric acid, phosphoric acid, hydrobromic acid, or the like), and organic acids (such as oxalic acid, maleic acid, fumaric acid, malic acid, tartaric acid, lysine, histidine, citric acid, benzoic acid, or the like). The basic compound is preferably selected from sodium hydroxide, potassium hydroxide, calcium hydroxide, sodium carbonate, potassium bicarbonate, or the like. The above pharmaceutically acceptable salts are easily separated and can be purified by conventional separation methods, such as solvent extraction, dilution, recrystallization, column chromatography and preparative thin-layer chromatography (TLC).

For the compound of formula (I) of this disclosure
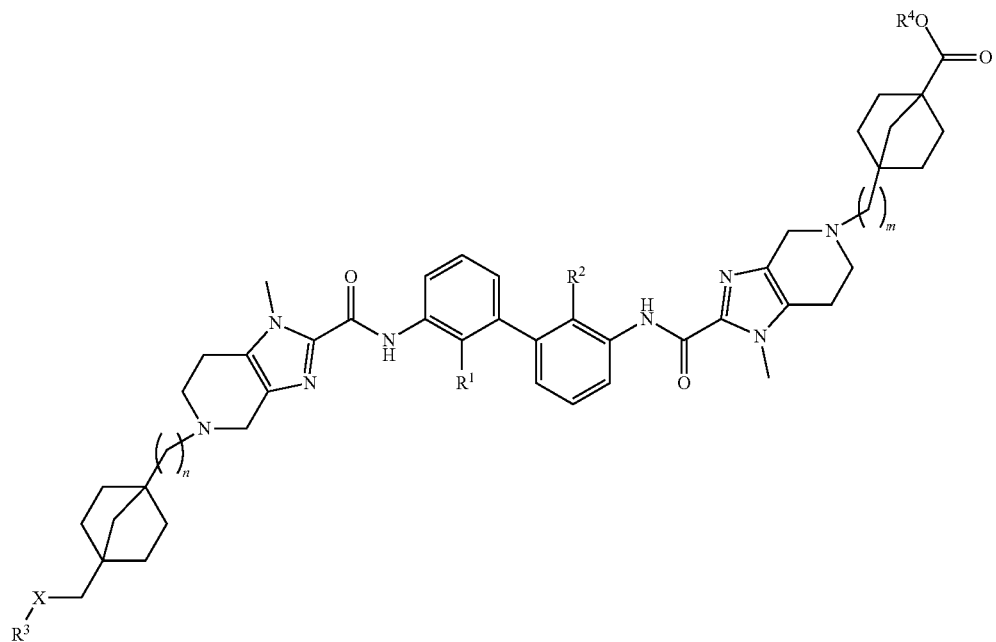
if m is 1, then the structural formula of the compound of formula (I) is
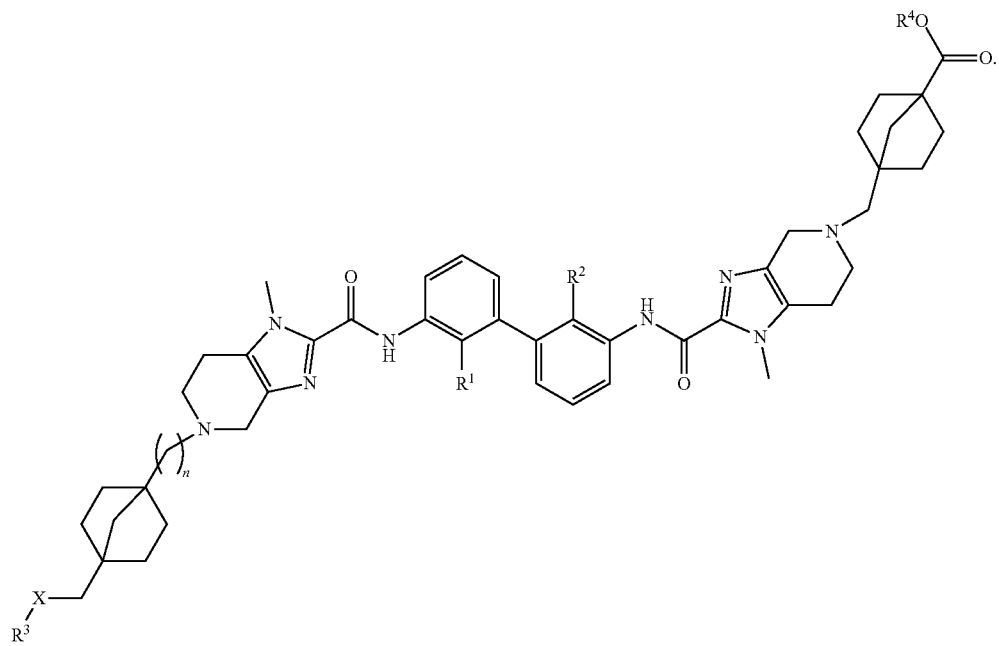

Other similar definitions can be understood with reference to the foregoing description.

Another aspect of this disclosure also relates to a pharmaceutical composition containing the compound described as above, or its isomers, pharmaceutically acceptable salts, precursors and metabolites as active ingredients.

The compound in this disclosure can optionally be used in combination with one or more other active ingredients, and their respective dosages and ratios can be adjusted by those skilled in the art according to the specific diseases and the specific conditions and clinical needs of patients.

The compound of formula (I), or its isomers, pharmaceutically acceptable salts, precursors and metabolites can be prepared by those skilled in the art (experience or references).

In case the compound of formula (I) in this disclosure has a structural formula inconsistent with its Chinese name, the chemical structural formula shall prevail.

Therefore, another aspect of this disclosure further provides a preparation method of the compound according to this disclosure.

The following synthesis route describes the preparation method of the compound of formula (I) in this disclosure.

The raw materials, reagents, catalysts and solvents used in the following synthesis diagrams can be prepared by methods well known to those of ordinary skills in the field of organic chemistry or can be commercially available. All final derivatives in this disclosure may be prepared by means of the methods described in the diagrams or similar methods, which are well known to those of ordinary skills in the field of organic chemistry. All variables applied to these diagrams are defined as above and below.

Preparation Method

The following variables are defined as described above, while the new variables are defined as described in this section. In addition, the compound of formula (I) and the related intermediates can be purified by common separation methods, such as extraction, recrystallization and silica gel column chromatography separation, and the like. The 200-300-mesh silica gel and TLC silica gel plates were produced by Qingdao Ocean Chemical Co., LTD. The chemical reagents used are analytically pure or chemically pure commercial products of general reagents and are used without further purification.

This disclosure provides a preparation method of the compound of formula (I), comprising the following steps:

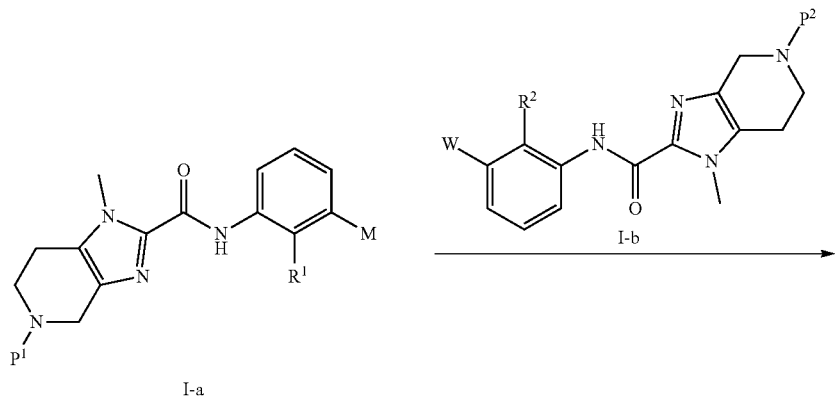

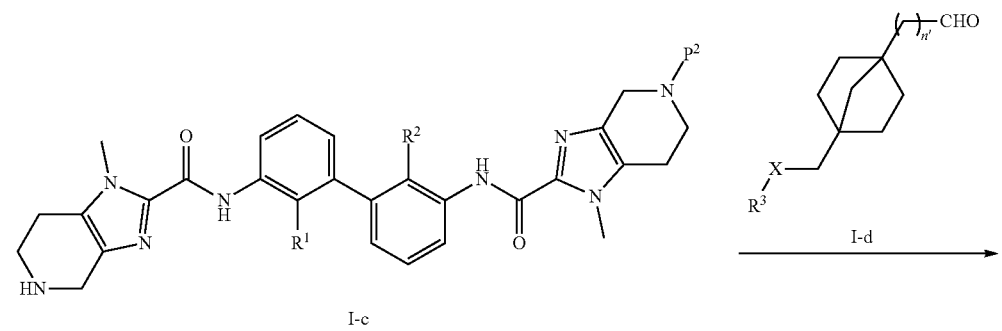

-continued
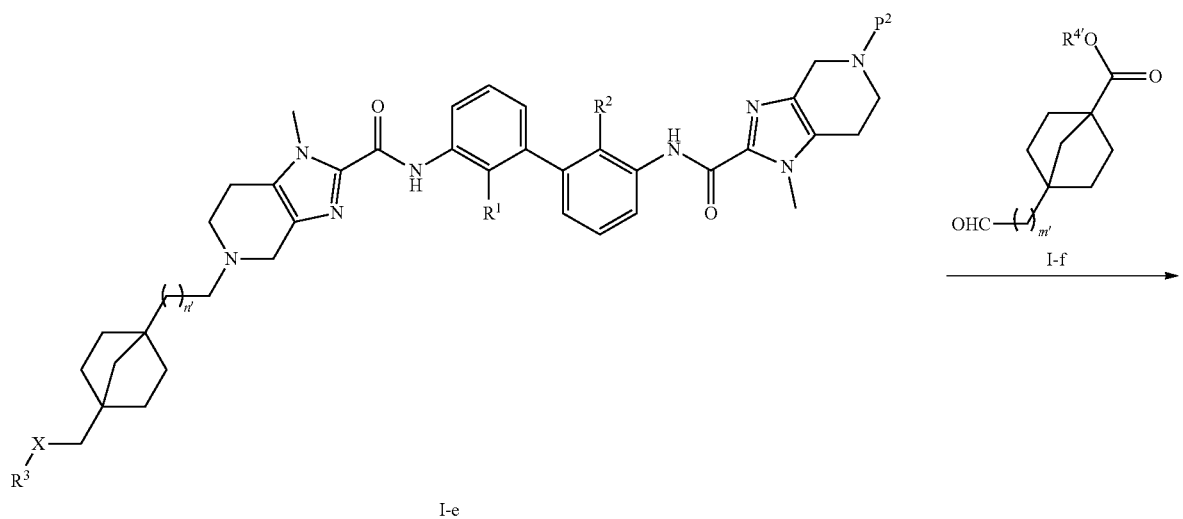
I-e
I-f
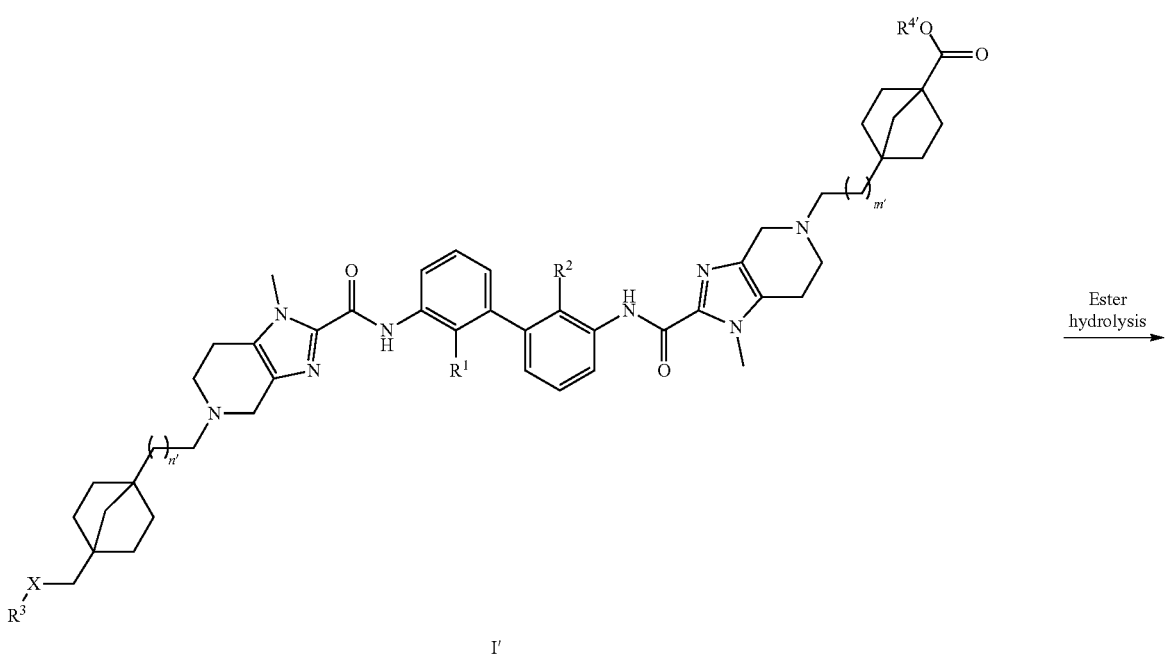
I'
Ester hydrolysis

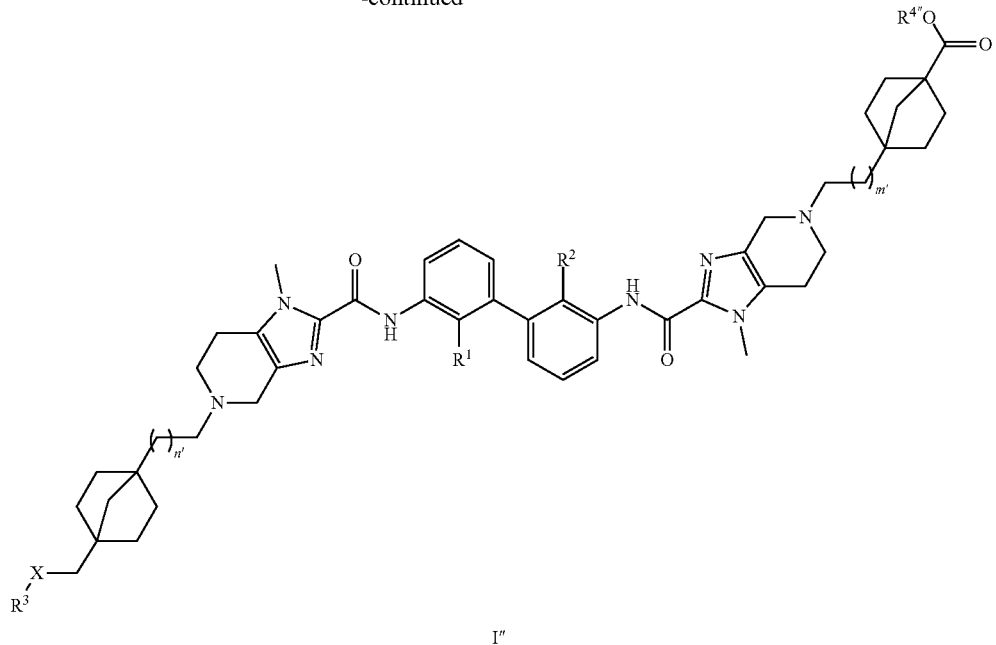

I''

1) deprotecting a compound of (I-a) in a first solvent by using a first acid, a first alkali or catalytic hydrogenolysis to remove a protecting group $P^1$, and allowing the resulting product without being separated or purified to further have a Suzuki reaction with a compound of formula (I-b) in a second solvent in the presence of a first catalyst and a second alkali to obtain a compound of formula (I-c);
2) allowing the compound of formula (I-c) and a compound of formula (I-d) to have reductive amination in a third solvent in the presence of a first reducing agent to obtain a compound of formula (I-e);
3) allowing the compound of formula (I-e) and a compound of formula (I-f) to have reductive amination in a fourth solvent in the presence of a second reducing agent to obtain a compound of formula (I'); and
optionally, further comprising 4), allowing the compound of formula (I') to have ester hydrolysis in the presence of a third alkali to obtain a compound of formula (I").

The compound of formula (I') can be used as the final product of formula (I). In addition, the compound of formula (I') can further have ester hydrolysis under an alkaline condition to obtain the compound of formula (I"), which can also be used as the final product of formula (I).

In the formula,

X, $R^1$, $R^2$, and $R^3$ are defined as above;

m' is selected from 0, 1, and 2, preferably from 0 and 1;

n' is selected from 0, 1, and 2;

$R^{4'}$ is defined in the same way as $R^4$ except that it is not hydrogen, and $R^4$ is defined as above;

$R^{4''}$ is H;

M is selected from borate esters and boric acids, including but not limited to 4,4,5,5-tetramethyl-1,3,2-dioxaborolane, bis(neopentyl glycolato)diboron, 4,4,4',4',5,5,5',5'-octamethyl-2,2'-di(1,3,2-dioxaborolane)B(OBu-n)$_3$, and B(OPr-i)$_3$; or, M is selected from bromine, iodine, chlorine and $CF_3SO_3$-(OTf);

W is selected from borate esters and boric acids, including but not limited to 4,4,5,5-tetramethyl-1,3,2-dioxaborolane, bis(neopentyl glycolato)diboron, 4,4,4',4',5,5,5', 5'-octamethyl-2,2'-di(1,3,2-dioxaborolane)B(OBu-n)$_3$, and B(OPr-i)$_3$; or, W is selected from bromine, iodine, chlorine and $CF_3SO_3$-(OTf);

$P^1$ and $P^2$ are protecting groups, which can be identically or differently selected from Boc (tert-butyloxy carbonyl), Fmoc (9-fluorene methoxycarbonyl), Cbz (N-benzyloxyl carbonyl), methosulfonyl, p-toluene sulfonyl, acetyl, methoxy carbonyl, ethoxy carbonyl, ((2-trimethylsilicon) ethoxy) methyl (SEM), and tetrahydro-2H-pyran-2-yl (THP).

In some embodiments, the first acid includes but is not limited to trifluoroacetic acid (TFA), hydrochloric acid (HC$_1$), acetic acid (HOAc), and hydrobromic acid (HBr);

The first alkali includes but is not limited to piperidine and diethylamine;

The first solvent includes but is not limited to dichloromethane (DCM), 1,2-dichloroethane, methanol (MeOH), ethanol (EtOH), 1,4-dioxane, tetrahydrofuran (THF), acetonitrile (MeCN), and N, N'-dimethylformamide (DMF).

In some embodiments, the first catalyst includes but is not limited to 1,1'-bis (dicyclohexylphosphino)ferrocene dichloropalladium (PdCl$_2$(dcypf)), palladium acetate (Pd(OAc)$_2$), palladium dichloride (PdCl$_2$), tris(dibenzylidene acetone) dipalladium (Pd$_2$(dba)$_3$), [1,1'-bis(diphenylphino)ferrocene] palladium dichloride (PdCl$_2$(dppf)), [1,1'-bis(diphenylphino)ferrocene] palladium dichloride dichloromethane complex (PdCl$_2$(dppf) CH$_2$Cl$_2$), tetrad (triphenylphosphine) palladium (Pd(PPh$_3$)$_4$), Bis (tricyclohexyl phosphine) palladium dichloride (PdCl$_2$(P(Cy)$_3$)$_2$), and 2-dicyclohexylphosphino-2',6'-dimethoxybiphenyl (SPhos);

The second alkali includes organic alkalis and inorganic alkalis, such as triethylamine (TEA), N,N-diisopropylethylamine (DIPEA), n-butyl lithium, lithium diisopropylamide, lithium bis(trimethylsilyl)amide, potassium acetate (KOAc), sodium tert-butoxide (NaOBu-t), potassium tert-butoxide (KOBu-t), sodium hydride (NaH), potassium phosphate (K$_3$PO$_4$), sodium carbonate (Na$_2$CO$_3$), potassium carbonate (K$_2$CO$_3$), potassium hydroxide (KOH), and sodium hydroxide (NaOH);

The second solvent includes but is not limited to 1,4-dioxane, THF, MeCN, DMF, and mixtures of each of these solvents with water in different ratios.

In some embodiments, the first reducing agent and the second reducing agent include but are not limited to sodium triacetoxyborohydride, sodium borohydride, and sodium cyanoborohydride;

The third and fourth solvents include but are not limited to DCM, 1,2-dichloroethane, MeOH, EtOH, 1,4-dioxane, THF, MeCN, and DMF.

In some embodiments, the third alkali includes but is not limited to lithium hydroxide (LiOH), potassium hydroxide (KOH), and sodium hydroxide (NaOH).

Specifically, the compound of formula (I-a) is deprotected in an appropriate solvent by using an appropriate acid, alkali or catalytic hydrogenolysis to remove the protecting group P$^1$. The resulting product without being separated or purified further has a Suzuki reaction with the compound of formula (I-b) in an appropriate solvent under an appropriate alkaline condition in the presence of a catalyst to obtain the compound of formula (I-c). The appropriate solvent for deprotection includes but is not limited to DCM, 1,2-dichloroethane, MeOH, EtOH, 1,4-dioxane, THF, MeCN, and DMF. The acid includes but is not limited to trifluoroacetic acid (TFA), hydrochloric acid (HCl), acetic acid (HOAc), hydrobromic acid (HBr). The alkali includes but is not limited to piperidine and diethylamine. The catalyst includes but is not limited to 1,1'-bis (dicyclohexylphosphino)ferrocene dichloropalladium (PdCl$_2$(dcypf)), palladium acetate (Pd (OAc)$_2$), palladium dichloride (PdCl$_2$), tris(dibenzylidene acetone)dipalladium (Pd$_2$(dba)$_3$), [1,1'-bis(diphenylphino)ferrocene]palladium dichloride (PdCl$_2$(dppf)), [1,1'-bis(diphenylphino)ferrocene]palladium dichloride dichloromethane complex (PdCl$_2$(dppf)·CH$_2$Cl$_2$), tetrad (triphenylphosphine) palladium (Pd(PPh$_3$)$_4$), Bis (tricyclohexyl phosphine) palladium dichloride (PdCl$_2$(P(Cy)$_3$)$_2$), and 2-dicyclohexylphosphino-2',6'-dimethoxybiphenyl (SPhos). The reagent forming the alkali condition includes organic alkalis and inorganic alkalis, including but not limited to TEA, DIPEA, n-butyl lithium, lithium diisopropylamide, lithium bis(trimethylsilyl)amide, KOAc, NaOBu-t, KOBu-t, NaH, K$_3$PO$_4$, Na$_2$CO$_3$, K$_2$CO$_3$, KOH, and NaOH. The reagent for the Suzuki reaction includes but is not limited to 1,4-dioxane, THF, MeCN, DMF, and mixtures of each of these solvents with water in different ratios.

The compound of formula (I-c) and the compound of formula (I-d) have reductive amination in an appropriate solvent in the presence of a reducing agent to obtain the compound of formula (I-e). The reducing agent includes but is not limited to sodium triacetoxyborohydride, sodium borohydride, and sodium cyanoborohydride. The solvent includes but is not limited to DCM, 1,2-dichloroethane, MeOH, EtOH, 1,4-dioxane, THF, MeCN, and DMF.

The compound of formula (I-e) is deprotected in an appropriate solvent by using an appropriate acid, alkali or catalytic hydrogenolysis to remove a protecting group P$^2$. The resulting product without being separated or purified further has a reductive amination with the compound of formula (I-f) in an appropriate solvent in the presence of a reducing agent to obtain the compound of formula (I'). The acid includes but is not limited to TFA, HCl, HOAc, and HBr. The alkali includes but is not limited to piperidine and diethylamine. The reducing agent includes but is not limited to sodium triacetoxyborohydride, sodium borohydride, and sodium cyanoborohydride. The solvent includes but is not limited to DCM, 1,2-dichloroethane, MeOH, EtOH, 1,4-dioxane, THF, MeCN, and DMF.

The compound of formula (I') can be used as the final product of formula (I). In addition, the compound of formula (I') can further have ester hydrolysis under an alkaline condition to obtain the compound of formula (I''), which can also be used as the final product of formula (I). The alkali includes but is not limited to lithium hydroxide (LiOH), potassium hydroxide (KOH), and sodium hydroxide (NaOH);

M is selected from borate esters and boric acids, including but not limited to 4,4,5,5-tetramethyl-1,3,2-dioxaborolane, bis(neopentyl glycolato)diboron, 4,4,4',4',5,5,5', 5'-octamethyl-2,2'-di(1,3,2-dioxaborolane)B(OBu-n)$_3$, and B(OPr-i)$_3$; or, M is selected from bromine, iodine, chlorine and CF$_3$SO$_3$-(OTf); W is selected from borate esters and boric acids, including but not limited to 4,4,5,5-tetramethyl-1,3,2-dioxaborolane, bis(neopentyl glycolato)diboron, 4,4,4', 4',5,5,5',5'-octamethyl-2,2'-di(1,3,2-dioxaborolane)B (OBu-n)$_3$, and B(OPr-i)$_3$; or, W is selected from bromine, iodine, chlorine and CF$_3$SO$_3$-(OTf); P$^1$ and P$^2$ are protecting groups, which can be identically or differently selected from Boc (tert-butyloxy carbonyl), Fmoc (9-fluorene methoxycarbonyl), Cbz (N-benzyloxyl carbonyl), methosulfonyl, p-toluene sulfonyl, acetyl, methoxy carbonyl, ethoxy carbonyl, ((2-trimethylsilicon) ethoxy) methyl (SEM), and tetrahydro-2H-pyran-2-yl (THP).

This disclosure further provides another preparation method of the compound of formula (I), comprising the following steps:

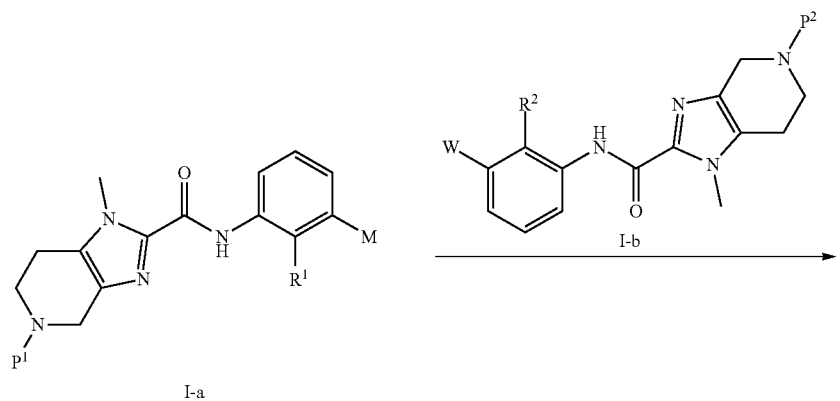
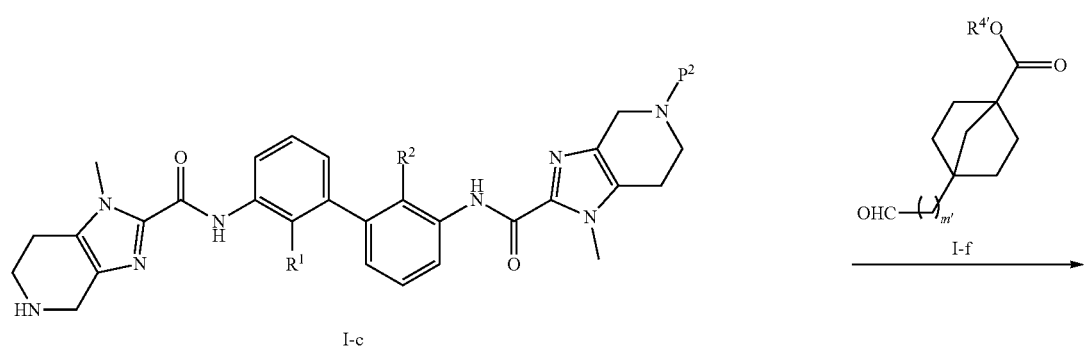
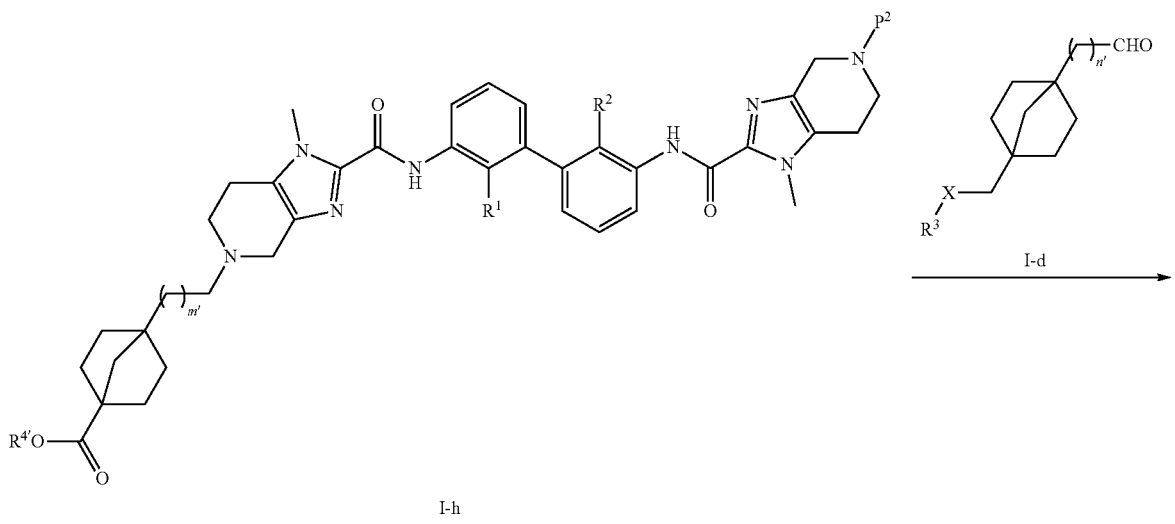

-continued

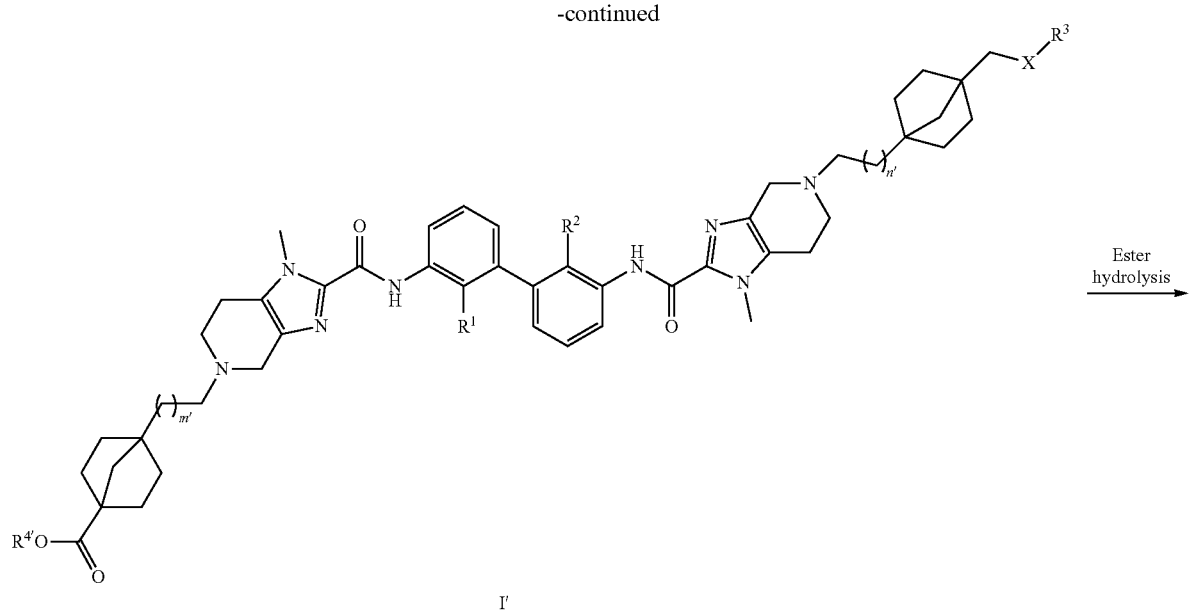

I'

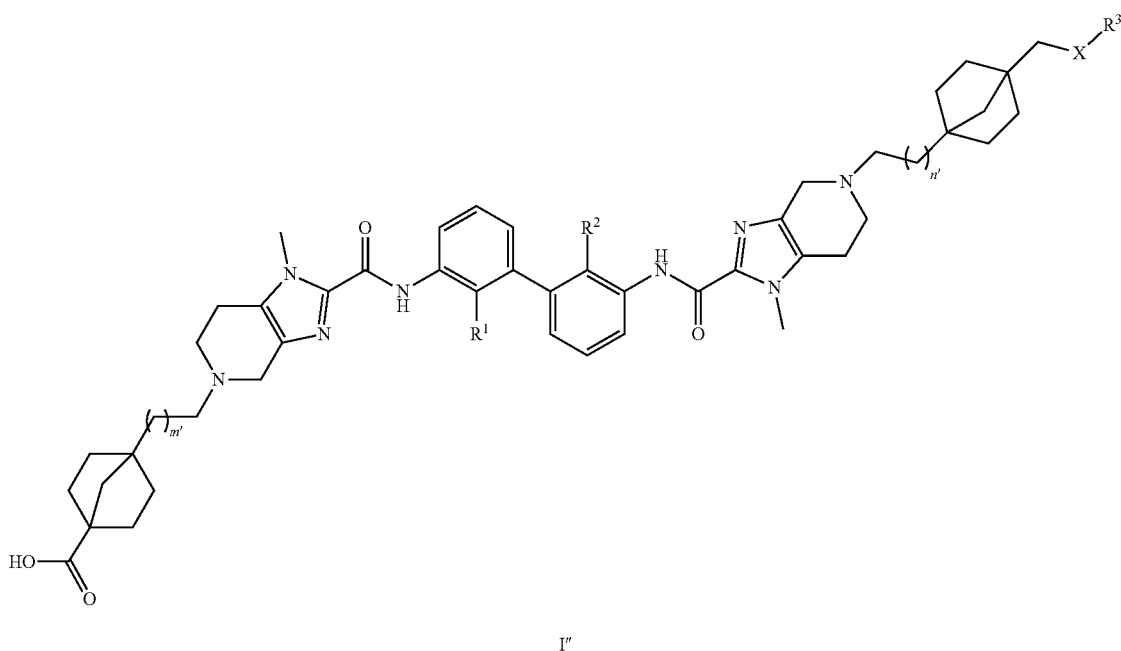

I"

1) deprotecting a compound of (I-a) in a first solvent by using a first acid, a first alkali or catalytic hydrogenolysis to remove a protecting group $P^1$, and allowing the resulting product without being separated or purified to further have a Suzuki reaction with a compound of formula (I-b) in a second solvent in the presence of a first catalyst and a second alkali to obtain a compound of formula (I-c);
2) allowing the compound of formula (I-c) and a compound of formula (I-f) to have reductive amination in a fourth solvent in the presence of a second reducing agent to obtain a compound of formula (I-h);
3) allowing the compound of formula (I-h) and a compound of formula (I-d) to have reductive amination in a third solvent in the presence of a first reducing agent to obtain a compound of formula (I'); and optionally, further comprising 4), allowing the compound of formula (I') to have ester hydrolysis in the presence of a third alkali to obtain a compound of formula (I").

The compound of formula (I') can be used as the final product of formula (I). In addition, the compound of formula (I') can further have ester hydrolysis under an alkaline condition to obtain the compound of formula (I"), which can also be used as the final product of formula (I).

Wherein

X, $R^1$, $R^2$, and $R^3$ are defined as above;

m', n', $R^{4'}$, M, W, $P^1$ and $P^2$ are defined as above;

The first acid, the first alkali and the first solvent are described as above;

The first catalyst, the second alkali and the second solvent are described as above;

The first reducing agent, the second reducing agent and, the third solvent and the fourth solvent are described as above;

The third alkali is described as above.

Specifically, the preparation method of the compound in this disclosure can further comprise: deprotecting the compound of (I-a) to remove a protecting group P', and allowing the resulting product without being separated or purified to further have the above-described Suzuki with the compound of formula (I-b) to obtain the compound of formula (I-c); allowing the compound of formula (I-c) and the compound of formula (I-f) to have the above-described reductive amination to obtain a compound of formula (I-h); and deprotecting the compound of formula (I-h) and then allowing the deprotected compound to have the above-described reductive amination with the compound of formula (I-d) to obtain the compound of formula (I'); or optionally, further carrying out the above-described ester hydrolysis to obtain the compound of formula (I"). Each substituent is defined as above. The compound of formula (I') and the compound of formula (I") can be used as the final product of formula (I).

This disclosure further provides another preparation method of the compound of formula (I), comprising the following step:

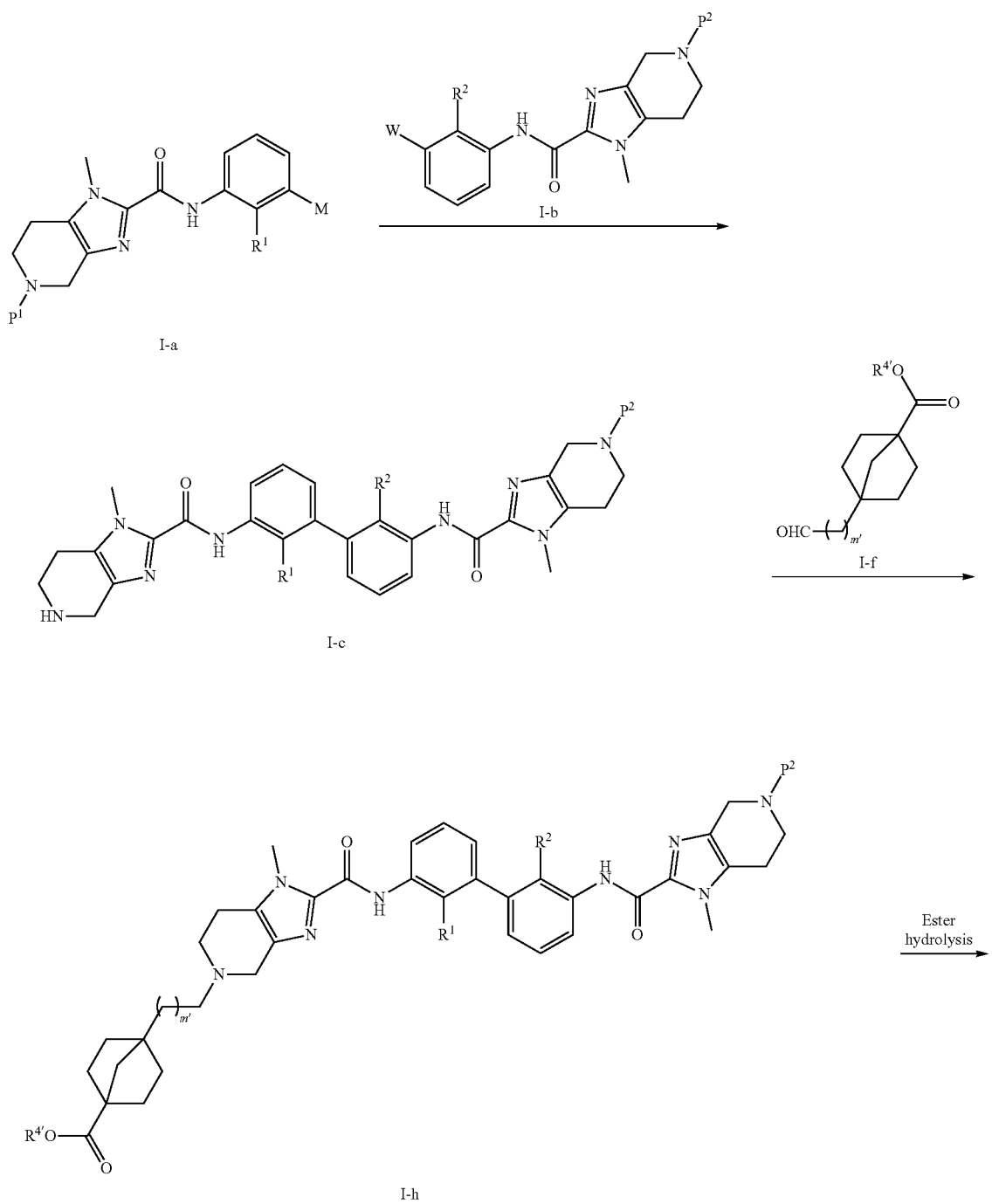

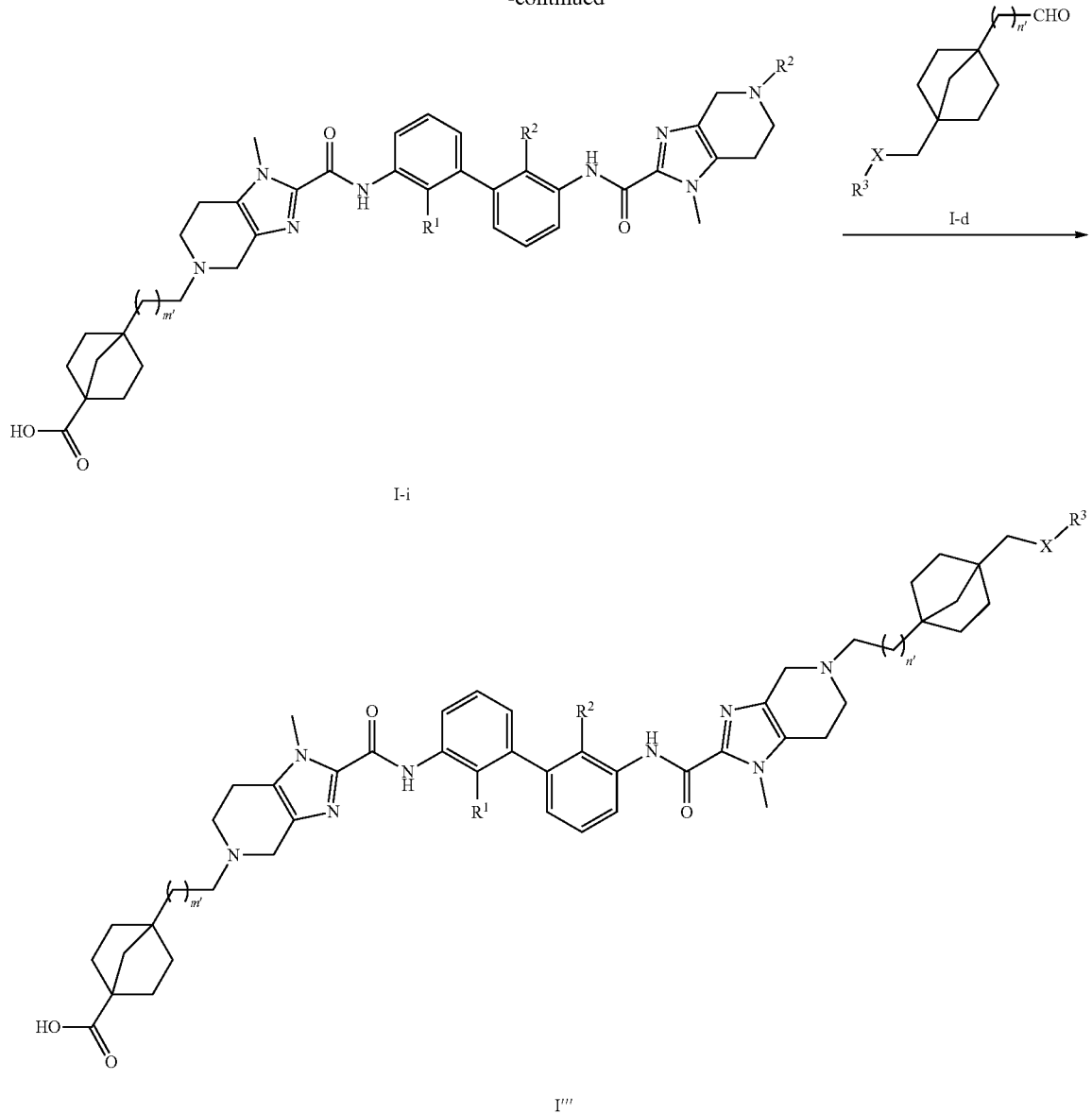

1) deprotecting a compound of (I-a) in a first solvent by using a first acid, a first alkali or catalytic hydrogenolysis to remove a protecting group P¹, and allowing the resulting product without being separated or purified to further have a Suzuki reaction with a compound of formula (I-b) in a second solvent in the presence of a first catalyst and a second alkali to obtain a compound of formula (I-c);
2) allowing the compound of formula (I-c) and a compound of formula (I-f) to have reductive amination in a fourth solvent in the presence of a second reducing agent to obtain a compound of formula (I-h); and
3) allowing the compound of formula (I-h) to have ester hydrolysis in the presence of a third alkali to obtain a compound of formula (I-i).
4) allowing the compound of formula (I-i) and a compound of formula (I-d) to have reductive amination in a third solvent in the presence of a first reducing agent to obtain a compound of formula (I''');

The compound of formula (I') can be used as the final product of formula (I).

Wherein:

X, R¹, R², and R³ are defined as above;

m', n', R⁴', M, W, P¹ and P² are defined as above;

The first acid, the first alkali and the first solvent are described as above;

The first catalyst, the second alkali and the second solvent are described as above;

The first reducing agent, the second reducing agent, the third solvent and the fourth solvent are described as above;

The third alkali is described as above.

Specifically, the preparation method of the compound in this disclosure can further comprise: deprotecting the compound of (I-a) to remove a protecting group Pi, and allowing the resulting product without being separated or purified to further have the above-described Suzuki with the compound of formula (I-b) to obtain the compound of formula (I-c); allowing the compound of formula (I-c) and the compound of formula (I-f) to have the above-described reductive amination to obtain a compound of formula (I-h); then allowing the compound of formula (I-h) to have the above-described ester hydrolysis to obtain the compound of formula (I-i); further deprotecting the compound of formula (I-i) and then allowing the deprotected compound to have the above-described reductive amination with the compound of formula (I-d) to obtain the compound of formula (I′′′). Each substituent is defined as above. The compound of formula (I′) can be used as the final product of formula (I).

In addition, this disclosure provides use of the compound or its stereoisomers, pharmaceutically acceptable salts, precursors and metabolites or the pharmaceutical composition in preparation of a drug for treatment and/or prevention of diseases related to a target PD-L1, or
- a drug for inhibiting the activity of PD-L1, or
- a drug as a PD-L1 inhibitor, or
- a drug as an immunomodulator for targeting a PD-L1 signaling pathway.

In some embodiments, the diseases related to the target PD-L1 include tumors, cancers, or other immune-related diseases.

In another respect, this disclosure provides the compound or its stereoisomers, pharmaceutically acceptable salts, precursors and metabolites or the pharmaceutical composition for use in treatment and/or prevention of diseases related to a target PD-L1, or
- for use in inhibiting the activity of PD-L1, or
- for use as a PD-L1 inhibitor, or
- for use as an immunomodulator for targeting a PD-L1 signaling pathway.

In some embodiments, the diseases related to the target PD-L1 include tumors, cancers, or other immune-related diseases.

In another respect, this disclosure provides a method for treatment and/or prevention of diseases related to a target PD-L1, including administration of a prophylactically and/or therapeutically effective dose of the compound or its stereoisomers, pharmaceutically acceptable salts, precursors and metabolites or the pharmaceutical composition to subjects in need thereof.

This disclosure provides a method for inhibiting the activity of PD-L1, including administration of a therapeutically effective dose of the compound or its stereoisomers, pharmaceutically acceptable salts, precursors and metabolites or the pharmaceutical composition to cells (e.g. mammalian cells).

In some embodiments, the diseases related to the target PD-L1 include tumors, cancers, or other immune-related diseases.

In this disclosure, the term "subjects" refers to vertebrates. In some embodiments, the vertebrates are mammals. The mammals include bovines, equines, ovines, swines, canines, felines, rodents, primates, such as humans, cats, dogs, or pigs. The mammals include, but are not limited to, livestock (such as cattle), pets (such as cats, dogs, and horses), primates, mice and rats. In some embodiments, the mammals refer to humans.

In this disclosure, the term "therapeutically effective dose" or "prophylactically effective dose" means a dose that is sufficient, within reasonable medical determination, to treat or prevent a patient's disease but low enough to avoid serious side effects (at a reasonable benefit/risk ratio). The therapeutically effective dose of a compound varies according to a specific compound chosen (for example, in consideration of the potency, effectiveness, and half-life of the compound), an administration route chosen, a disease to be treated, the severity of the disease to be treated, the age, size, weight and physical disease of a patient to be treated, the medical history and duration of treatment of the patient to be treated, the nature of the concurrent therapy, the desired therapeutic effect and other factors, but can still be routinely determined by those skilled in the art.

It also should be noted that the specific administration dose and method of the compound or its stereoisomers, pharmaceutically acceptable salts, precursors and metabolites for different patients depend on many factors, including the patient's age, weight, gender, natural health, nutritional status, the activity intensity, administration time, and metabolic rate of drug, the severity of the disease and the subjective determination of the treating physician. The preferred dose herein is between 0.001 mg/kg and 1000 mg/kg (body weight)/day.

This disclosure provides a novel small-molecule biphenyl immune inhibitor with excellent oral absorption characteristics for the treatment or prevention of immune-related diseases. Moreover, these compounds or pharmaceutical compositions containing them as active ingredients or the like can maximize the clinical efficacy of these diseases in a safe therapeutic window.

DETAILED DESCRIPTION

Figure 1:
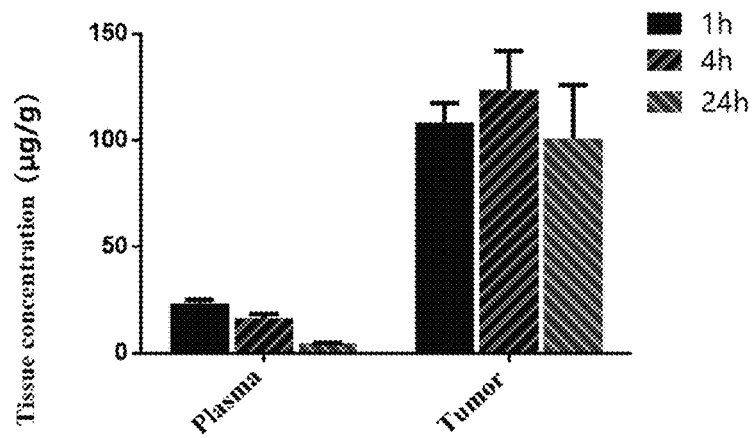
FIG. 1 shows plasma and tumor tissue distribution of example compound I-6.

Examples and preparation examples disclosed in this disclosure further clarify and exemplify the compound and its preparation method. It should be understood that the following preparation examples and examples do not in any way limit the scope of this disclosure.

LC-MS analysis method:

Mass spectrometry conditions: Device: Thermo MSQ Plus; ion source: ESI (EA+EA−); Cone voltage: 30 V; capillary voltage: 3.00 KV; source temperature: 350° C.;

Chromatogram conditions: Device: Thermo U3000; detector: DAD-3000 (RS) (diode array detector); column: Shimadzu Inertsil ODS-HL HP 3 μM 3.0×100 mm; flow rate: 0.4 mL/min; column temperature: 30° C.; mobile phase: $CH_3OH/H_2O/HCOOH$ (75/25/0.2).

HPLC Analysis method (I):

Device: Thermo U3000; detector: VWD-3×00 (RS) (UV detector); column: Shimadu Shim-pack VP-ODS 5 μm 4.6× 150 mm; flow rate: 1.0 mL/min; column temperature: 30° C.; Mobile phase A: $CH_3OH/H_2O/TEA/HOAc$ (65/35/0.2/0.1).

HPLC Analysis method (II):

Device: Thermo U3000; detector: VWD-3×00 (RS) (UV detector); column: Shimadu Shim-pack VP-ODS 5 μm 4.6× 150 mm; flow rate: 1.0 mL/min; column temperature: 30° C.; Mobile phase B: $CH_3OH/H_2/TEA/HOAc$ (80/20/0.2/0.1).

$^1$H-NMR analysis method:

$^1$H-NMR is carried out by BRUKER AVANCE-400 MHz NMR spectrometer in DMSO-$d_6$ or $CDCl_3$ at room temperature with TMS as internal standard substance. The signal peaks are expressed as s (single peak), d (double peak), t (triple peak), q (quadruple peak), m (multiple peak), and dd (double double peak). The unit of coupling constant (J) is Hertz (Hz).

Key Abbreviations:

| | | | |
|---|---|---|---|
| 1,4-dioxane | 1,4-dioxane | DCM | Dichloromethane |
| MeOH | Methanol | EtOAc | Ethyl acetate |
| TEA | Triethylamine | DIPEA | N,N'-diisopropylethylamine |
| TFA | Trifluoroacetic acid | THF | Tetrahydrofuran |
| $NaHCO_3$ | Sodium bicarbonate | $Na_2SO_4$ | Sodium sulfate |
| $NaBH(OAc)_3$ | Sodium triacetoxyborohydride | $LiOH \cdot H_2O$ | Lithium hydroxide hydrate |
| $PdCl_2(dcypf)$ | 1,1'-bis (dicyclohexylphosphino)ferrocene dichloropalladium | | |
| TLC | Thin-layer chromatography | | |

Representative compounds such as compounds I-1 to I-12 are prepared in accordance with the above described methods (see Table 1).

TABLE 1

Representative compounds I-1 to I-12 in this disclosure

| Compound number (Example) | % purity (HPLC) | Retention time (min) | Detection wavelength (nm) | Analysis method |
|---|---|---|---|---|
| I-1 | 98.5 | 23.70 | 297 | (II) |
| I-2 | 97.6 | 22.30 | 297 | (II) |
| I-3 | 99.7 | 23.59 | 254 | (II) |
| I-4 | 96.9 | 16.35 | 254 | (II) |
| I-5 | 98.7 | 9.37 | 286 | (II) |
| I-6 | 98.4 | 12.65 | 286 | (II) |
| I-7 | 93.4 | 12.05 | 254 | (II) |
| I-8 | 96.0 | 7.71 | 230 | (I) |
| I-9 | 97.7 | 18.03 | 254 | (II) |
| I-10 | 96.5 | 9.88 | 254 | (II) |
| I-11 | 90.4 | 6.79 | 254 | (II) |
| I-12 | 99.6 | 8.60 | 297 | (II) |

The content of this disclosure is further described in combination with specific examples, but the scope of this disclosure is not limited to these examples. The percentages set forth in this disclosure are percentages by weight, unless otherwise specified. The ranges of values described in the description, such as unit of measurement, reaction conditions, physical state or percentage of compounds, are intended to provide clear and correct written reference. When a person skilled in the art implements this disclosure, it is still possible to obtain expected results by using temperatures, concentrations, numbers, carbon atoms, etc. that are outside the ranges or different from single values. In addition, the raw materials in the following examples can be purchased commercially unless otherwise specified, for example, they can be purchased from Shanghai Bide Pharmaceutical Technology Co., Ltd., Jiangsu Aikon Biomedical Research and Development Co., Ltd., Nanjing Pharma Block Technology Co., Ltd., Shanghai Accela ChemBio Co. Ltd., and HCH Biotechnology (Shanghai) Co., Ltd.

Example 1

Preparation of Compound I-1: 4-(2-(2-((2'-chloro-3'-(5-(3-(4-(methoxymethyl)bicyclo[2.2.1]heptan-1-yl)propyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic Acid

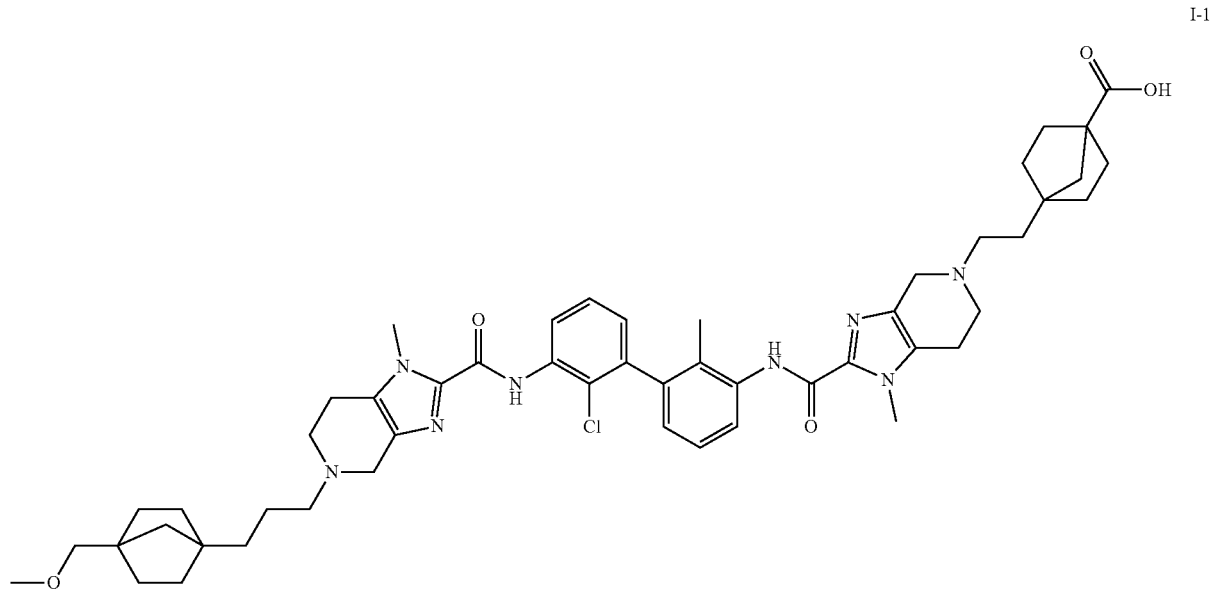 [SMILES: COCC12CCC(CCCN3CCc4c(nc(C(=O)Nc5cccc(-c6cccc(NC(=O)c7nc8c(n7C)CCN(CCC79CCC(C(=O)O)(CC7)C9)C8)c6C)c5Cl)n4C)C3)(CC1)C2]

I-1

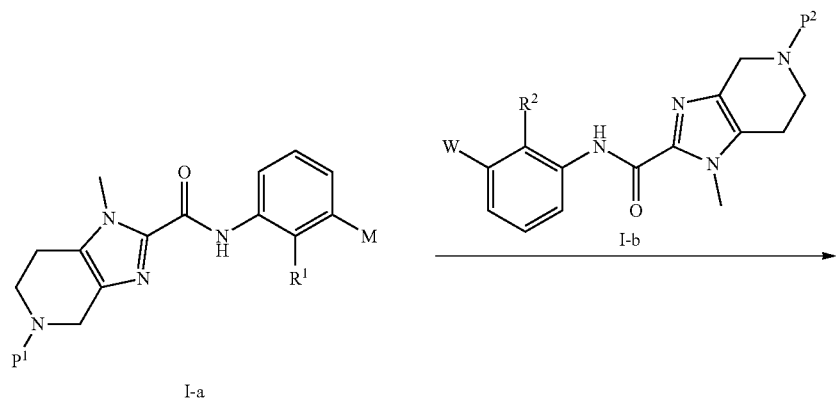
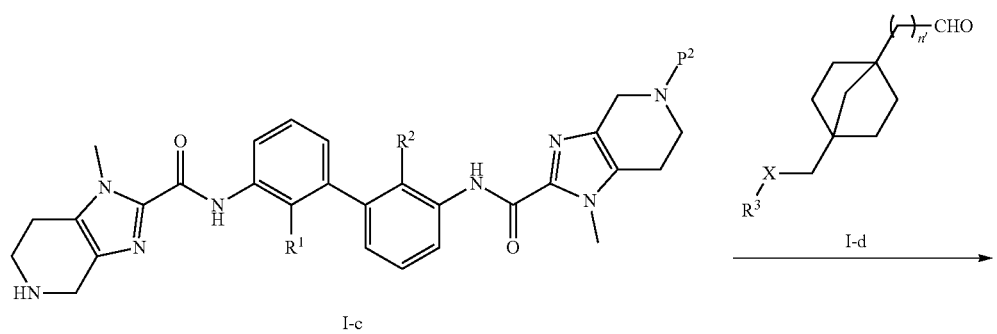
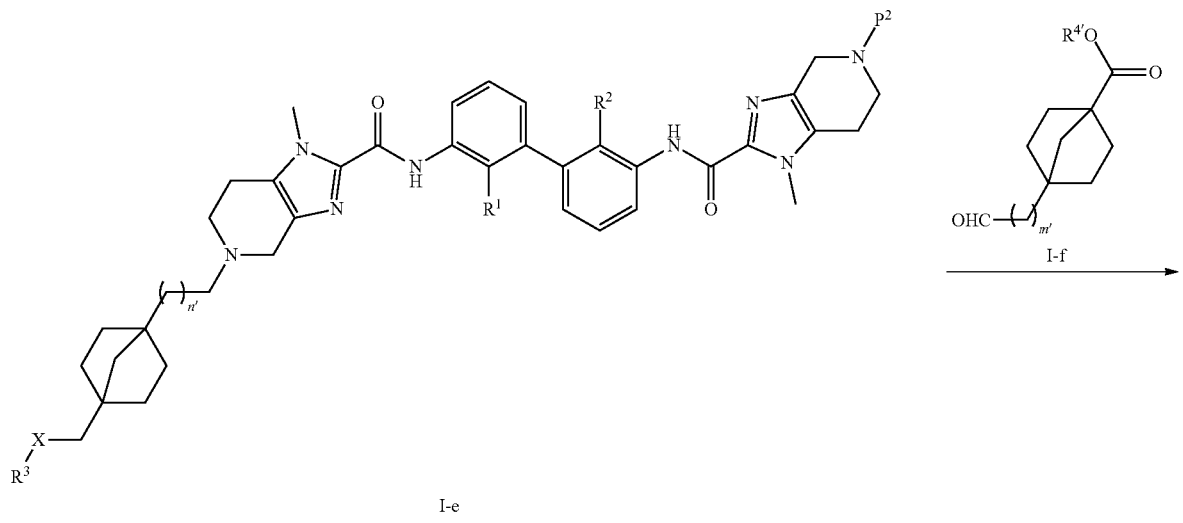

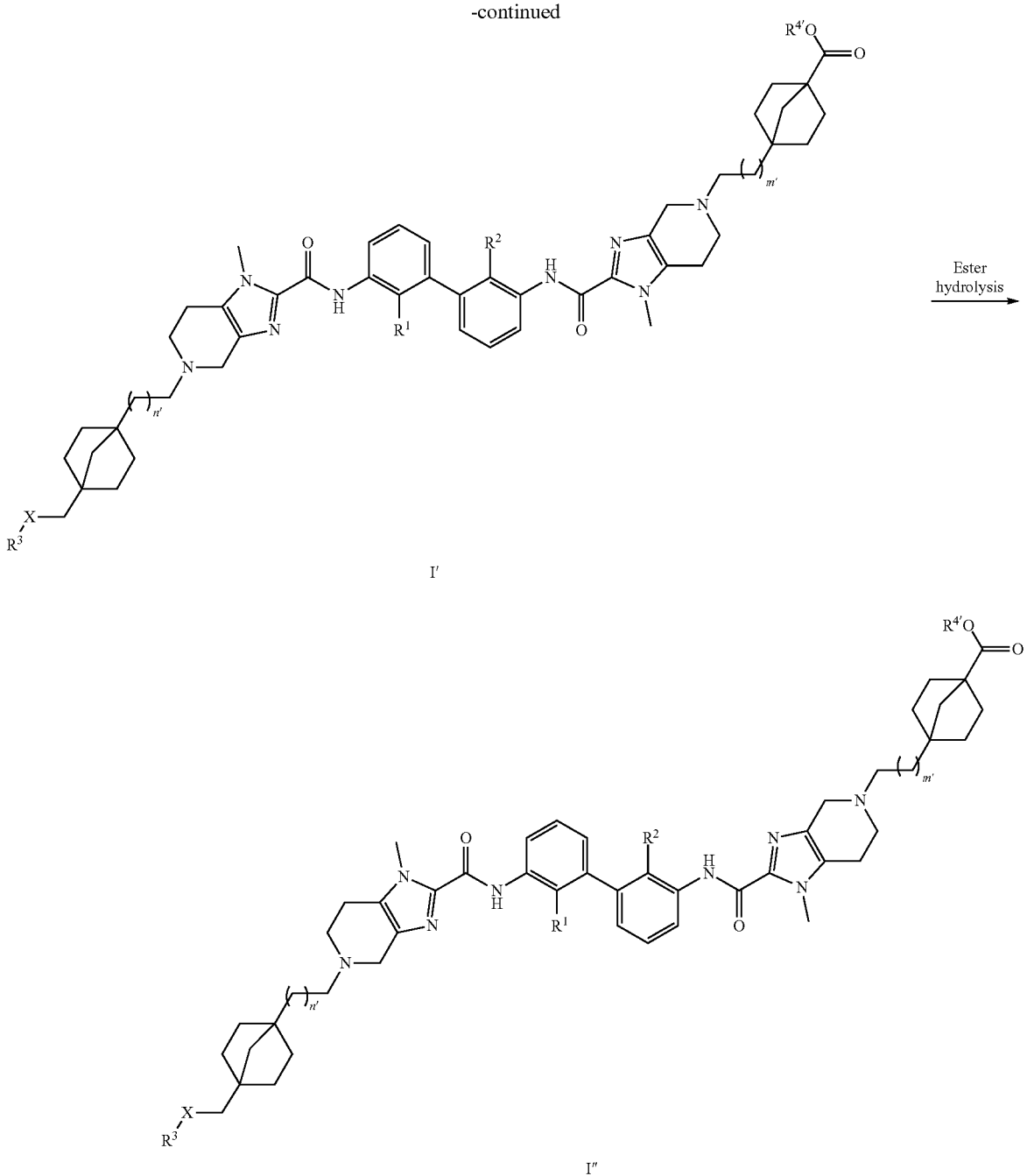

Preparation of intermediate I-1c: 2-((2'-chloro-2-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylic Acid tert-butyl ester 2-((3-bromo-2-chlorophenyl)carbamoyl)-1-methyl-1,4,6,7-tetrahydro-5H-imidazo[4,5-c]pyridine-5-carboxylic acid tert-butyl ester I-1a (1.18 g, 2.52 mmol, 1.0 eq, synthesis by referring to CN202010997428.3) was dissolved in DCM (10 mL) and then TFA (10 mL) was added, the mixed solution was stirred at ambient temperature for 1 h. The reaction solution was concentrated, and the residue was dissolved in 1,4-dioxane (10 mL); 1-methyl-2-((2-methyl-3-(4,4,5,5-tetramethyl-1,3,2-dioxaborolan-2-yl) phenyl)carbamoyl)-1,4,6,7-tetrahydro-5H-imidazo[4,5-c]pyridine-5-carboxylic acid tert-butyl ester I-1b (1.25 g, 2.52 mmol, 1.0 eq, synthesis by referring to CN202010997428.3), PdCl$_2$(dcypf) (188.75 mg, 0.25 mmol, 0.1 eq), anhydrous Na$_2$CO$_3$ (801.36 mg, 7.56 mmol, 3.0 eq) and water (5 mL) were added; the resulting mixture was heated to 110° C. by microwave and reacted for 1 h, and then cooled to ambient temperature. The reaction solution was concentrated, and the crude product was separated by silica gel column chromatography (DCM/MeOH (v/v)=15/1) to obtain a pale yellow solid I-1c. (1.08 g, with a yield of 65.1%). LC-MS MS-ESI (m/z) 659.2 [M+H]$^+$.

Preparation of intermediate I-1e: 2-((2'-chloro-3'-(5-(3-(4-(methoxymethyl)bicyclo[2.2.1]heptan-1-yl)propyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridine-5-carboxylic Acid tert-butyl ester Intermediate I-1c (132.00 mg, 0.20 mmol, 1.0 eq) was dissolved in DCM (10 mL), TEA (1 mL) and 2-(4-(methoxymethyl)bicyclo[2.2.1]heptan-1-yl)acetaldehyde I-1d (43.20 mg, 0.22 mmol, 1.1 eq, synthesis by referring to CN202010997428.3) were added; the mixed solution was stirred at ambient temperature for 1 h; NaBH(OAc)₃ (212.00 mg, 1.00 mmol, 5.0 eq) was added and further stirred for 16 h. The reaction solution was quenched with saturated NaHCO₃ solution, extracted with DCM/MeOH (10/1, 100 mL) three times, and the organic phases were combined, dried with anhydrous Na₂SO₄, and concentrated. The crude product was isolated by preparative TLC (DCM/MeOH (v/v)=8/1) to obtain a pale yellow solid I-1e. (115.00 mg, with a yield of 68.5%). LC-MS MS-ESI (m/z) 839.5 [M+H]⁺.

Preparation of Intermediate I-1g: 4-(2-(2-((2'-chloro-3'-(5-(3-(4-(methoxymethyl)bicyclo[2.2.1]heptan-1-yl)propyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid methyl ester Intermediate I-1e (115.00 mg, 0.13 mmol, 1.0 eq) was dissolved in DCM (10 mL) and then TFA (10 mL) was added; the mixed solution was stirred at ambient temperature for 1 h. The reaction solution was concentrated, and the residue was dissolved in DCM (10 mL); the solution was concentrated again, and the resulting yellow solid was used directly in the next step. Trifluoroacetate was dissolved in DCM (10 mL), then TEA (1 mL) and commercially available 4-(2-oxoethyl)bicyclo[2.2.1]heptane-1-carboxylic acid methyl ester I-1f (29.56 mg, 0.15 mmol, 1.1 eq) were added. The mixed solution was stirred at ambient temperature for 1 h; NaBH(OAc)₃ (145.22 mg, 0.68 mmol, 5.0 eq) was added and further stirred for 16 h. The reaction solution was quenched with saturated NaHCO₃ solution, extracted with DCM/MeOH (10/1, 100 mL) three times, and the organic phases were combined, dried with anhydrous Na₂SO₄, and concentrated. The crude product was isolated by preparative TLC (DCM/MeOH (v/v)=6/1) to obtain I-1g. (86.00 mg, with a yield of 68.2%). LC-MS MS-ESI (m/z) 919.6 [M+H]+.

Preparation of Compound I-1: 4-(2-(2-((2'-chloro-3'-(5-(3-(4-(methoxymethyl)bicyclo[2.2.1]heptan-1-yl)propyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic Acid Intermediate I-1g (86.00 mg, 0.09 mmol, 1.0 eq) was dissolved in THF (10 mL), water (10 mL) and LiOH·H₂O (75.60 mg, 1.80 mmol, 20.0 eq) were then added. The mixed solution was stirred at ambient temperature for 16 h. The obtained solution was concentrated to remove THF, adjusted to pH of 5-6 with 1M of hydrochloric acid. The solid was collected by filtration, and dried to obtain a yellow solid I-1. (56.00 mg, with a yield of 66.1%). LC-MS MS-ESI (m/z) 905.6 [M+H]+. ¹H-NMR (400 MHz, DMSO-d₆) δ ppm 9.90 (s, 1H), 9.74 (s, 1H), 8.34 (d, J=8.3 Hz, 1H), 7.72 (d, J=8.1 Hz, 1H), 7.46 (t, J=7.9 Hz, 1H), 7.30 (t, J=7.8 Hz, 1H), 7.07 (d, J=7.6 Hz, 1H), 7.01 (d, J=7.4 Hz, 1H), 3.90 (s, 3H), 3.87 (s, 3H), 3.41-3.38 (m, 4H), 3.33 (s, 2H), 3.23 (s, 3H), 2.81-2.70 (m, 4H), 2.70-2.61 (m, 4H), 2.58-2.43 (m, 4H), 1.99 (s, 3H), 1.88-1.79 (m, 2H), 1.74-1.65 (m, 2H), 1.57-1.20 (m, 20H), 1.08 (s, 2H).

Example 2

4-(2-(2-((2-chloro-3'-(5-(3-(4-(methoxymethyl)bicyclo[2.2.1]heptan-1-yl)propyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid I-2

I-2

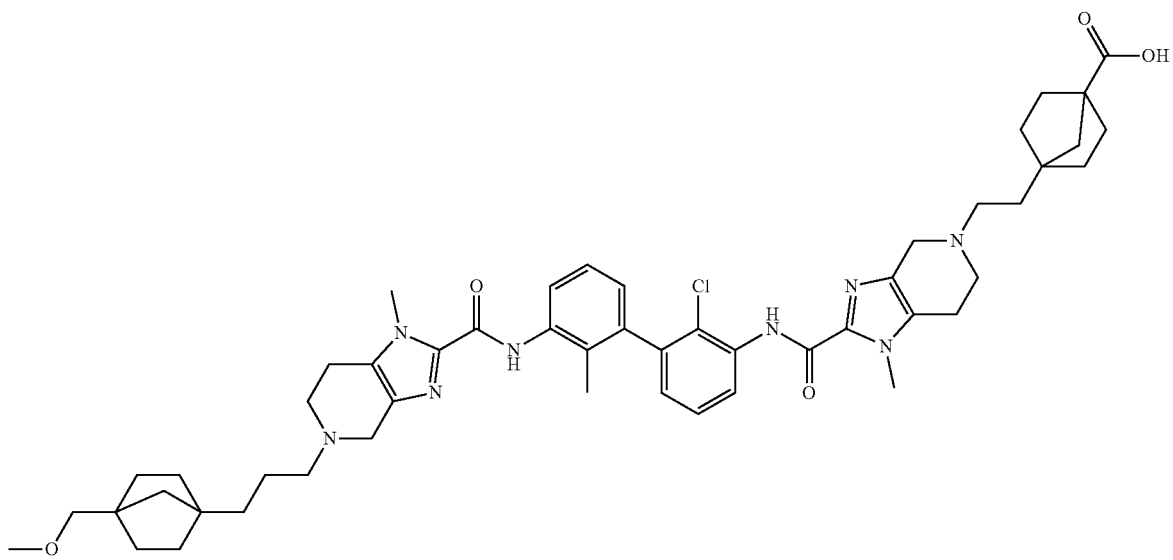

Preparation of Intermediate I-1h: 2-((2'-chloro-3'-(5-(2-(4-(methoxycarbonyl)bicyclo[2.2.1]heptan-1-yl)ethyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridine-5-carboxylic Acid tert-butyl ester Intermediate I-1h was prepared from intermediate I-1c (720.00 mg, 1.09 mmol, 1.0 eq), TEA (1 mL), 4-(2-oxoethyl)bicyclo[2.2.1]heptane-1-carboxylic acid methyl ester I-1f (320.46 mg, 1.63 mmol, 1.5 eq) and NaBH(OAc)$_3$ (1.39 g, 6.54 mmol, 6.0 eq) according to the steps similar to those in intermediate I-1e. (563.00 mg, with a yield of 61.5%). LC-MS MS-ESI (m/z) 839.4 [M+H]+.

Preparation of Intermediate I-2g: 4-(2-(2-((2-chloro-3'-(5-(3-(4-(methoxymethyl)bicyclo[ 2.2.1]heptan-1-yl)propyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic Acid methyl ester Intermediate I-2g was prepared from intermediate I-1h (95.00 mg, 0.11 mmol, 1.0 eq), TFA (5 mL), TEA (1 mL), 2-(4-(methoxymethyl)bicyclo[2.2.1]heptan-1-yl)acetaldehyde I-1d (24.42 mg, 0.12 mmol, 1.1 eq) and NaBH(OAc)$_3$ (120.00 mg, 0.56 mmol, 5.0 eq) according to the steps similar to those in intermediate I-1g. (75.00 mg, with a yield of 72.1%). LC-MS MS-ESI (m/z) 919.5 [M+H]+.

Preparation of Compound I-2: 4-(2-(2-((2-chloro-3'-(5-(3-(4-(methoxymethyl)bicyclo[2.2.1]heptan-1-yl)propyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic Acid White solid I-2 was prepared from intermediate I-2g (75.00 mg, 0.08 mmol, 1.0 eq) and LiOH·H$_2$O (67.20 mg, 1.60 mmol, 20.0 eq) according to the steps similar to those in Compound I-1. (27.00 mg, with a yield of 36.5%). LC-MS MS-ESI (m/z) 905.6 [M+H]+. $^1$H-NMR (400 MHz, DMSO-d$_6$) δ ppm 9.91 (s, 1H), 9.73 (s, 1H), 8.34 (d, J=8.3 Hz, 1H), 7.72 (d, J=8.1 Hz, 1H), 7.46 (t, J=7.9 Hz, 1H), 7.30 (t, J=7.8 Hz, 1H), 7.06 (d, J=7.6 Hz, 1H), 7.01 (d, J=7.4 Hz, 1H), 3.90 (s, 3H), 3.87 (s, 3H), 3.42-3.33 (m, 6H), 3.23 (s, 3H), 2.80-2.71 (m, 4H), 2.70-2.60 (m, 4H), 2.57-2.42 (m, 4H), 1.98 (s, 3H), 1.88-1.78 (m, 2H), 1.74-1.65 (m, 2H), 1.57-1.20 (m, 20H), 1.08 (s, 2H).

Example 3

4-(2-(2-((2'-chloro-3'-(5-(2-(4-(ethoxymethyl)bicyclo[2.2.1]heptan-1-yl)ethyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid I-3

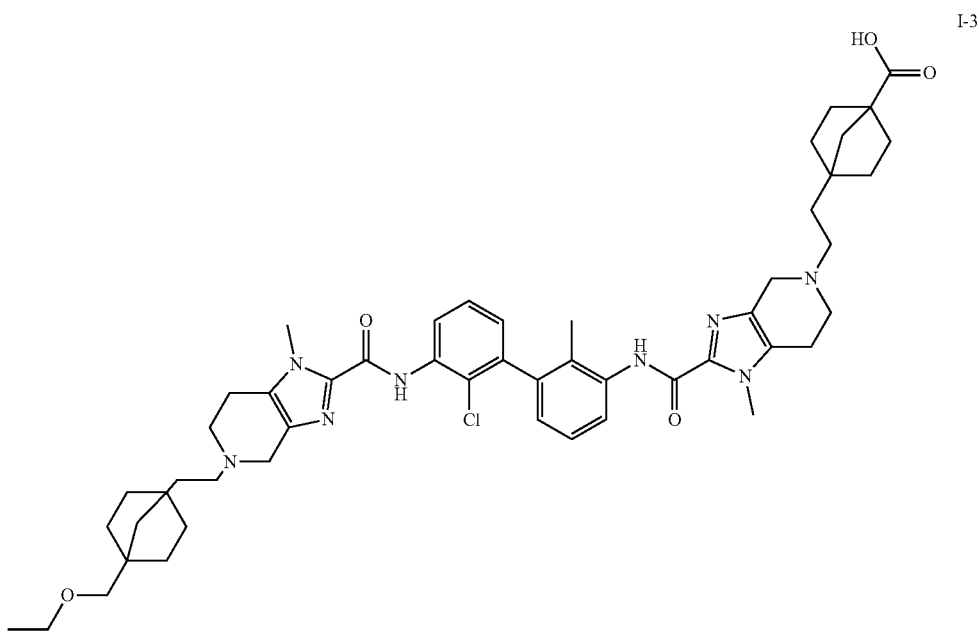 [SMILES: CCOCC12CCC(CCN3CCc4c(nc(C(=O)Nc5cccc(-c6cccc(NC(=O)c7nc8c(n7C)CCN(CCC79CCC(C(=O)O)(CC7)C9)C8)c6C)c5Cl)n4C)C3)(CC1)C2]

Preparation of Intermediate I-3e: 24(2'-chloro-3'-(5-(2-(4-(ethoxymethyl)bicyclo[2.2.1]heptan-1-yl)ethyl)-1-methyl-4,5,6,7-tetrahydro-1H-imidazo[4,5-c]pyridine-2-carboxamido)-2-methyl-[1,1'-biphenyl]-3-yl) carbamoyl)-1-methyl-1,4,6,7-tetrahydro-5H-imidazo[4,5-c]pyridine-5-carboxylic Acid tert-butyl ester Intermediate I-3e was prepared from intermediate I-1c (700.00 mg, 1.06 mmol, 1.0 eq), TEA (1 mL), 2-(4-(ethoxymethyl)bicyclo[2.2.1]heptan-1-yl)acetaldehyde I-3d (312.12 mg, 1.59 mmol, 1.5 eq, synthesis by referring to CN202010997428.3) and NaBH(OAc)$_3$ (1.35 g, 6.36 mmol, 6.0 eq) according to the steps similar to those in intermediate I-1e. (595.00 mg, with a yield of 66.9%). LC-MS MS-ESI (m/z) 839.5 [M+H]+.

Preparation of Intermediate I-3g: 4-(2-(2-((2'-chloro-3'-(5-(2-(4-(ethoxymethyl)bicyclo[2.2.1]heptan-1-yl)ethyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic Acid methyl ester Intermediate I-3g was prepared from intermediate I-3e (595.00 mg, 0.71 mmol, 1.0 eq), TFA (5 mL), TEA (1 mL), 4-(2-oxoethyl)bicyclo[2.2.1]heptane-1-carboxylic acid methyl ester I-1f (209.72 mg, 1.07 mmol, 1.5 eq) and NaBH(OAc)$_3$ (903.12 mg, 4.26 mmol, 6.0 eq) according to the steps similar to those in intermediate I-1g. (450.00 mg, with a yield of 68.9%). LC-MS MS-ESI (m/z) 919.6 [M+H]+.

Preparation of Compound I-3: 4-(2-(2-((2'-chloro-3'-(5-(2-(4-(ethoxymethyl)bicyclo[2.2.1]heptan-1-yl)ethyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic Acid Pale yellow solid I-3 was prepared from intermediate I-3g (450.00 mg, 0.49 mmol, 1.0 eq) and LiOH·H$_2$O (411.60 mg, 9.80 mmol, 20.0 eq) according to the steps similar to those in Compound I-1. (51.00 mg, with a yield of 11.5%). LC-MS MS-ESI (m/z) 905.6 [M+H]+. $^1$H-NMR (400 MHz, DMSO-d$_6$) δ ppm 9.90 (s, 1H), 9.72 (s, 1H), 8.35 (d, J=8.2 Hz, 1H), 7.74 (d, J=8.0 Hz, 1H), 7.45 (t, J=7.9 Hz, 1H), 7.30 (t, J=7.7 Hz, 1H), 7.06 (d, J=7.6 Hz, 1H), 7.00 (d, J=7.7 Hz, 1H), 3.89 (s, 3H), 3.87 (s, 3H), 3.43-3.38 (m, 4H), 3.36 (s, 2H), 3.34-3.30 (m, 2H), 2.79-2.70 (m, 4H), 2.69-2.60 (m, 4H), 2.57-2.51 (m, 4H), 1.99 (s, 3H), 1.92-1.80 (m, 2H), 1.76-1.65 (m, 4H), 1.58-1.42 (m, 10H), 1.41-1.20 (m, 6H), 1.14-1.06 (m, 5H).

Example 4

4-(2-(2-((2'-chloro-3'-(5-(2-(4-(methoxymethyl)bicyclo[2.2.1]heptan-1-yl)ethyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic Acid I-4

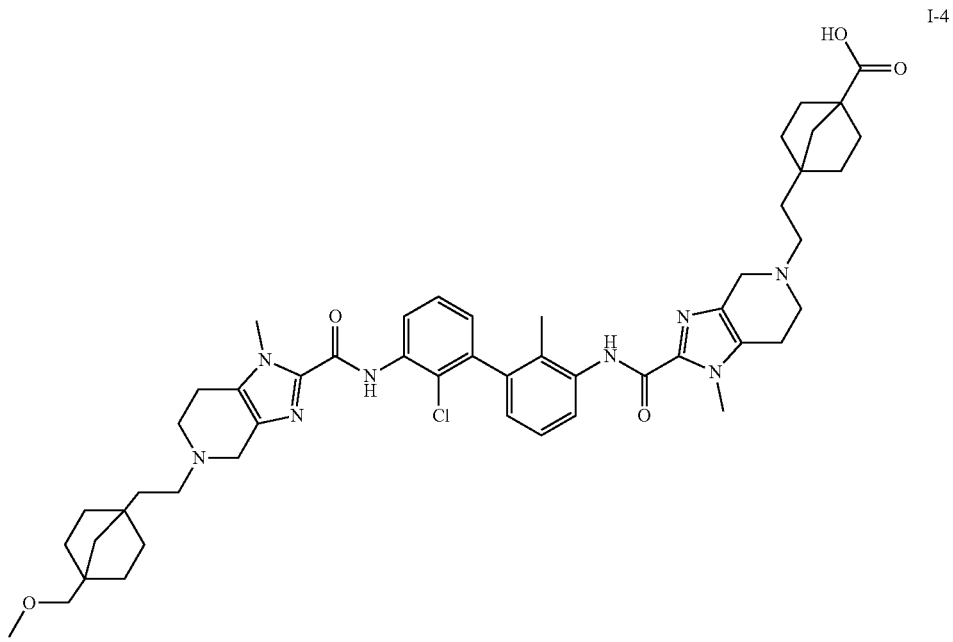 [SMILES: COCC12CCC(CCN3CCc4c(nc(C(=O)Nc5cccc(-c6cccc(NC(=O)c7nc8c(n7C)CCN(CCC79CCC(C(=O)O)(CC7)C9)C8)c6C)c5Cl)n4C)C3)(CC1)C2]

Preparation of Intermediate I-4e: 2-((2'-chloro-3'-(5-(2-(4-(methoxymethyl)bicyclo[2.2.1]heptan-1-yl)ethyl)-1-methyl-4,5,6,7-tetrahydro-1H-imidazo[4,5-c]pyridine-2-carboxamido)-2-methyl-[1,1'-biphenyl]-3-yl) carbamoyl)-1-methyl-1,4,6,7-tetrahydro-5H-imidazo[4,5-c]pyridine-5-carboxylic Acid tert-butyl ester Intermediate I-4e was prepared from intermediate I-1c (600.00 mg, 0.91 mmol, 1.0 eq), TEA (1 mL), 2-(4-(methoxymethyl)bicyclo[2.2.1]heptan-1-yl)acetaldehyde I-4d (248.43 mg, 1.36 mmol, 1.5 eq, synthesis by referring to CN202010997428.3) and NaBH(OAc)$_3$ (1.16 g, 5.46 mmol, 6.0 eq) according to the steps similar to those in intermediate I-1e. (504.00 mg, with a yield of 67.1%). LC-MS MS-ESI (m/z) 825.5 [M+H]+.

Preparation of Intermediate I-4g: 4-(2-(2-((2'-chloro-3'-(5-(2-(4-(methoxymethyl)bicyclo[2.2.1]heptan-1-yl)ethyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid methyl ester Intermediate I-4g was prepared from intermediate I-4e (504.00 mg, 0.61 mmol, 1.0 eq), TFA (5 mL), TEA (1 mL), 4-(2-oxoethyl)bicyclo[2.2.1]heptane-1-carboxylic acid methyl ester I-1f (180.32 mg, 0.92 mmol, 1.5 eq) and NaBH(OAc)$_3$ (775.92 mg, 3.66 mmol, 6.0 eq) according to the steps similar to those in intermediate I-1g. (400.00 mg, with a yield of 72.4%). LC-MS MS-ESI (m/z) 905.6 [M+H]+.

Preparation of Compound I-4: 4-(2-(2-((2'-chloro-3'-(5-(2-(4-(methoxymethyl)bicyclo[2.2.1]heptan-1-yl)ethyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic Acid Pale yellow solid I-4 was prepared from intermediate I-4g (400.00 mg, 0.44 mmol, 1.0 eq) and LiOH·H$_2$O (369.60 mg, 8.80 mmol, 20.0 eq) according to the steps similar to those in Compound I-1. (102.00 mg, with a yield of 26.0%). LC-MS MS-ESI (m/z) 891.6 [M+H]+. $^1$H-NMR (400 MHz, DMSO-d$_6$) δ ppm 9.90 (s, 1H), 9.73 (s, 1H), 8.34 (d, J=8.2 Hz, 1H), 7.73 (d, J=7.9 Hz, 1H), 7.45 (t, J=7.8 Hz, 1H), 7.29 (t, J=7.7 Hz, 1H), 7.06 (d, J=7.3 Hz, 1H), 7.00 (d, J=7.6 Hz, 1H), 3.89 (s, 3H), 3.86 (s, 3H), 3.42-3.38 (m, 4H), 3.32 (s, 2H), 3.23 (s, 3H), 2.77-2.70 (m, 4H), 2.68-2.60 (m, 4H), 2.51-2.56 (m, 4H), 1.98 (s, 3H), 1.90-1.80 (m, 2H), 1.76-1.64 (m, 4H), 1.55-1.20 (m, 16H), 1.11 (s, 2H).

Example 5

4-(2-(2-((2-chloro-3'-(5-(2-(4-(methoxymethyl)bicyclo[2.2.1]heptan-1-yl)ethyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic Acid I-5

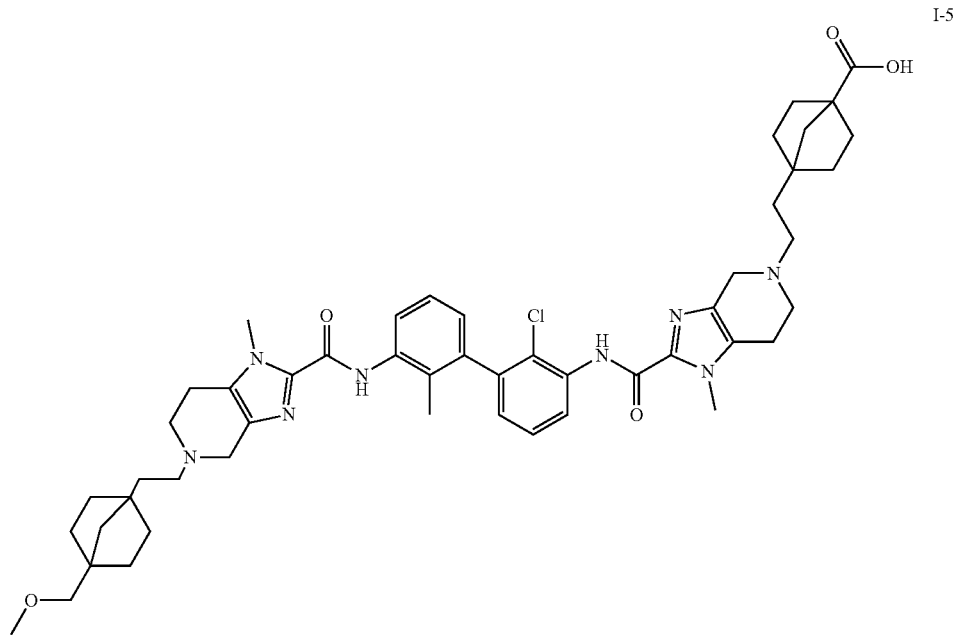 [SMILES: COCC12CCC(CCN3CCc4c(nc(C(=O)Nc5cccc(-c6cccc(NC(=O)c7nc8c(n7C)CCN(CCC79CCC(C(=O)O)(CC7)C9)C8)c6Cl)c5C)n4C)C3)(CC1)C2]

Preparation of Intermediate I-5g: 4-(2-(2-((2-chloro-3'-(5-(2-(4-(methoxymethyl)bicyclo[2.2.1]heptan-1-yl)ethyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic Acid methyl ester Intermediate I-5g was prepared from intermediate I-1h (563.00 mg, 0.67 mmol, 1.0 eq), TFA (5 mL), TEA (1 mL), 2-(4-(methoxymethyl)bicyclo[2.2.1]heptan-1-yl)acetaldehyde I-4d (183.82 mg, 1.01 mmol, 1.5 eq, synthesis by referring to CN202010997428.3) and NaBH(OAc)₃ (852.24 mg, 4.02 mmol, 6.0 eq) according to the steps similar to those in intermediate I-1g. (525.00 mg, with a yield of 86.5%). LC-MS MS-ESI (m/z) 905.6 [M+H]+.

Preparation of Compound I-5: 4-(2-(2-((2-chloro-3'-(5-(2-(4-(methoxymethyl)bicyclo[2.2.1]heptan-1-yl)ethyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic Acid Off-white solid I-5 was prepared from intermediate I-5g (525.00 mg, 0.58 mmol, 1.0 eq) and LiOH·H₂O (487.20 mg, 11.6 mmol, 20.0 eq) according to the steps similar to those in Compound I-1. (116.0 mg, with a yield of 22.4%). LC-MS MS-ESI (m/z) 891.6 [M+H]+. $^1$H NMR (400 MHz, DMSO-$d_6$) δ ppm 9.90 (s, 1H), 9.72 (s, 1H), 8.35 (d, J=8.2 Hz, 1H), 7.74 (d, J=8.1 Hz, 1H), 7.46 (t, J=7.7 Hz, 1H), 7.30 (t, J=7.8 Hz, 1H), 7.07 (d, J=7.4 Hz, 1H), 7.01 (d, J=7.7 Hz, 1H), 3.90 (s, 3H), 3.87 (s, 3H), 3.47-3.40 (m, 4H), 3.33 (s, 2H), 3.24 (s, 3H), 2.79-2.70 (m, 4H), 2.69-2.60 (m, 4H), 2.56-2.51 (m, 4H), 1.99 (s, 3H), 1.89-1.81 (m, 2H), 1.76-1.69 (m, 4H), 1.58-1.22 (m, 16H), 1.12 (s, 2H).

Example 6

4-(2-(2-((2,2'-dichloro-3'-(5-(2-(4-(methoxymethyl)bicyclo[2.2.1]heptan-1-yl)ethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid I-6

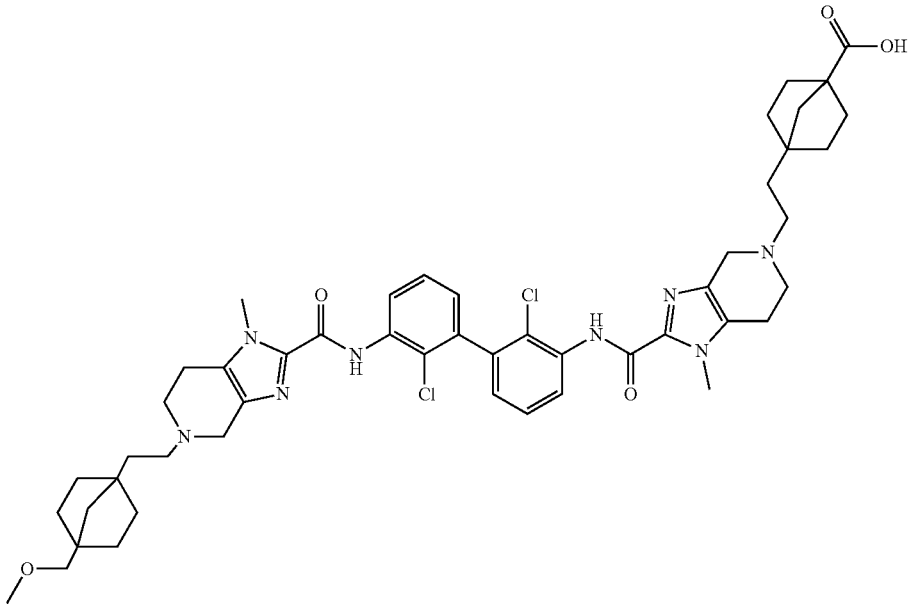

I-6

Preparation of Intermediate I-6c: 2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylic Acid tert-butyl ester I-6c Intermediate I-6c was prepared from 2-((3-bromo-2-chlorophenyl)carbamoyl)-1-methyl-1,4,6,7-tetrahydro-5H-imidazo[4,5-c]pyridine-5-carboxylic acid tert-butyl ester I-1a (530.00 mg, 1.13 mmol, 1.0 eq), TFA (5 mL), 1,4-dioxane (10 mL), 2-((2-chloro-3-(4,4,5,5-tetramethyl-1,3,2-dioxaborolan-2-yl)phenyl)carbamoyl)-1-methyl-1,4,6,7-tetrahydro-5H-imidazo[4,5-c]pyridine-5-carboxylic acid tert-butyl ester I-6b (583.08 mg, 1.13 mmol, 1.0 eq, synthesis by referring to CN202010997428.3), PdCl₂(dcypf) (83.05 mg, 0.11 mmol, 0.1 eq), anhydrous Na₂CO₃ (359.34 mg, 3.39 mmol, 3.0 eq) and water (5 mL) according to the steps similar to those in intermediate I-1c. (363.00 mg, with a yield of 47.3%). LC-MS MS-ESI (m/z) 679.6 [M+H]+.

Preparation of Intermediate I-6e: 2-((2,2'-dichloro-3'-(5-(2-(4-(methoxymethyl)bicyclo[2.2.1]heptan-1-yl)ethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylic Acid tert-butyl ester Intermediate I-6e was prepared from intermediate I-6c (363.00 mg, 0.53 mmol, 1.0 eq), TEA (1 mL), 2-(4-

(methoxymethyl)bicyclo[2.2.1]heptan-1-yl)acetaldehyde I-4d (143.78 mg, 0.79 mmol, 1.5 eq) and NaBH(OAc)₃ (674.16 mg, 3.18 mmol, 6.0 eq) according to the steps similar to those in intermediate I-1e. (338.00 mg, with a yield of 75.4%). LC-MS MS-ESI (m/z) 845.9 [M+H]+.

Preparation of Intermediate I-6g: 4-(2-(2-((2,2'-dichloro-3'-(5-(2-(4-(methoxymethyl)bicyclo[2.2.1]heptan-1-yl)ethyl)-1-methyl-4,5,6,7-tetrahydro-1H-imidazo[4,5-c]pyridine-2-carboxamido))-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic Acid methyl ester Intermediate I-6g was prepared from intermediate I-6e (338.00 mg, 0.40 mmol, 1.0 eq), TFA (5 mL), TEA (1 mL), 4-(2-oxoethyl)bicyclo[2.2.1]heptane-1-carboxylic acid methyl ester I-1f (117.6 mg, 0.60 mmol, 1.5 eq) and NaBH(OAc)₃ (508.80 mg, 2.40 mmol, 6.0 eq) according to the steps similar to those in intermediate I-1g. (307.00 mg, with a yield of 82.9%). LC-MS MS-ESI (m/z) 926.0 [M+H]+.

Preparation of Compound I-6: 4-(2-(2-((2,2'-dichloro-3'-(5-(2-(4-(methoxymethyl)bicyclo[2.2.1]heptan-1-yl)ethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic Acid Off-white solid I-6 was prepared from intermediate I-6g (307.00 mg, 0.33 mmol, 1.0 eq) and LiOH·H₂O (277.20 mg, 6.60 mmol, 20.0 eq) according to the steps similar to those in Compound I-1. (84.00 mg, with a yield of 27.9%). LC-MS MS-ESI (m/z) 912.0 [M+H]+. 1E-NMR (400 MHz, DMSO-d₆) δ ppm 9.89 (s, 2H), 8.38 (d, J=8.4 Hz, 2H), 7.49 (t, J=8.0 Hz, 2H), 7.14 (d, J=7.4 Hz, 2H), 3.90 (s, 6H), 3.48-3.41 (m, 4H), 3.33 (s, 2H), 3.24 (s, 3H), 2.78-2.70 (m, 4H), 2.69-2.62 (m, 4H), 2.56-2.51 (m, 4H), 1.89-1.83 (m, 2H), 1.75-1.69 (m, 4H), 1.58-1.22 (m, 16H), 1.12 (s, 2H).

Example 7

4-(2-(2-((2,2'-dichloro-3'-(5-(2-(4-((difluoromethoxy)methyl)bicyclo[2.2.1]heptan-1-yl)ethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid I-7

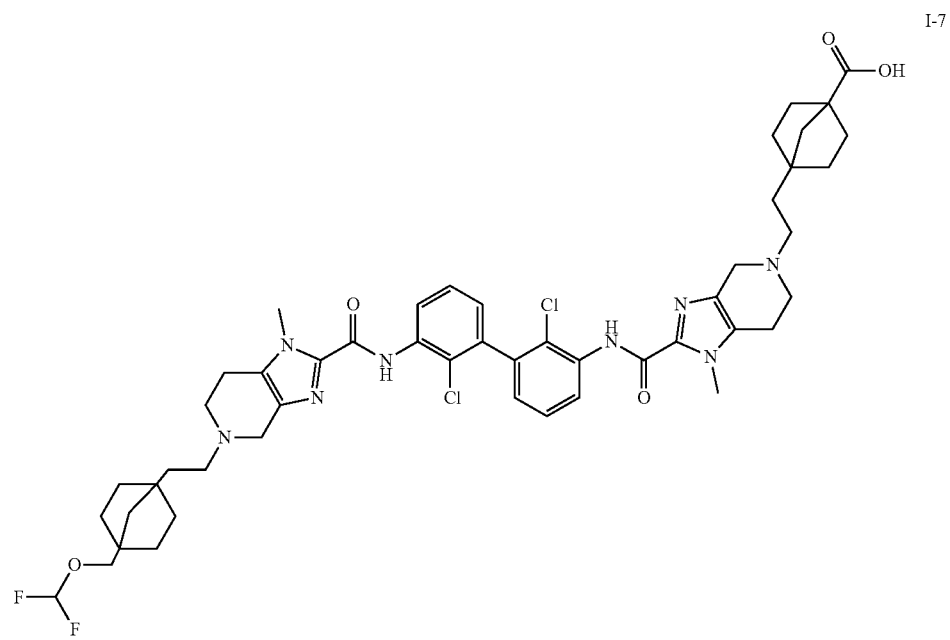 [SMILES: Cn1c(C(=O)Nc2cccc(-c3cccc(NC(=O)c4nc5c(n4C)CCN(CCC46CCC(C(=O)O)(CC4)C6)C5)c3Cl)c2Cl)nc2c1CCN(CCC13CCC(COC(F)F)(CC1)C3)C2]

81
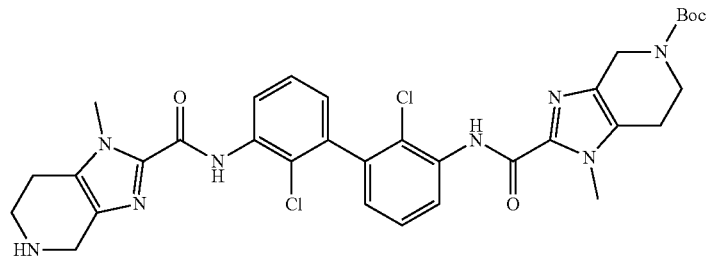
I-6c
82
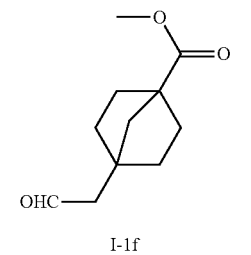
I-1f
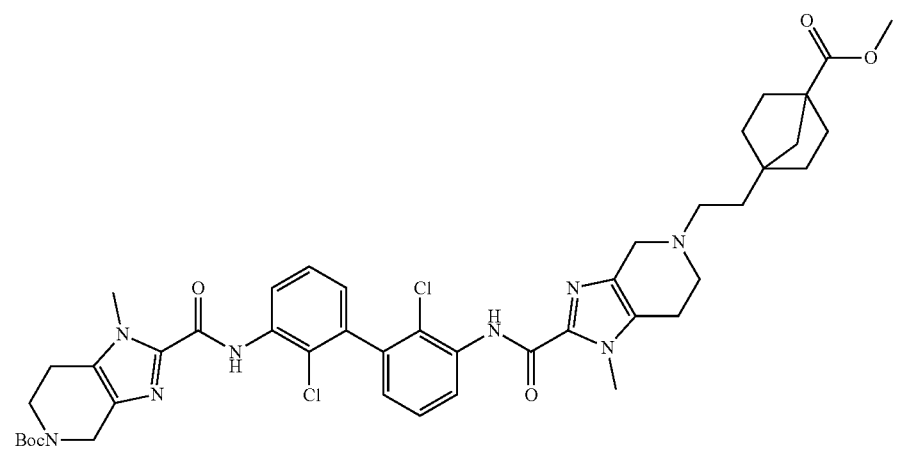
I-7h
Ester hydrolysis
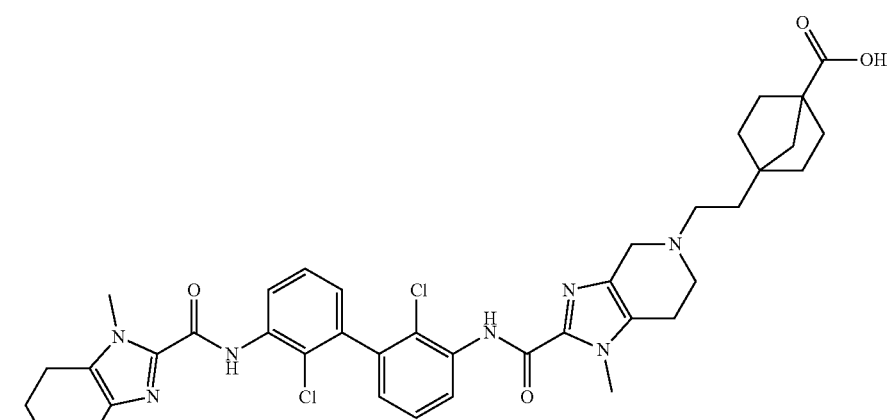
I-7i
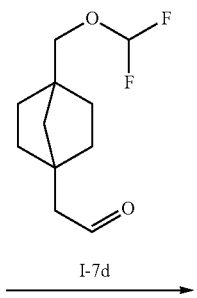
I-7d

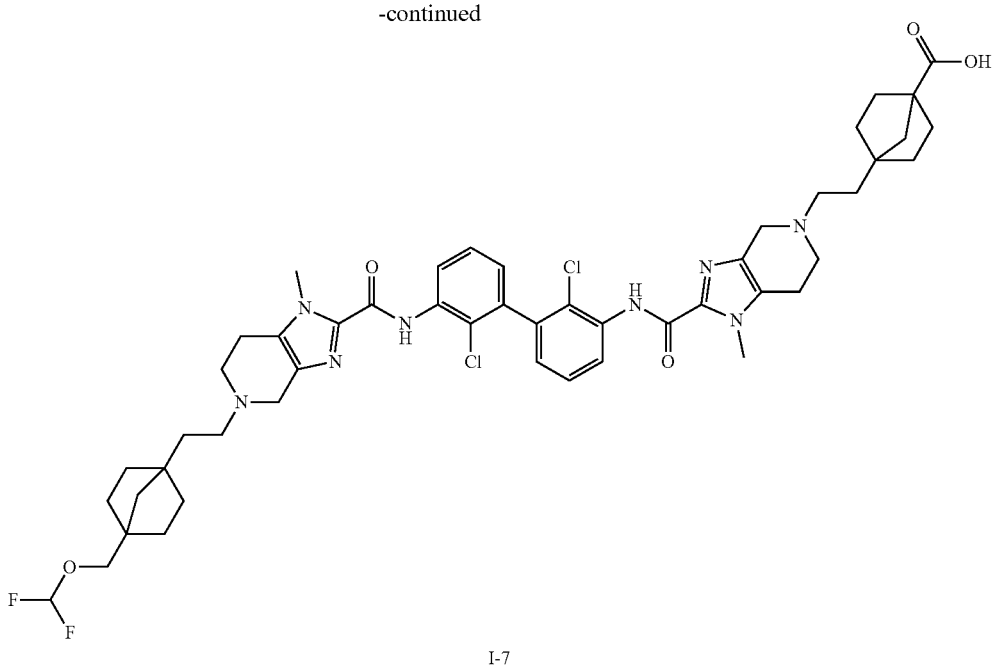

I-7

Preparation of Intermediate I-7d: 2-(4-((difluoromethoxy)methyl)bicyclo[2.2.1]heptan-1-yl)acetaldehyde

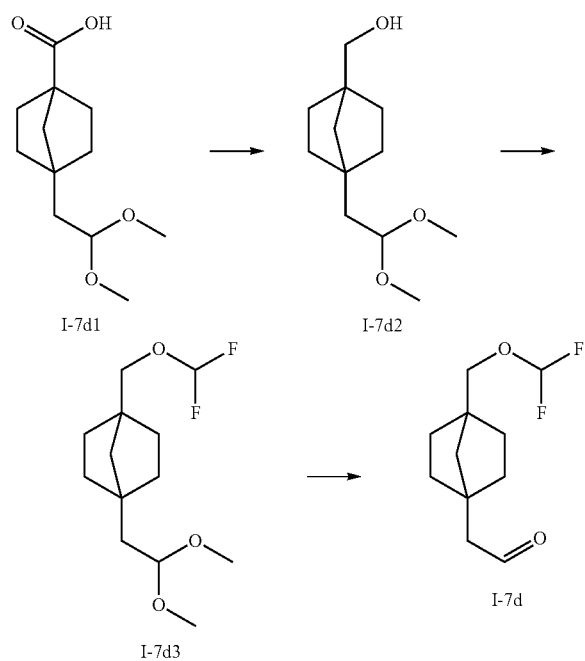

Commercially available compound I-7d1 (300.0 g, 1.31 mol, 1.0 eq) was dissolved in THF (2.5 L). The reaction solution was cooled to 0° C. under the protection of nitrogen, and BH$_3$-Me$_2$S (1.57 mol, 157 mL, 1.2 eq) was then added dropwise. The reaction solution was then naturally heated to 20° C. and further stirred for 16 h. TLC indicated the completion of reaction. The reaction solution was cooled to 0° C. and MeOH (500 mL) was added dropwise to quench the reaction. The reaction solution was then directly concentrated and dried to obtain a colorless oily compound I-7d2 (280.00 g, with a yield of 99.4%). 1H-NMR (400 MHz, CDCl$_3$) δ ppm 4.48 (t, J=5.5 Hz, 1H), 3.82 (s, 2H), 3.32 (s, 6H), 1.81 (d, 2H), 1.32-1.58 (m, 10H).

Compound I-7d2 (21.00 g, 97.99 mmol, 1.0 eq), KHF$_2$ (23.17 g, 391.97 mmol, 4.0 eq), DCM (100 mL) and water (100 mL) were added into a reaction flask and the resulting solution was then cooled to 10° C. under the protection of nitrogen. Difluorobromomethyl trimethylsilane (39.80 g, 195.99 mmol, 2.0 eq) was added dropwise. The system was slowly heated to 12° C. and reacted at 10-15° C. for 1 h, and then heated to room temperature and reacted for 1 h. TLC was carried out, indicating that there was raw material that had not reacted completely. The system was further stirred at room temperature for 16 h. TLC was then carried out again, indicating that a small amount of raw materials were still not completely reacted. Liquid-liquid separation was carried out, the aqueous phase was extracted once with DCM (50 mL), and the organic phases were combined, dried with anhydrous magnesium sulfate, and subjected to rotary evaporation to dryness, thus obtaining a light yellow oily compound I-7d3 (14.60 g, with a yield of 56.4%).

Compound I-7d3 (14.60 g, 55.24 mmol, 1.0 eq) and Acetone (172 mL) were added into a reaction flask and the resulting solution was then cooled to 10° C. under the protection of nitrogen. 2M HCl (100 mL, 3.62 eq) was then added to react at this temperature for 30 min, and the reaction solution was then warmed to room temperature and reacted for 1 h. GC was carried out indicating that the reaction of raw materials was completed. The organic solvent was evaporated out at 45° C. under reduced pressure. The reaction solution was then cooled to room temperature, extracted with MTBE (50 mL×2), dried and subjected to rotary evaporation to dryness to obtain an oil product. The crude product was separated by silica gel column chromatography (PE/EA (v/v)=30/1~50/1) to obtain a colorless oily compound I-7d (9.21 g, with a yield of 76.4%). $^1$H-NMR (400 MHz, CDCl$_3$) δ ppm 9.82 (t, 1H), 6.22 (t, $^2J_{F-H}$=75.1 Hz, 1H), 3.91 (s, 2H), 2.60 (s, 2H), 1.64 (m, 6H), 1.42 (m, 4H).

Preparation of Intermediate I-7h: 2-((2,2'-dichloro-3'-(5-(2-(4-(methoxycarbonyl)bicyclo[2.2.1]heptan-1-yl)ethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylic Acid tert-butyl ester Yellow solid intermediate I-7h was prepared from intermediate 2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylic acid tert-butyl ester I-6c (400.00 mg, 0.59 mmol, 1.0 eq), TEA (1 mL), (172.48 mg, 0.88 mmol, 1.5 eq) and NaBH(OAc)$_3$ (750.48 mg, 3.54 mmol, 6.0 eq) according to the steps similar to those in intermediate I-1e. (457.00 mg, with a yield of 90.2%). LC-MS MS-ESI (m/z) 859.3 [M+H]+.

Preparation of Intermediate I-71: 4-(2-(2-((3'-(5-(tert-butoxycarbonyl)-1-methyl-4,5,6,7-tetrahydro-1H-imidazo[4,5-c]pyridine-2-carboxamido)-2,2'-dichloro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic Acid Off-white intermediate I-71 was prepared from intermediate I-7h (457.00 mg, 0.53 mmol, 1.0 eq) and LiOH·H$_2$O (445.20 mg, 10.6 mmol, 20.0 eq) according to the steps similar to those in example I-1. (376.00 mg, with a yield of 84.0%). LC-MS MS-ESI (m/z) 845.3 [M+H]+.

Preparation of Compound I-7: 4-(2-(2-((2,2'-dichloro-3'-(5-(2-(4-((difluoromethoxy)methyl)bicyclo[2.2.1]heptan-1-yl)ethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic Acid Off-white solid I-7 was prepared from intermediate I-71 (376.00 mg, 0.44 mmol, 1.0 eq), TFA (5 mL), TEA (1 mL), I-7d (143.88 mg, 0.66 mmol, 1.5 eq) and NaBH(OAc)$_3$ (559.68 mg, 2.64 mmol, 6.0 eq) according to the steps similar to those in intermediate I-1e. (202.00 mg, with a yield of 48.4%). LC-MS MS-ESI (m/z) 947.4 [M+H]+. $^1$H-NMR (400 MHz, DMSO-d$_6$) δ ppm 9.89 (s, 2H), 8.38 (d, J=8.2 Hz, 2H), 7.47 (t, J=7.9 Hz, 2H), 7.13 (d, J=7.6 Hz, 2H), 6.63 (t, $^2J_{F-H}$=76.0 Hz, 1H), 3.88 (s, 6H), 3.84 (s, 2H), 3.39 (s, 4H), 2.78-2.70 (m, 4H), 2.67-2.60 (m, 4H), 2.56-2.51 (m, 4H), 1.89-1.80 (m, 2H), 1.76-1.67 (m, 4H), 1.58-1.26 (m, 16H), 1.15 (s, 2H).

Example 8

4-(2-(2-((2,2'-dichloro-3'-(5-((4-(methoxymethyl)bicyclo[2.2.1]heptan-1-yl)methyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid I-8

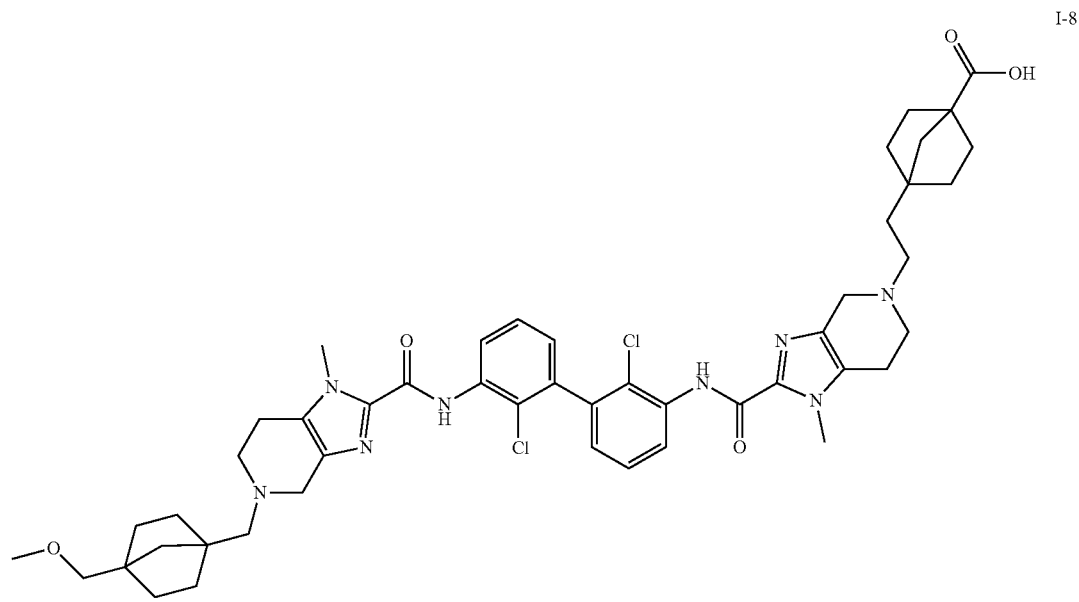 [SMILES: COCC12CCC(CN3CCc4c(nc(C(=O)Nc5cccc(-c6cccc(NC(=O)c7nc8c(n7C)CCN(CCC79CCC(C(=O)O)(CC7)C9)C8)c6Cl)c5Cl)n4C)C3)(CC1)C2]

I-8

Preparation of Intermediate I-8d: 4-(methoxymethyl)bicyclo[2.2.1]heptane-1-carbaldehyde

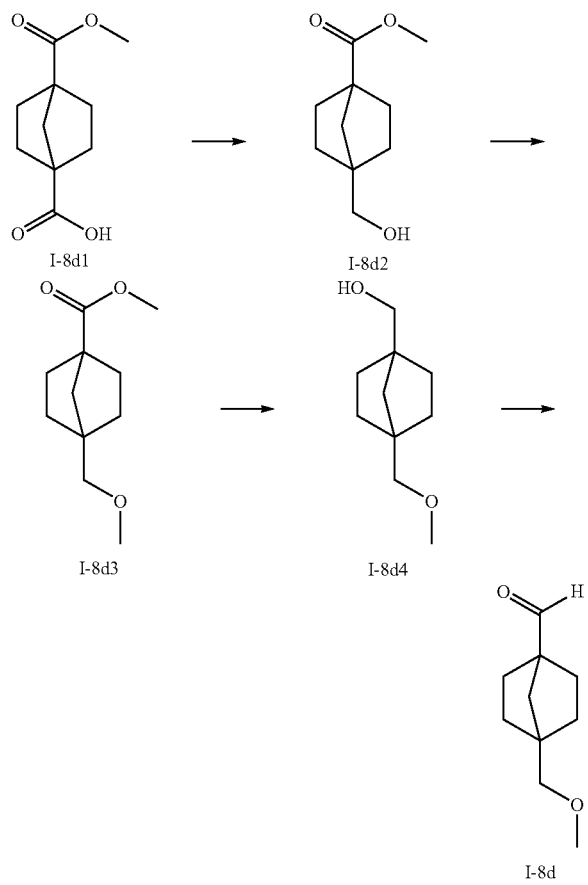

Commercially available compound I-8d1 (60.00 g, 302.70 mmol, 1.0 eq) was dissolved in THF (0.6 L) and the resulting solution was then placed in a four-necked bottle. The reaction solution was then cooled to 0-10° C. under the protection of nitrogen. $BH_3\text{-}Me_2S$ (60.5 mL, 2.0 eq) was then added dropwise. During the addition of $BH_3\text{-}Me_2S$, the temperature did not change obviously, but there was obvious release of gas. The reaction solution was then naturally heated to room temperature of 20° C., and stirred overnight and reacted for 16 h. TLC was carried out, indicating that the reaction of raw materials was completed. The reaction solution was then cooled to 0-10° C., a saturated $NH_4Cl$ solution was then added dropwise, and the mixed solution was then stirred for 1 h. The system was layered, and the aqueous phase was discarded when there was almost no product therein under the monitoring by TLC. The organic phase was dried with magnesium sulfate and evaporated to dryness. The crude product was separated by silica gel column chromatography (PE/EA (v/v)=20/1~10/1) to obtain a light yellow liquid compound I-8d2 (49.70 g, with a yield of 89.12%). $^1$H-NMR (400 MHz, $CDCl_3$) δ ppm 3.66 (d, 5H), 2.33 (s, 1H), 1.98 (m, 2H), 1.66 (m, 4H), 1.55 (d, 2H), 1.40 (m, 2H).

The compound I-8d2 (25.00 g, 135.70 mmol, 1.0 eq) was dissolved in DMF (100 mL), then MeI (192.61 g, 1.36 mol, 10.0 eq) and $Ag_2O$ (94.34 g, 407.10 mmol, 3.0 eq) were added at a time. There was no obvious heat release or gas release in the reaction system. The reaction solution was stirred at room temperature of 20° C. overnight and reacted for 16 h. TLC was carried out, indicating the reaction was completed. Insoluble matters were filled out, 1 L of water was added to the filtrate, and extraction with EA (100 mL×3) was then carried out. The aqueous phase was discarded and the organic phase was washed once with a saturated sodium chloride solution (200 mL). The organic phase was dried with magnesium sulfate, filtered, and subjected to rotary evaporation to dryness. The crude product was separated by silica gel column chromatography (PE/EA (v/v)=30/1) to obtain a light yellow liquid compound I-8d3 (24.00 g, with a yield of 89.21%). 1H-NMR (400 MHz, $CDCl_3$) δ ppm 3.66 (s, 3H), 3.42 (s, 2H), 3.35 (s, 3H), 2.04 (m, 2H), 1.94 (m, 4H), 1.56 (s, 2H), 1.38 (m, 2H).

The compound I-8d3 (18.00 g, 90.79 mmol, 1.0 eq) was dissolved in THF (200 mL), and the resulting solution was then cooled to −10-0° C. LAH (3.45 g, 90.79 mmol, 1.0 eq) was then added step by step. Heat and gas were released violently during the addition of LAH, and a large amount of insoluble white solids were produced. The reaction solution was then naturally heated to room temperature of 20° C. and stirred to react for 2 h. TLC was carried out, indicating the reaction was completed. The reaction solution was cooled to −10° C., 2 mL of water and 2 mL of NaOH aqueous solution (15%) were then added dropwise, and finally 6 mL of water was added. The reaction was quenched for 10 min, anhydrous magnesium sulfate was added for drying for 10 min, and filtering and rotary evaporation were then carried out. The crude product was separated by silica gel column chromatography (PE/EA (v/v)=10/1) to obtain a light yellow liquid compound I-8d4 (13.00 g, with a yield of 84.10%). 1H-NMR (400 MHz, $CDCl_3$) δ ppm 3.66 (s, 2H), 3.41 (s, 2H), 3.35 (s, 3H), 1.75 (s, 1H), 1.62 (m, 4H), 1.38 (m, 4H), 1.19 (s, 2H).

$(COCl)_2$ (9.69 g, 76.36 mmol, 1.3 eq) was dissolved in DCM (200 mL), and the resulting solution was then cooled to about −70° C. in a liquid nitrogen-ethanol bath under the protection of nitrogen. DMSO (9.18 g, 117.48 mmol, 2.0 eq) was then added dropwise and the reaction solution was then held at the current temperature for 15 min. The DCM (200 mL) solution of the compound I-8d4 (10.00 g, 58.74 mmol, 1.0 eq) was then added dropwise and the reaction solution was held at the current temperature for 15 min. TEA (17.83 g, 176.21 mmol, 3.0 eq) was then added dropwise and the reaction solution was naturally heated to room temperature of 20° C. and stirred to react for 4 h. TLC was carried out, indicating the reaction was completed. The reaction solution was directly poured into 0.5 L of water, the pH of the resulting solution was adjusted to about 3-4 with 1 M diluted hydrochloric acid, liquid-liquid separation was then carried out, and the aqueous phase was discarded. The organic phase was cooled to 15° C., and $NaHSO_3$ (14.81 g, 117.48 mmol, 2.0 eq) aqueous solution (200 mL) was added at one time. There was no obvious heat release or gas release during the reaction. The reaction solution was then naturally heated to room temperature of 20° C., and then stirred overnight to react for 16 h. Under the monitoring of TLC, product point disappeared, with forming sodium salt. The reaction solution was extracted with DCM (100×2 mL), and the organic phase was discarded. The pH of the aqueous phase was adjusted to about 10 with $Na_2CO_3$ (21.79 g, 205.58 mmol, 3.5 eq) solid and then stirred for 10 min, extracted with DCM (200 mL), and washed once with a saturated sodium chloride solution (100 mL). The organic phase was dried with anhydrous magnesium sulfate, filtered, and subjected to rotary evaporation to dryness. The crude product was separated by silica gel column chromatography (PE/EA (v/v)=30/1) to obtain a colorless transparent liquid compound I-8d (3.26 g, with a yield of 32.99%). 1-H-NMR (400 MHz, CDCl$_3$) δ ppm 9.80 (s, 1H), 3.45 (s, 2H), 3.37 (s, 3H), 2.03 (m, 2H), 1.70 (m, 2H), 1.50 (s, 3H), 1.43 (m, 3H).

Preparation of Compound I-8: 4-(2-(2-((2,2'-dichloro-3'-(5-((4-(methoxymethyl)bicyclo[2.2.1]heptan-1-yl)methyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic Acid White solid I-8 was prepared from intermediate I-71 (112.00 mg, 0.13 mmol, 1.0 eq), TFA (5 mL), TEA (1 mL), I-8d (33.60 mg, 0.20 mmol, 1.5 eq) and NaBH(OAc)$_3$ (165.36 mg, 0.78 mmol, 6.0 eq) according to the steps similar to those in intermediate I-1e. (73.00 mg, with a yield of 62.6%). LC-MS MS-ESI (m/z) 897.4 [M+H]+. $^1$H-NMR (400 MHz, DMSO-d$_6$) δ ppm 9.88 (s, 2H), 8.36 (d, J=8.2 Hz, 2H), 7.47 (t, J=7.9 Hz, 2H), 7.12 (d, J=7.5 Hz, 2H), 3.88 (s, 6H), 3.47 (s, 2H), 3.39 (s, 2H), 3.32 (s, 2H), 3.22 (s, 3H), 2.82-2.70 (m, 4H), 2.69-2.61 (m, 4H), 2.57 (s, 2H), 2.55-2.51 (m, 2H), 1.88-1.78 (m, 2H), 1.73-1.66 (m, 2H), 1.60-1.41 (m, 8H), 1.40-1.20 (m, 8H), 1.15 (s, 2H).

Example 9

4-(2-(2-((2-chloro-2'-fluoro-3'-(5-(2-(4-(methoxymethyl)bicyclo[2.2.1]heptan-1-yl)ethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic Acid I-9

Preparation of Intermediate I-9c: 24(2-chloro-2'-fluoro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylic Acid tert-butyl ester Intermediate I-9c was prepared from 2-((3-bromo-2-fluorophenyl)carbamoyl)-1-methyl-1,4,6,7-tetrahydro-5H-imidazo[4,5-c]pyridine-5-carboxylic acid tert-butyl ester I-9a (490.00 mg, 1.08 mmol, 1.0 eq, synthesis by referring to CN202010997428.3), TFA (3 mL), 1,4-dioxane (10 mL), 2-((2-chloro-3-(4,4,5,5-tetramethyl-1,3,2-dioxaborolan-2-yl)phenyl)carbamoyl)-1-methyl-1,4,6,7-tetrahydro-5H-imidazo[4,5-c]pyridine-5-carboxylic acid tert-butyl ester I-6b (613.01 mg, 1.13 mmol, 1.1 eq, synthesis by referring to CN202010997428.3), PdCl$_2$(dcypf) (83.05 mg, 0.11 mmol, 0.1 eq), anhydrous Na$_2$CO$_3$ (343.44 mg, 3.24 mmol, 3.0 eq) and water (5 mL) according to the steps similar to those in intermediate I-1c. (312.00 mg, with a yield of 43.6%). LC-MS MS-ESI (m/z) 663.3 [M+H]+.

Preparation of Intermediate I-9h: 2-((2-chloro-2'-fluoro-3'-(5-(2-(4-(methoxycarbonyl)bicyclo[2.2.1]heptan-1-yl)ethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylic Acid tert-butyl ester Yellow solid intermediate I-9h was prepared from intermediate I-9c (312.00 mg, 0.47 mmol, 1.0 eq), TEA (1 mL), (138.36 mg, 0.71 mmol, 1.5 eq) and NaBH(OAc)$_3$ (716.28 mg, 2.82 mmol, 6.0 eq) according to the steps similar to those in intermediate I-1e. (335.00 mg, with a yield of 84.6%). LC-MS MS-ESI (m/z) 843.4 [M+H]+.

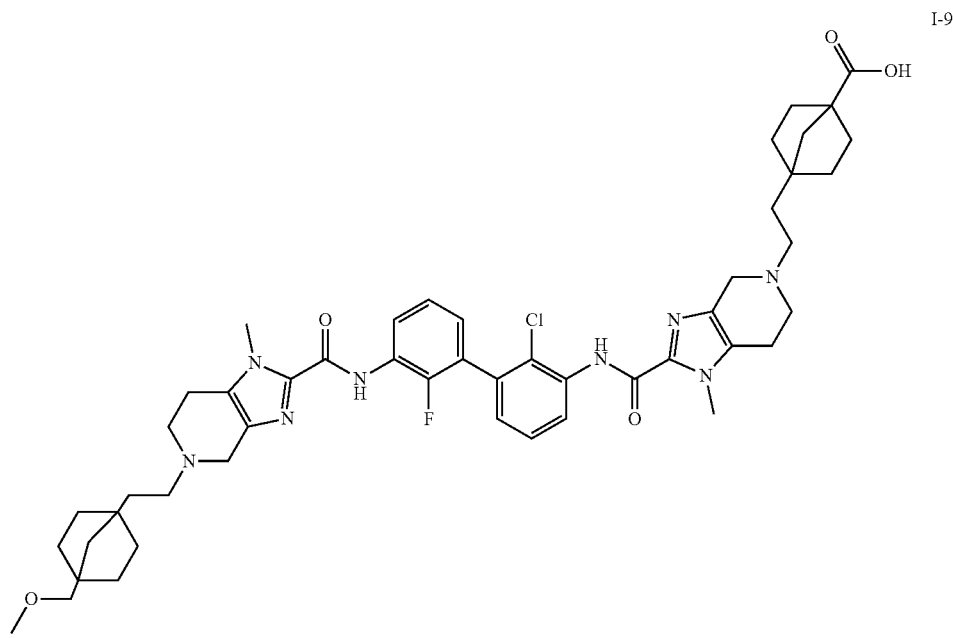 [SMILES: COCC12CCC(CCN3CCc4c(nc(C(=O)Nc5cccc(-c6cccc(NC(=O)c7nc8c(n7C)CCN(CCC79CCC(C(=O)O)(CC7)C9)C8)c6Cl)c5F)n4C)C3)(CC1)C2]

Preparation of Intermediate I-91: 4-(2-(2-((3'-(5-(tert-butoxycarbonyl)-1-methyl-4,5,6,7-tetrahydro-1H-imidazo[4,5-c]pyridine-2-carboxamido)-2'-chloro-2-fluoro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic Acid Off-white intermediate I-91 was prepared from intermediate I-9h (330.00 mg, 0.39 mmol, 1.0 eq) and LiOH·H$_2$O (327.60 mg, 7.80 mmol, 20.0 eq) according to the steps similar to those in Example I-1. (252.00 mg, with a yield of 77.9%). LC-MS MS-ESI (m/z) 829.4 [M+H]+.

Preparation of Compound I-9: 4-(2-(24(2-chloro-2'-fluoro-3'-(5-(2-(4-(methoxymethyl) bicyclo[2.2.1]heptan-1-yl)ethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic Acid Off-white solid I-9 was prepared from intermediate I-91 (152.00 mg, 0.18 mmol, 1.0 eq), TFA (5 mL), TEA (2 mL), I-8d (49.14 mg, 0.27 mmol, 1.5 eq) and NaBH(OAc)$_3$ (228.96 mg, 1.08 mmol, 6.0 eq) according to the steps similar to those in intermediate I-1e. (78.00 mg, with a yield of 48.4%). LC-MS MS-ESI (m/z) 895.4 [M+H]+. $^1$H-NMR (400 MHz, DMSO-d$_6$) δ ppm 9.93 (s, 1H), 9.78 (s, 1H), 8.35 (d, J=8.1 Hz, 1H), 8.07 (t, J=7.4 Hz, 1H), 7.48 (t, J=8.0 Hz, 1H), 7.31 (t, J=7.8 Hz, 1H), 7.21 (d, J=7.5 Hz, 1H), 7.16 (t, J=7.2 Hz, 1H), 3.89 (s, 3H), 3.87 (s, 3H), 3.41 (s, 2H), 3.39 (s, 2H), 3.32 (s, 2H), 3.23 (s, 3H), 2.79-2.70 (m, 4H), 2.69-2.60 (m, 4H), 2.58-2.50 (m, 4H), 1.94-1.78 (m, 2H), 1.72-1.69 (m, 4H), 1.58-1.18 (m, 16H), 1.11 (s, 2H).

Example 10

4-(2-(2-((2-chloro-3'-(5-(2-(4-((difluoromethoxy)methyl)bicyclo[2.2.1]heptan-1-yl)ethyl)-1-methyl-4,5,6,7-tetrahydro-1H-imidazo[4,5-c]pyridine-2-carboxamido)-2'-fluoro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic Acid I-10

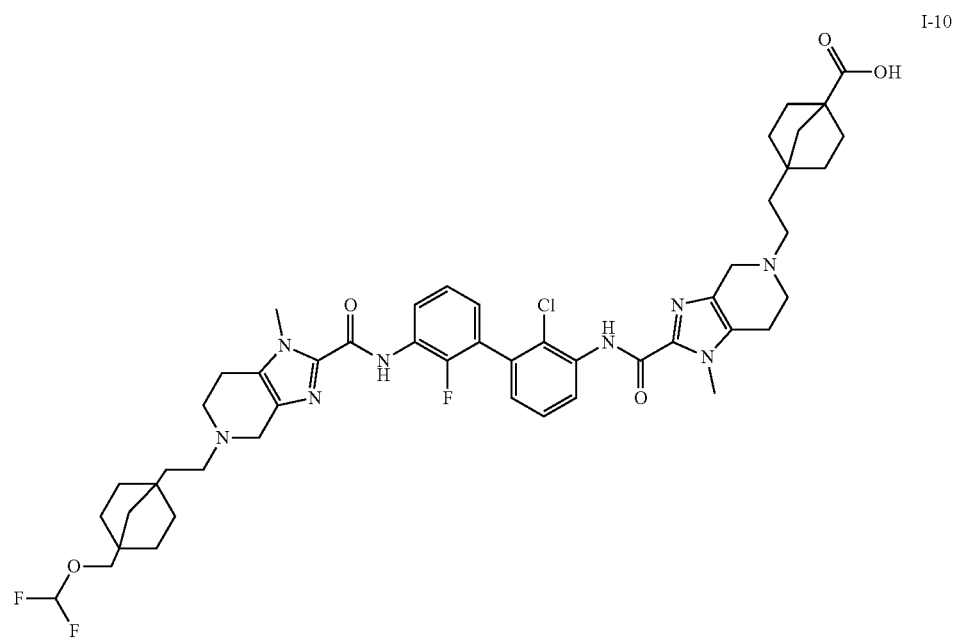 [SMILES: Cn1c(C(=O)Nc2cccc(-c3cccc(NC(=O)c4nc5c(n4C)CCN(CCC46CCC(C(=O)O)(CC4)C6)C5)c3Cl)c2F)nc2c1CCN(CCC13CCC(COC(F)F)(CC1)C3)C2]

Preparation of Compound I-10: 4-(2-(2-((2-chloro-3'-(5-(2-(4-((difluoromethoxy)methyl) bicyclo[2.2.1]heptan-1-yl)ethyl)-1-methyl-4,5,6,7-tetrahydro-1H-imidazo[4,5-c]pyridine-2-carboxamido)-2'-fluoro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic Acid Off-white solid I-10 was prepared from intermediate I-9i (152.00 mg, 0.18 mmol, 1.0 eq), TFA (5.0 mL), TEA (2.0 mL), I-7d (58.86 mg, 0.27 mmol, 1.5 eq) and NaBH(OAc)$_3$ (228.96 mg, 1.08 mmol, 6.0 eq) according to the steps similar to those in intermediate I-1e. (78.00 mg, with a yield of 46.5%). LC-MS MS-ESI (m/z) 931.4 [M+H]+. $^1$H-NMR (400 MHz, DMSO-d$_6$) δ ppm 9.93 (s, 1H), 9.77 (s, 1H), 8.35 (d, J=8.0 Hz, 1H), 8.08 (t, J=7.3 Hz, 1H), 7.48 (t, J=7.8 Hz, 1H), 7.31 (t, J=7.8 Hz, 1H), 7.20 (d, J=7.4 Hz, 1H), 7.15 (t, J=6.7 Hz, 1H), 6.63 (t, $^2$J$_{F-H}$=76.0 Hz, 1H), 3.89 (s, 3H), 3.87 (s, 3H), 3.85 (s, 2H), 3.40 (s, 4H), 2.74 (s, 4H), 2.65 (s, 4H), 2.58-2.51 (m, 4H), 1.94-1.79 (m, 2H), 1.77-1.65 (m, 4H), 1.61-1.25 (m, 16H), 1.16 (s, 2H).

Example 11

4-(2-(2-((2-chloro-2'-cyano-3'-(5-(2-(4-(methoxymethyl)bicyclo[2.2.1]heptan-1-yl)ethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid I-11 butyl ester I-1a (500.00 mg, 1.06 mmol, 1.0 eq), TFA (5 mL), 1,4-dioxane (10 mL), 2-((2-cyano-3-(4,4,5,5-tetramethyl-1,3,2-dioxaborolan-2-yl)phenyl)carbamoyl)-1-methyl-1,4,6,7-tetrahydro-5H-imidazo[4,5-c]pyridine-5-carboxylic acid tert-butyl ester I-11b (537.84 mg, 1.06 mmol, 1.0 eq, synthesis by referring to CN202010997428.3), PdCl$_2$(dcypf) (83.05 mg, 0.11 mmol, 0.1 eq), anhydrous Na$_2$CO$_3$ (337.08 mg, 3.18 mmol, 3.0 eq) and water (5 mL) according to the steps similar to those in intermediate I-1c. (344.00 mg, with a yield of 48.4%). LC-MS MS-ESI (m/z) 670.3 [M+H]+.

Preparation of Intermediate I-11h: 2-((2'-chloro-2-cyano-3'-(5-(2-(4-(methoxycarbonyl)bicyclo[2.2.1]heptan-1-yl)ethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylic Acid tert-butyl ester Yellow solid intermediate I-11h was prepared from intermediate I-11c (344.00 mg, 0.51 mmol, 1.0 eq), TEA (1 mL), I-1f (149.15 mg, 0.76 mmol, 1.5 eq) and NaBH(OAc)$_3$ (648.72 mg, 3.06 mmol, 6.0 eq) according to the steps similar to those in intermediate I-1e. (383.40 mg, with a yield of 88.4%). LC-MS MS-ESI (m/z) 850.4 [M+H]+.

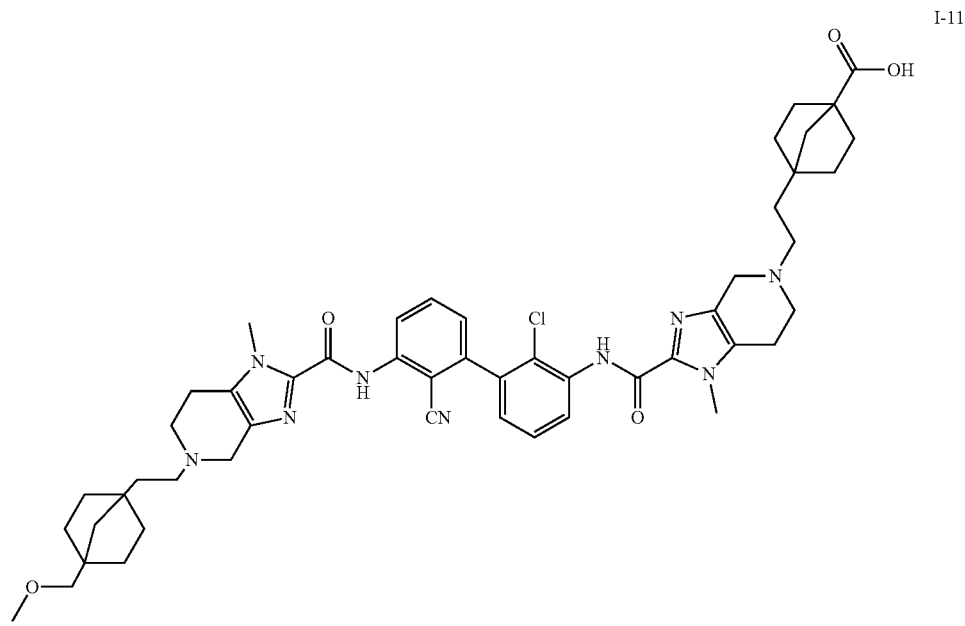 [SMILES: COCC12CCC(CCN3CCc4c(nc(C(=O)Nc5cccc(-c6cccc(NC(=O)c7nc8c(n7C)CCN(CCC79CCC(C(=O)O)(CC7)C9)C8)c6Cl)c5C#N)n4C)C3)(CC1)C2]

Preparation of Intermediate I-11c: 2-((2'-chloro-2-cyano-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylic Acid tert-butyl ester Brown solid intermediate I-11c was prepared from 2-((3-bromo-2-chlorophenyl)carbamoyl)-1-methyl-1,4,6,7-tetrahydro-5H-imidazo[4,5-c]pyridine-5-carboxylic acid tert- Preparation of Intermediate I-11i: 4-(2-(2-((3'-(5-(tert-butoxycarbonyl)-1-methyl-4,5,6,7-tetrahydro-1H-imidazo[4,5-c]pyridine-2-carboxamido)-2'-chloro-2-cyano-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic Acid Off-white intermediate I-11i was prepared from intermediate I-11h (383.40 mg, 0.45 mmol, 1.0 eq) and LiOH·H$_2$O (378.00 mg, 9.0 mmol, 20.0 eq) according to the steps similar to those in Example I-1. (256.00 mg, with a yield of 68.0%). LC-MS MS-ESI (m/z) 836.4 [M+H]+.

Preparation of Compound I-11: 4-(2-(2-((2-chloro-2'-cyano-3'-(5-(2-(4-(methoxymethyl) bicyclo[2.2.1]heptan-1-yl)ethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl) bicyclo[2.2.1]heptane-1-carboxylic Acid Pale yellow solid I-11 was prepared from intermediate I-11i (30.0 mg, 0.036 mmol, 1.0 eq), TFA (2.0 mL), TEA (0.2 mL), I-4d (9.83 mg, 0.054 mmol, 1.5 eq) and NaBH(OAc)₃ (45.79 mg, 0.22 mmol, 6.0 eq) according to the steps similar to those in intermediate I-1e. (19.90 mg, with a yield of 61.2%). LC-MS MS-ESI (m/z) 902.5 [M+H]+. ¹H-NMR (400 MHz, DMSO-d₆) δ ppm 10.38 (s, 1H), 9.94 (s, 1H), 8.42 (d, J=7.3 Hz, 1H), 8.02 (d, J=8.3 Hz, 1H), 7.80 (t, J=8.0 Hz, 1H), 7.53 (t, J=8.0 Hz, 1H), 7.33 (d, J=7.6 Hz, 1H), 7.23 (d, J=7.6 Hz, 1H), 3.90 (s, 3H), 3.87 (s, 3H), 3.46-3.42 (m, 4H), 3.32 (s, 2H), 3.23 (s, 3H), 2.78-2.71 (m, 4H), 2.70-2.64 (m, 4H), 2.57-2.52 (m, 4H), 1.88-1.84 (m, 2H), 1.72-1.70 (m, 4H), 1.52-1.32 (m, 16H), 1.12 (s, 2H).

Example 12

4-((2-((2-chloro-3'-(5-(2-(4-(methoxymethyl)bicyclo[2.2.1]heptan-1-yl)ethyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)methyl)bicyclo[2.2.1]heptane-1-carboxylic Acid I-12

Preparation of Intermediate I-12h: 2-((2'-chloro-3'-(5-((4-(methoxycarbonyl)bicyclo[2.2.1]heptan-1-yl)methyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridine-5-carboxylic Acid tert-butyl ester Yellow solid intermediate I-12h was prepared from intermediate I-1c (132.0 mg, 0.20 mmol, 1.0 eq), TEA (1.0 mL), and commercially available 4-formylbicyclo[2.2.1]heptane-1-carboxylic acid methyl ester I-12f (54.66 mg, 0.30 mmol, 1.5 eq, the manufacturer is Nanjing Yaoshi Technology Co., Ltd.,) and NaBH(OAc)₃ (254.40 mg, 1.20 mmol, 6.0 eq) according to the steps similar to those in intermediate I-1e. (85.0 mg, with a yield of 51.5%). LC-MS MS-ESI (m/z) 825.4 [M+H]+.

Preparation of Intermediate I'-1: 4-((2-((2-chloro-3'-(5-(2-(4-(methoxymethyl)bicyclo[2.2.1]heptan-1-yl)ethyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)methyl)bicyclo[2.2.1]heptane-1-carboxylic Acid methyl ester Intermediate I'-1 was prepared from intermediate I-12h (85.0 mg, 0.10 mol, 1.0 eq), TFA (5 mL), I-4d (27.34 mg, 0.15 mmol, 1.5 eq), TEA (1 mL) and NaBH(OAc)₃ (127.20 mg, 0.60 mmol, 6.0 eq) according to the steps similar to those in intermediate I-1e. (74.0 mg, with a yield of 80.6%). LC-MS MS-ESI (m/z) 891.5 [M+H]+.

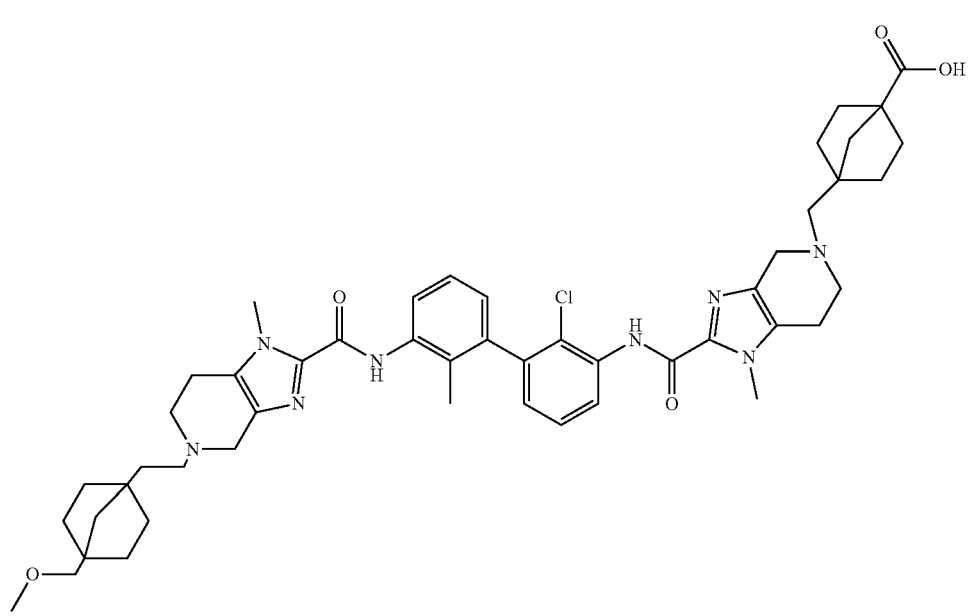

I-12

Preparation of Compound I-12: 4-((2-((2-chloro-3'-(5-(2-(4-(methoxymethyl)bicyclo[2.2.1]heptan-1-yl)ethyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)methyl)bicyclo[2.2.1]heptane-1-carboxylic Acid Off-white solid I-12 was prepared from intermediate I'-1 (74.0 mg, 0.08 mmol, 1.0 eq) and LiOH·H$_2$O (67.20 mg, 1.60 mmol, 20.0 eq) according to the steps similar to those in Example I-1. (37.0 mg, with a yield of 50.8%). LC-MS MS-ESI (m/z) 877.5 [M+H]+. $^1$H-NMR (400 MHz, DMSO-d$_6$) δ ppm 9.90 (s, 1H), 9.73 (s, 1H), 8.33 (d, J=8.5 Hz, 1H), 7.72 (d, J=7.8 Hz, 1H), 7.45 (t, J=8.0 Hz, 1H), 7.29 (t, J=7.8 Hz, 1H), 7.06 (d, J=7.5 Hz, 1H), 7.00 (d, J=7.5 Hz, 1H), 3.89 (s, 3H), 3.86 (s, 3H), 3.48 (s, 2H), 3.40 (s, 2H), 3.33 (s, 2H), 3.23 (s, 3H), 2.82-2.70 (m, 4H), 2.69-2.61 (m, 4H), 2.58 (s, 2H), 2.55-2.51 (m, 2H), 1.98 (s, 3H), 1.87-1.77 (m, 2H), 1.73-1.65 (m, 2H), 1.61-1.20 (m, 16H), 1.12 (s, 2H).

For those skilled in the art, other compounds in this disclosure can be prepared by referring to the above methods and the chemical structure formula shall prevail.

In Vitro Biological Evaluation

The test method is used for the in vitro biological activity evaluation of the compound of the invention, including a method for evaluating in vitro inhibitory activity on binding at protein level and a method for evaluating the biological function activity at cell level.

This test is intended to comprehensively evaluate the in vitro inhibitory activity of different compounds on binding of liquid phase PD-1 and PD-L1 and binding of CD80 and PD-L1 and the blocking effect in inhibiting T cell activation signal after binding of PD-1 and PD-L1 on a cell model.

Example A Evaluation of In Vitro Inhibitory Activity Against PD-1/PD-L1 Binding

Main Principle of Experiment

Homogeneous time resolved fluorescence method (HTRF): This method uses the recombinant human PD-L1 protein fused with hFc tag and the recombinant human PD-1 protein fused with His tag, which are interacting ligands and receptors. When the anti-hFc antibody containing chelated Eu tag and the anti-His antibody containing XL665 fluorescein tag are used to bind with the above two corresponding tags respectively and are excited by 320 nm laser, energy can be transferred from Eu element to XL665 fluorescein due to ligand receptor binding, and the XL665 fluorescein is excited to emit light with a wavelength of 665 nm. When an inhibitor for inhibiting interaction of PD-L1 and PD-1 is added, the binding of the ligand and the receptor is destroyed, causing a long distance between Eu and XL665. As a result, the energy cannot be transferred, and the XL665 fluorescein will not be excited.

Experimental Materials and Devices

The recombinant human PD-1 protein with His tag (His-PD-1 protein, Cat #: 10377-H08H-50) and the recombinant human PD-L1-Fc fusion protein (PD-L1-Fc fusion protein, Cat #: 10084-H02H-100) were purchased from Sino Biological Inc., anti-hFc-Eu$^{3+}$ antibody and anti-His-XL665 antibody were purchased from Cisbio, and other related reagents such as a diluent buffer (diluent buffer 5 (Cat #: 62DL5DDC) and a detection buffer (PPI-European detection buffer, Cat #: 61DB9RDF) were purchased from Cisbio. Fluorescence detector Tecan (Spark 10M) was purchased from Tecan Company in Switzerland.

Main Process of Experiment

The experiment process was carried out according to the flow required in the operating manual of the test reagent. The process was as follows:

(1) Experiment preparation: A test compound was diluted to different concentration gradients with the dilution buffer (the highest final concentration in a 20 μL final reaction system was 10 μM). The His-PD-1 protein was diluted to 800 nM (the final concentration in the 20 final reaction system was 100 nM). The PD-L1-Fc fusion protein was diluted to 16 nM (the final concentration was 2 nM). The anti-His-XL665 antibody and the anti-hFc-Eu$^{3+}$ antibody were diluted 20 times and 100 times respectively with the detection buffer according to reagent requirements.

(2) First, 5 μL of the test compound, 2.5 μL of the PD-L1-Fc fusion protein and 2.5 μL of the His-PD-1 protein solution were well mixed and incubated at room temperature for 15 min; then, 5 μL of the anti-His-XL665 antibody and 5 μL of the anti-hFc-Eu$^{3+}$ antibody were added to the system and further incubated for 3 h before test.

(3) During the test reaction, control groups were set, including a 0% inhibition positive control without adding the test compound and a 100% inhibition negative control without adding the PD-1 protein. All tests were conducted by use of multiple holes.

(4) The fluorescence detector Tecan (Spark 10M) was used to detect the fluorescence signal of each hole. The excitation wavelength was 320 nm, and the emission wavelengths for detection were 620 nm and 665 nm, respectively. The strength of PD-1/PD-L1 binding refers to a fluorescence signal ratio Em665/Em620.

(5) Calculation formula of binding inhibition rate of test compound: Inhibition rate (%)=[1−(fluorescence signal ratio of detected hole−fluorescence signal ratio of 100% inhibition negative control)]/(fluorescence signal ratio of 0% inhibition positive control−fluorescence signal ratio of 100% inhibition negative control)× 100%. The 50% inhibition concentration (IC$_{50}$) was calculated after the PD-1/PD-L1 binding inhibition rates of the test compound with different concentration gradients were calculated respectively. The IC$_{50}$ data of the representative compounds of this disclosure for inhibiting PD-1/PD-L1 binding in vitro are shown in Table 2 below:

TABLE 2

IC$_{50}$ data of representative compounds of this disclosure for inhibiting PD-1/PD-L1 binding in vitro

| Compound number | IC$_{50}$ (nM) |
| --- | --- |
| I-1 | 1.47 |
| I-2 | 1.32 |

TABLE 2-continued

IC$_{50}$ data of representative compounds of this disclosure for inhibiting PD-1/PD-L1 binding in vitro

| Compound number | IC$_{50}$ (nM) |
|---|---|
| I-3 | 1.19 |
| I-4 | 1.89 |
| I-5 | 2.35 |
| I-6 | 1.17 |
| I-7 | 0.29 |
| I-8 | 3.70 |
| I-9 | 0.88 |
| I-10 | 1.13 |
| I-11 | 1.94 |
| I-12 | 2.46 |
| $^a$Example 180 | 4.62 |

$^a$Example 180 is an example disclosed by Incyte Company in patent application CN110267953A. The inventor synthesized the compound with reference to the synthesis method therein for use as a control molecule. The chemical structure of Example 180 was confirmed by LC-MS MS-ESI (m/z) 775.0 [M + H]$^+$ and $^1$H-NMR (400 MHz, DMSO) δ ppm 9.90 (s, 2H), 8.38 (dd, J = 7.6, 2.7 Hz, 2H), 7.49 (t, J = 8.0 Hz, 2H), 7.14 (d, J = 7.7 Hz, 2H), 3.90 (s, 6H), 3.57 (t, J = 6.0 Hz, 2H), 3.51-3.46 (m, 4H), 2.85-2.77 (m, 4H), 2.70-2.64 (m, 4H), 2.64-2.59 (m, 4H), 1.90-1.76 (m, 2H), 1.68-1.55 (m, 2H), 1.54-1.22 (m, 6H). The structural formula of the compound is as follows:

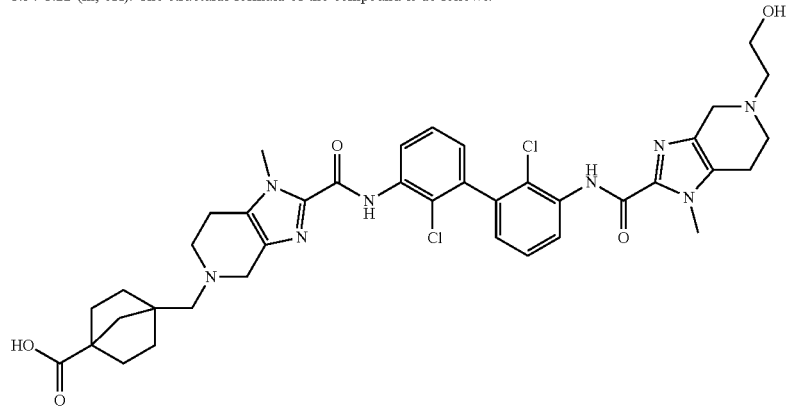

Example 180

It can be seen from the above results that the compounds of this disclosure have excellent activity of inhibiting PD-1/PD-L1 binding in vitro, and the compounds of the general formula (I) of this disclosure also have activity of inhibiting PD-1/PD-L1 binding. Compared with the control molecule, the compounds of this disclosure have obviously excellent activity of inhibiting PD-1/PD-L1 binding.

Example B Evaluation of In Vitro Inhibitory Activity Against CD80/PD-L1 Binding

Main Principle of Experiment

In addition to PD-1, PD-L1 can also play an immune inhibition role by binding to CD80. Similarly, in vitro CD80/PD-L1 binding or binding inhibition test can also be conducted by homogeneous time-resolved fluorescence (HTRF). When the anti-hFc-Eu$^{3+}$ antibody and the anti-His-XL665 antibody are used to bind to the hFC tag fused to PD-L1 and the His tag fused to CD80 respectively, and after excitation with 320 nm laser, energy can be transferred from Eu element to XL665 fluorescein due to the binding of PD-L1 and CD80 to excite the XL665 fluorescein to emit light. When an inhibitor for inhibiting interaction of PD-L1 and CD80 is added, the binding of PD-L1 and CD80 is destroyed, causing a long distance between Eu and XL665. As a result, the energy cannot be transferred, and the XL665 fluorescein will not be excited.

Experimental Materials and Devices

The recombinant human CD80 protein with His tag (His-CD80 protein, Cat #: 10698-H08H-100) and the recombinant human PD-L1-Fc fusion protein (PD-L1-Fc fusion protein, Cat #: 10084-H02H-100) were purchased from Sino Biological Inc., anti-hFc-Eu$^{3+}$ antibody and anti-His-XL665 antibody were purchased from Cisbio, and other related reagents such as a diluent buffer (Diluent buffer 5 (Cat #: 62DL5DDC) and a detection buffer (PPI-European detection buffer, Cat #: 61DB9RDF) were purchased from Cisbio. Fluorescence detector Tecan (Spark 10M) was purchased from Tecan Company in Switzerland.

Main Process of Experiment

The experiment process was carried out according to the flow required in the operating manual of the test reagent (Invitrogen). The process was as follows:

(1) Experiment preparation: A test compound was diluted to different concentration gradients with the dilution buffer (the highest final concentration in a 20 μL final reaction system was 10 μM). The His-CD80 protein was diluted to 800 nM (the final concentration in the 20 final reaction system was 100 nM). The PD-L1-Fc fusion protein was diluted to 16 nM (the final concentration was 2 nM). The anti-His-XL665 antibody and the anti-hFc-Eu$^{3+}$ antibody were diluted 20 times and 100 times respectively with the detection buffer according to reagent requirements.

(2) First, 5 μL of the test compound, 2.5 μL of the His-CD80 fusion protein and 2.5 μL of the PD-1-Fc fusion protein solution were well mixed and incubated at room temperature for 15 min; then, 5 μL of the anti-His-XL665 antibody and 5 μL of the anti-hFc-Eu$^{3+}$ antibody were added to the system and further incubated for 3 h before test.

(3) During the test reaction, control groups were set, including a 0% inhibitory positive control without adding the test compound and a 100% inhibitory negative control without adding the CD80 protein. All tests were conducted by use of multiple holes.

(4) The fluorescence detector Tecan (Spark 10M) was used to detect the fluorescence signal of each hole. The excitation wavelength was 320 nm, and the emission wavelengths for detection were 620 nm and 665 nm, respectively. The strength of CD80/PD-L1 binding refers to a fluorescence signal ratio Em665/Em620.

(5) Calculation formula of binding inhibition rate of test compound: Inhibition rate (%)=[1−(fluorescence signal ratio of detected hole−fluorescence signal ratio of 100% inhibition negative control)]/(fluorescence signal ratio of 0% inhibition positive control− fluorescence signal ratio of 100% inhibition negative control)× 100%. The 50% inhibition concentration (IC$_{50}$) was calculated after the CD80/PD-L1 binding inhibition rates of the test compound with different concentration gradients were calculated respectively. The IC$_{50}$ data of the representative compounds of this disclosure for inhibiting CD80/PD-L1 binding in vitro are shown in Table 3 below:

TABLE 3

IC$_{50}$ data of representative compounds of this disclosure for inhibiting CD80/PD-L1 binding in vitro

| Compound number | IC$_{50}$ (nM) | Compound number | IC$_{50}$ (nM) | Compound number | IC$_{50}$ (nM) |
| --- | --- | --- | --- | --- | --- |
| I-1 | 0.84 | I-2 | 0.79 | I-3 | 0.96 |
| I-4 | 2.78 | I-5 | 2.16 | I-6 | 0.86 |
| I-7 | 0.33 | I-8 | 3.40 | I-9 | 0.41 |
| I-10 | 0.62 | I-11 | 1.43 | I-12 | 1.64 |
| Example 180 | 5.53 | | | | |

It can be seen from the above results that the compounds of this disclosure have excellent activity of inhibiting CD80/PD-L1 binding in vitro, and the compounds of the general formula (I) of this disclosure also have activity of inhibiting CD80/PD-L1 binding. Compared with the control molecule (described in the aforementioned Example 180), the compounds of this disclosure have obviously excellent activity of inhibiting CD80/PD-L1 binding.

Example C Evaluation of Inhibition of T Cell Activation Signal Mediated by Immunocheckpoint PD-1 and PD-L1 at Cell Level As an immunocheckpoint molecule, PD-1 is mainly expressed on the surface of activated T cells, while its ligand PD-L1 is widely expressed. In addition to antigen presenting cells such as dendritic cells, macrophages, and B cells, many tumor cells can also inhibit anti-tumor immune effects by up-regulating the expression of PD-L1. For normal immune response, antigen presenting cells not only activate T cells through immuno-costimulatory molecules, but also express PD-L1 ligand molecules to bind to PD-1 molecules on the surface of activated T cells, thus inhibiting T cell activation and avoiding damage to surrounding normal tissues caused by excessive proliferation and activation of T cells.

Main Principle of Experiment

In order to test the effect of interaction between PD-1 and PD-L1 on T cell activation signal in immune response, CHO-PD-L1-CD3L cells stably expressing human PD-L1 molecule and anti-CD3 single-chain antibody (ScFv) and Jurkat-PD-1-NFAT cells stably expressing human PD-1 molecule and NFAT reporter gene were constructed. When two kinds of cells are incubated together, anti-CD3 ScFv on the CHO cell surface and membrane CD3 molecule of Jurkat cell combine to transmit an activation signal into Jurkat cell. However, due to the binding of PD-L1 on the CHO cell surface and PD-1 molecule on the Jurkat cell surface at the same time, a signal for inhibiting activation is transmitted inward, so that luciferase reporter gene cannot be expressed. When an immunocheckpoint antibody or small-molecule inhibitor is added, the binding of PD-1 and PD-L1 is blocked, the NFAT pathway activated by CD3 ScFv antibody and CD3 cross-linking mediated T cell activation signal is no longer affected by the inhibitory signal, and the downstream luciferase reporter gene starts to be expressed. Chemiluminescence signals proportional to reporter gene activation can be detected by adding a catalytic substrate.

Experimental Materials and Devices

CHO-PD-L1-CD3L cells expressing human PD-L1 molecule and anti-CD3 single-chain antibody (ScFv) and Jurkat-PD-1-NFAT cells stably expressing human PD-1 molecule and NFAT reporter gene were all independently constructed and presented by Dr. Chen Bo (KeyMed Biosciences (Chengdu) Co., Ltd. Puromycin (Cat #540411) and Hygromycin B (Cat #V900372) for stable culture of transfected cells were purchased from Sigma, PMA (Cat #P1585) was purchased from Sigma, and the anti human PD-L1 antibody (Cat #GMP-A066) was purchased from Novoprotein Company. The Luciferase substrate solution (Cat #E6485) and the luciferase-specific cell lysate 5×(Cat #E1531) were purchased from Promega company. The fluorescence detector Tecan (Spark 10M) was purchased from Tecan Company in Switzerland.

Main Process of Experiment (1) On the day before the experiment, 100 μL of CHO-PD-L1-CD3L cells (about 4×10$^4$ cells/well) were inoculated at 37° C. overnight in a 96-well cell culture plate, and the culture medium was DMEM/F12 containing 10% FBS, 8 μg/mL Puromycin and 200 μg/mL Hygromycin B.

(2) The test compound was diluted with 0.1% PBST to obtain solutions with different concentration gradients, and then added into 96-well plates and incubated for 30 min in advance. The RPMI 1640 complete medium containing 10% FBS, 8 μg/mL Puromycin and 200 μg/mL Hygromycin B was used to adjust the Jurkat-PD-1-NFAT cell count to 2×10$^5$ cells/mL, and 100 ng/mL PMA (10 mg/mL storage solution prepared with DMSO) was added to amplify the T cell activation signal. 100 μL of the Jurkat-PD-1-NFAT cells were added into each well of the 96-well plates for co-culture.

(3) During the test reaction, control groups were set, including the solvent control without adding the test compound and the positive control with the addition of the anti human PD-1 antibody in the experimental system. All tests were conducted by use of multiple holes.

(4) Incubation was continued at 37° C. for 6 h, 40 µL of 5× cell lysate was added directly, the solution was mixed well and placed at room temperature for 10 min to completely lyse cells. 50 µL of lysed cell solution was transferred to a fluorescence detection plate, 30 µL of luciferase substrate solution was then added, and the chemiluminescence detection program was immediately selected on the fluorescence detector for determination.

(5) Calculation formula of the inhibition rate of the test compound against T cell activation signal at the cell level: The inhibition rate against T cell activation signal (%)=(original chemiluminescence value of the test hole−solvent control)/(the highest original chemiluminescence value determined in the compound test hole−solvent control)×100%. The 50% inhibition concentration ($EC_{50}$) was calculated after the inhibition rate of the test compound with different concentration gradients against T cell activation signal were calculated respectively. The $EC_{50}$ data of the compounds of this disclosure for blocking PD-1/PD-L1 mediated inhibitory signal to T cell activation are shown in Table 4:

TABLE 4

$EC_{50}$ of the compounds of this disclosure for blocking PD-1/PD-L1 mediated inhibitory signal to T cell activation

| Compound number | $EC_{50}$ (nM) | Compound number | $EC_{50}$ (nM) | Compound number | $EC_{50}$ (nM) |
|---|---|---|---|---|---|
| I-1 | 33.9 | I-2 | 18.1 | I-3 | 17.0 |
| I-4 | 28.3 | I-5 | 26.7 | I-6 | 15.8 |

TABLE 4-continued $EC_{50}$ of the compounds of this disclosure for blocking PD-1/PD-L1 mediated inhibitory signal to T cell activation

| Compound number | $EC_{50}$ (nM) | Compound number | $EC_{50}$ (nM) | Compound number | $EC_{50}$ (nM) |
|---|---|---|---|---|---|
| I-7 | 39.2 | I-8 | 30.3 | I-9 | 6.79 |
| I-10 | 35.5 | I-11 | 26.3 | I-12 | 38.3 |
| Example 180 | 107.8 | | | | |

It can be seen from the above results that the compounds of this disclosure have the activity of effectively blocking the immunocheckpoint-mediated inhibitory signal to T cell activation at the cell level. Compared with the control molecule (i.e. the aforementioned Example 180), most compounds of the general formula (I) of this disclosure have higher activity of effectively blocking the immunocheckpoint-mediated inhibitory signal to T cell activation at the cell level.

Example D Single-Dosing Pharmacokinetics Test 24 6-week old B-hPD-1/hPD-L1 female mice (purchased from Biocytogen (Jiangsu) Gene Biotechnology Co., Ltd.) were taken and the test compound was dissolved in a solvent containing 5% DMSO, 60% PEG400 and 35% purified water. The compound I-6 and three control molecules, Example 17, Compound 14 (INCB086550) and Example 180 were dosed. The compound was administered by gavage in a single dose of 100 mg/kg and blood was collected through fundus vein plexus after administration. The time points for blood collection were 15 min, 30 min, 1 h, 2 h, 4 h, 8 h, 24 h, 32 h and 48 h. About 0.1 mL of blood was collected and centrifuged in a centrifuge tube (heparin sodium anticoagulation) at 5000 rpm for 5 min to separate plasma, and then frozen at −20° C. for testing. After the plasma sample was treated, the concentration of the compound in the plasma was determined by liquid chromatography-mass spectrometry (LC-MS/MS). The pharmacokinetic parameters were calculated using Phoenix WinNonlin 7.0 based on the average blood concentration data at different time points. The summary of data is shown in Table 5:

TABLE 5

Pharmacokinetic parameters of compounds in humanized mice in a single dose of 100 mg/kg

| Compound | $AUC_{(0-1)}$ (h*µg/mL) | $T_{1/2}$ (h) | MRT(h) |
|---|---|---|---|
| I-6 | 207.3 | 9.3 | 10.9 |
| [a]Example 17 | 118.1 | 3.8 | 4.2 |
| [b]Compound 14 (INCB086550) | 19.6 | 3.9 | 5.9 |
| Example 180 | 45.4 | 3.5 | 4.7 |

[a]Example 17 provides a compound disclosed by Incyte Company on page 64 of the text of the patent application WO2019/217821. The inventor synthesized the compound with reference to the synthesis method therein for use as a control molecule. The chemical structure of Example 17 was confirmed by LC-MS MS-ESI (m/z) 911.4 [M + H]⁺. Due to the poor solubility of Example 17, the nuclear magnetic resonance sample was added with sodium hydroxide solution for facilitating dissolution (the molar ratio of Example 17 to sodium hydroxide was 1:2), and then MeOD was added for structural confirmation. The chemical structure was confirmed by ¹H-NMR (400 MHz, MeOD) δ ppm 8.45 (dd, J = 8.3, 1.2 Hz, 2H), 7.43 (t, J = 8.0 Hz, 2H), 7.12-7.07 (m, 2H), 3.95 (d, J = 14.4 Hz, 6H), 3.55 (s, 4H), 2.96-2.84 (m, 4H), 2.72-2.82 (m, 4H), 2.70-2.62 (m, 4H), 2.00-1.88 (m, 4H), 1.87-1.78 (m, 4H), 1.66-1.37 (m, 16H). The structural formula of the compound is as follows:

TABLE 5-continued

Pharmacokinetic parameters of compounds in humanized mice in a single dose of 100 mg/kg

| Compound | AUC $_{(0-1)}$ (h*μg/mL) | T$_{1/2}$ (h) | MRT(h) |
|---|---|---|---|

Example 17

[b]Compound 14 (INCB086550) provides a compound disclosed by Incyte Company in Table 2 of patent application CN110267953A. The inventor synthesized the compound with reference to the synthesis method therein for use as a control molecule. Compound 14 (INCB086550) serves as a small-molecule PD-L1 inhibitor with the fastest clinical progress and is currently in Phase 2 Research.

The chemical structure of Compound 14 (INCB086550) was confirmed by LC-MS MS-ESI (m/z) 694.2 [M+H]$^+$ and $^1$H-NMR (400 MHz, DMSO) δ ppm 9.31 (s, 1H), 8.84 (s, 1H), 8.48 (d, J=8.0 Hz, 1H), 8.17 (s, 1H), 8.13 (d, J=7.7 Hz, 1H), 8.09-8.03 (m, 2H), 7.83 (s, 1H), 7.54 (t, J=7.7 Hz, 1H), 7.43 (d, J=7.4 Hz, 1H), 7.34 (t, J=7.9 Hz, 1H), 7.18 (d, J=5.8 Hz, 1H), 6.91 (d, J=7.4 Hz, 1H), 4.76 (s, 1H), 4.26-4.18 (m, 1H), 3.85-3.65 (m, 4H), 2.84-2.69 (m, 3H), 2.69-2.60 (m, 2H), 2.58-2.46 (m, 3H), 2.45 (s, 3H), 2.38 (dd, J=9.6, 3.6 Hz, 1H), 2.08 (s, 3H), 2.05-1.95 (m, 2H), 1.94-1.83 (m, 1H), 1.63-1.52 (m, 1H). The structural formula of the compound is as follows:

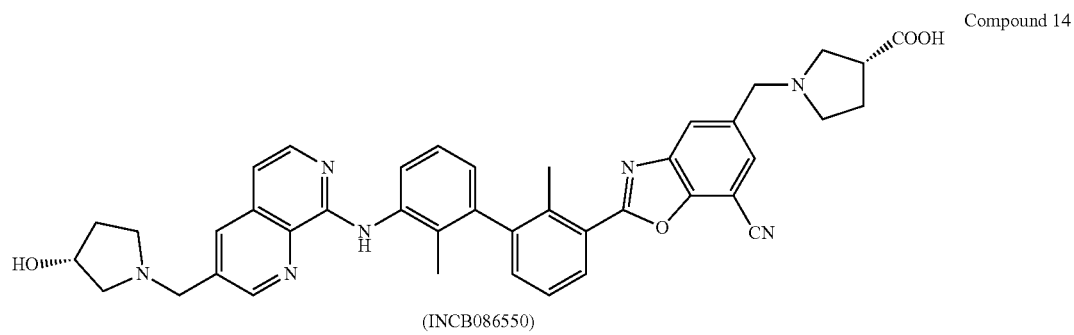 [SMILES: Cc1c(Nc2nccc3cc(CN4CC[C@@H](O)C4)cnc23)cccc1-c1cccc(-c2nc3cc(CN4CC[C@@H](C(=O)O)C4)cc(C#N)c3o2)c1C]

It can be seen from the above results that the in vivo plasma exposure (AUC$_{(0-t)}$, mean retention time (MRT) and half-life (T$_{1/2}$) of the representative compounds of this disclosure in mice after single oral dosing of 100 mg/kg were significantly higher than those of the three control molecules. Compared with the control molecules, the in vivo exposure amount and continuous exposure time of the compounds of this disclosure have an unexpected increase, which is helpful to better play the anti-tumor activity in clinical treatment and achieve better curative effect.

Example E Repeated-Dosing Pharmacokinetics Test 24 6-week old B-hPD-1/hPD-L1 humanized female mice (purchased from Biocytogen (Jiangsu) Gene Biotechnology Co., Ltd.) were taken and the test compound was dissolved in a solvent containing 5% DMSO, 60% PEG400 and 35% purified water. The compound I-6 and three control molecules, Example 17, Compound 14 (INCB086550) and the aforementioned Example 180 were dosed. The compound was administered by gavage once a day in a dose of 50 mg/kg for 12 consecutive days, and blood was alternately collected through fundus vein plexus on day 12 of administration. The time points for blood collection were 15 min, 30 min, 1 h, 2 h, 4 h, 8 h, 24 h, 32 h and 48 h. About 0.1 mL of blood was collected and centrifuged in a centrifuge tube (heparin sodium for anticoagulation) at 5000 rpm for 5 min to separate plasma, and then frozen at −20° C. for testing. The concentration of the compound in the plasma was determined by liquid chromatography-mass spectrometry (LC-MS/MS). The pharmacokinetic parameters were calculated using Phoenix WinNonlin 7.0 based on the average blood concentration data at different time points. The summary of data is shown in Table 6:

TABLE 6

Pharmacokinetic parameters of compounds in humanized mice after repeated dosing

| Compound | AUC$_{(0-t)}$ (h*μg/mL) | T$_{1/2}$ (h) | MRT(h) |
|---|---|---|---|
| I-6 | 151.3 | 9.4 | 12.0 |
| Example 17 | 58.8 | 3.9 | 4.6 |
| Compound 14 (INCB086550) | 10.6 | 3.7 | 5.0 |
| Example 180 | 27.8 | 3.3 | 4.2 |

It can be seen from the above results that the in vivo plasma exposure (AUC$_{(0-t)}$, mean retention time (MRT) and half-life (T$_{1/2}$) of the representative compounds of this disclosure after repeated dosing of 50 mg/kg were significantly higher than those of the three control molecules. Repeated dosing better reflects the pharmacokinetic characteristics under real clinical treatment conditions. Compared with the control molecules, the compounds of this disclosure significantly improved in vivo exposure and continuous exposure time under repeated dosing conditions, which is helpful to better play the anti-tumor activity in clinical treatment.

Figure 2:
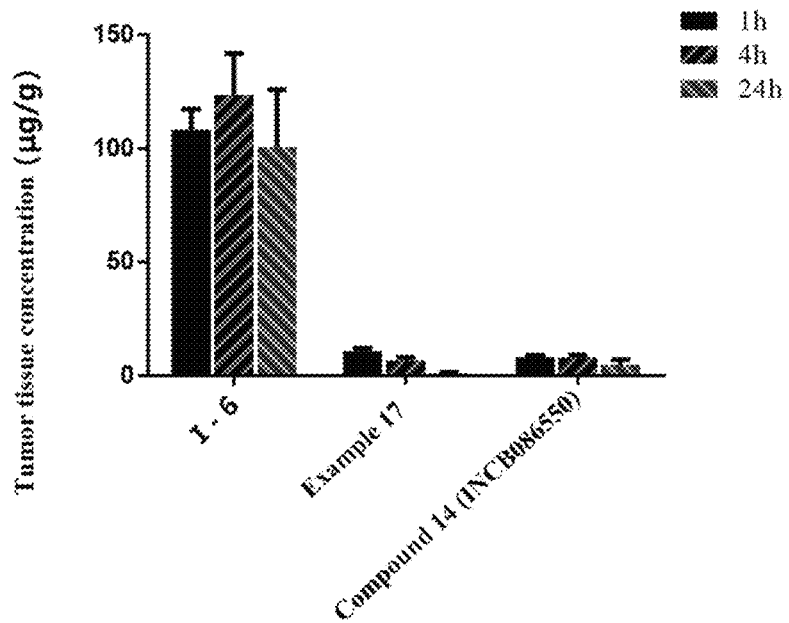
FIG. 2 shows tumor tissue distribution of example compound I-6 and control molecules.

Example F Tumor Tissue Distribution Test 18 6-week old B-hPD-1/hPD-L1 humanized female mice (purchased from Biocytogen (Jiangsu) Gene Biotechnology Co., Ltd.) were used for subcutaneous inoculation of MC$_{38}$-PD-L1 cells (2×10$^6$/site) after 1 week of adaptation, and then dosed in groups after the tumor grown to about 200 mm$^3$. The test compound was dissolved in a solvent containing 5% DMSO, 60% PEG400 and 35% purified water. The compound I-6 and the aforementioned two control molecules, Example 17 and Compound 14 (INCB086550) were dosed. The compound was administrated by gavage in a dose of 100 mg/kg once a day, and blood, tumor and other tissues were collected at time points of 1 h, 4 h and 24 h on day 16 of administration. A certain amount of tissue was weighed and homogenized with phosphate buffer salt (PBS) solution. The homogenized solution was then extracted and subjected to LC-MS/MS for analysis, and the concentration of the compound in the tissue was then calculated. The experimental results are shown in FIGS. 1 and 2.

It can be seen from the above results that after repeated dosing, the concentrations of the representative compounds of this disclosure in tumor tissues are significantly higher than those in plasma, and also significantly higher than those of the control molecules, showing excellent tumor tissue targeting. Compared with the control molecules, the compounds of this disclosure have unexpected enrichment and targeting effects on tumor tissues.

Figure 3:
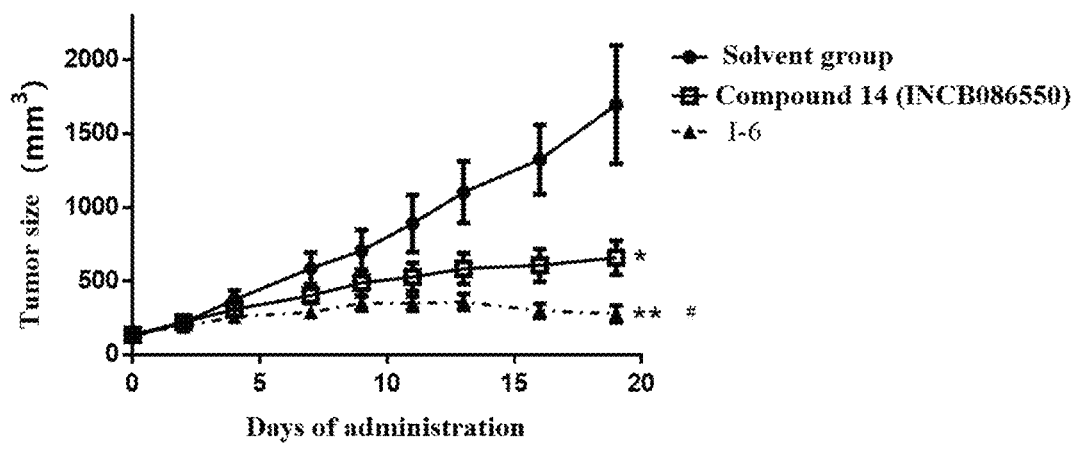
FIG. 3 shows tumor growth of example compound I-6 and control molecules.

Example G Pharmacodynamic Test on Transplanted Tumor in Mice 24 6-week old B-hPD-1/hPD-L1 humanized female mice (purchased from Biocytogen (Jiangsu) Gene Biotechnology Co., Ltd.) were used for subcutaneous inoculation of MC$_{38}$-PD-L1 cells (2×10$^6$/site) after 1 week of adaptation, and then randomly grouped and treated after the tumor grown to about 100 mm$^3$. The mice were divided into three groups: Solvent control group; the aforementioned Compound 14 (INCB086550) (100 mg/kg) group; Compound I-6 (100 mg/kg) group. The test compound was dissolved in a solvent containing 5% DMSO, 60% PEG400 and 35% purified water. The compound was administered by gavage once a day in a dose of 100 mg/kg for 19 consecutive days. Tumor size (length) was recorded twice a week (Length×Width$^2$× 0.5). The experimental results are shown in FIG. 3.

It can be seen from the above results that the representative compounds of this disclosure can significantly inhibit tumor growth on the humanized mouse MC$_{38}$-PD-L1 tumor model. Compared with the control molecules, the compounds of this disclosure have more significant efficacy on the humanized mouse tumor model.

For all compounds of this disclosure, including compounds of this disclosure and control molecules, the chemical structure formula shall prevail.

What is claimed is:

1. A compound or a stereoisomer thereof, or a pharmaceutically acceptable salt of the compound or the stereoisomer, wherein the compound is selected from group consisting of:

4-(2-(2-((2-chloro-3'-(5-(3-(4-(methoxymethyl)bicyclo[2.2.1]heptan-1-yl)propyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid,

109

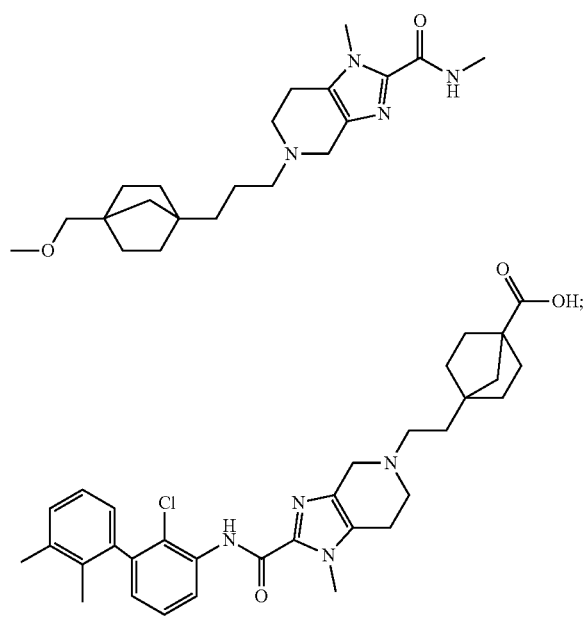

4-(2-(2-((2'-chloro-3'-(5-(2-(4-(ethoxymethyl)bicyclo
[2.2.1]heptan-1-yl)ethyl)-1-methyl-4,5,6,7-tetrahydro-
1H-imidazo[4,5-c]pyridine-2-carboxamido)-2-methyl-
[1,1'-biphenyl]-3-yl)carbamoyl)-1-methyl-1,4,6,7-
tetrahydro-5H-imidazo[4,5-c]pyridin-5-yl)ethyl)
bicyclo[2.2.1]heptane-1-carboxylic acid,

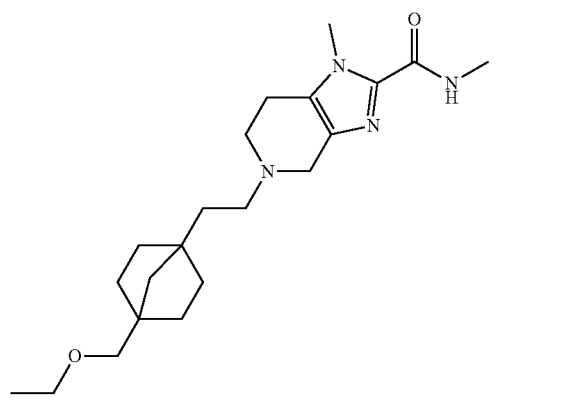

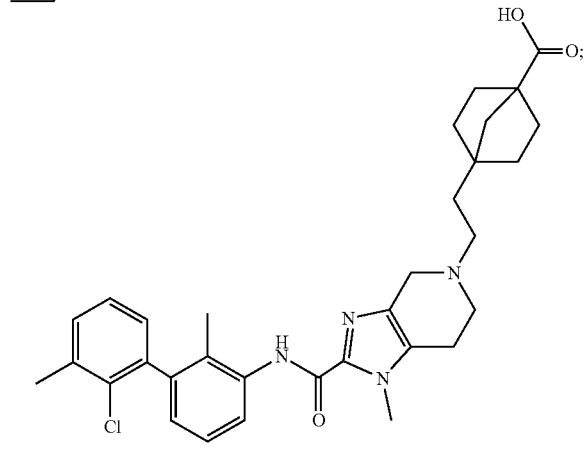

110

4-(2-(2-((2'-chloro-3'-(5-(2-(4-(methoxymethyl)bicyclo
[2.2.1]heptan-1-yl)ethyl)-1-methyl-4,5,6,7-tetrahydro-
1H-imidazo[4,5-c]pyridine-2-carboxamido)-2-methyl-
[1,1'-biphenyl]-3-yl)carbamoyl)-1-methyl-1,4,6,7-
tetrahydro-5H-imidazo[4,5-c]pyridin-5-yl)ethyl)
bicyclo[2.2.1]heptane-1-carboxylic acid,

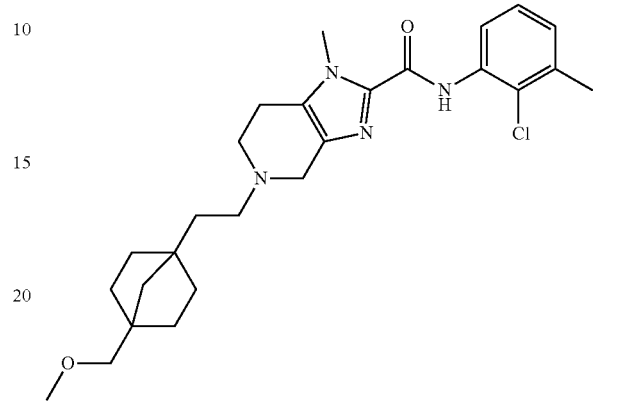

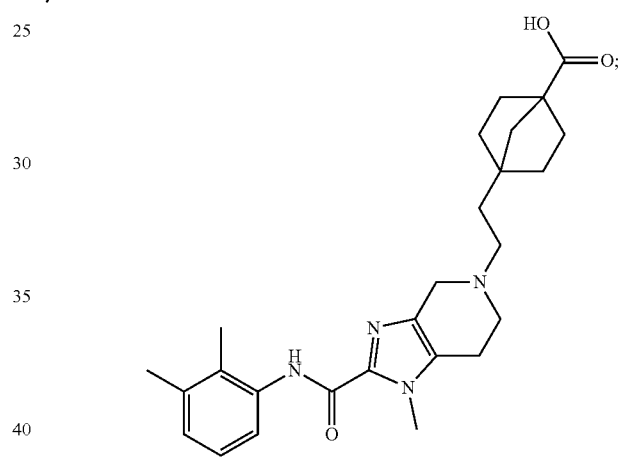

4-(2-(2-((2-chloro-3'-(5-(2-(4-(methoxymethyl)bicyclo
[2.2.1]heptan-1-yl)ethyl)-1-methyl-4,5,6,7-tetrahydro-
1H-imidazo[4,5-c]pyridine-2-carboxamido)-2'-methyl-
[1,1'-biphenyl]-3-yl)carbamoyl)-1-methyl-1,4,6,7-
tetrahydro-5H-imidazo[4,5-c]pyridin-5-yl)ethyl)
bicyclo[2.2.1]heptane-1-carboxylic acid,

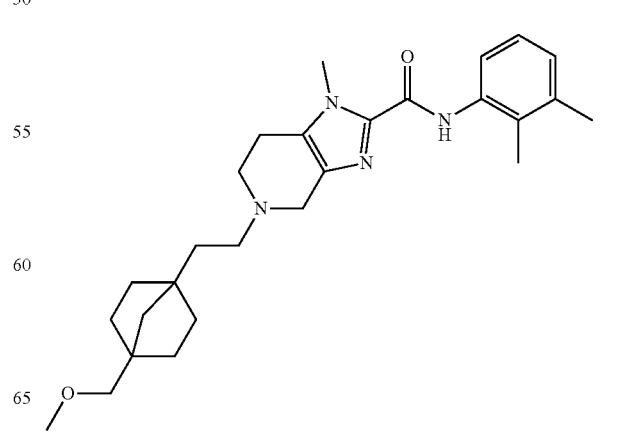

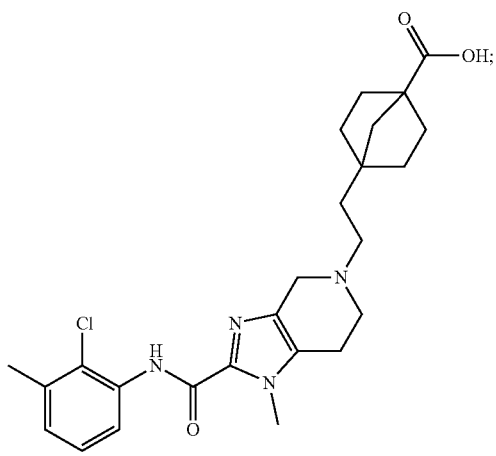

4-(2-(2-((2'-chloro-3'-(5-(3-(4-(methoxymethyl)bicyclo[2.2.1]heptan-1-yl)propyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid,

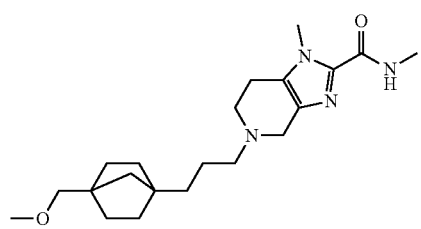

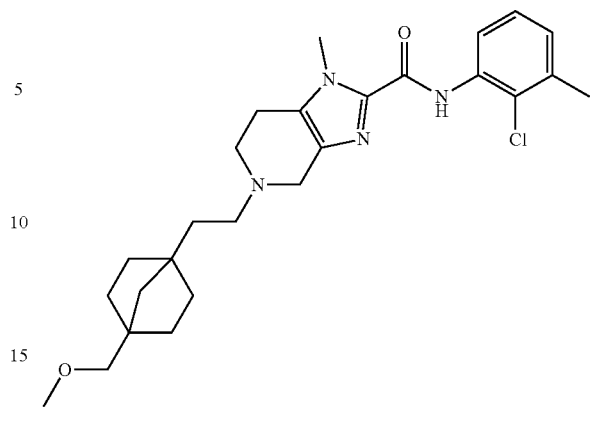

4-(2-(2-((2,2'-dichloro-3'-(5-(2-(4-(m ethoxymethyl)bicyclo[2.2.1]heptan-1-yl)ethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid, 4-(2-(2-((2,2'-dichloro-3'-(5-(2-(4-(((difluoromethoxy)methyl)bicyclo[2.2.1]heptan-1-yl)ethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid,

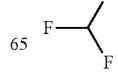

113

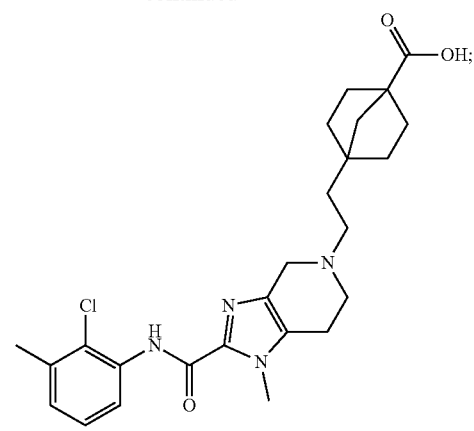

4-(2-(2-((2,2'-dichloro-3'-(5-((4-(methoxymethyl)bicyclo[2.2.1]heptan-1-yl)methyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid,

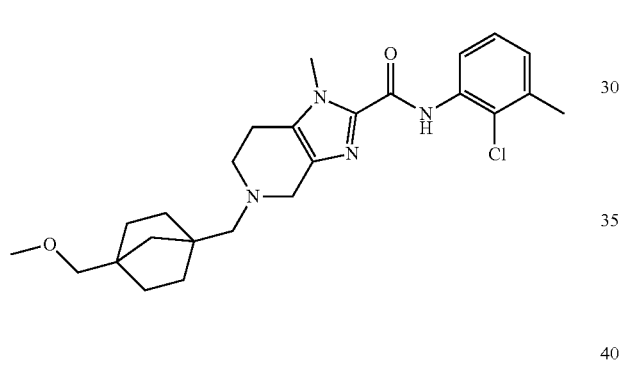

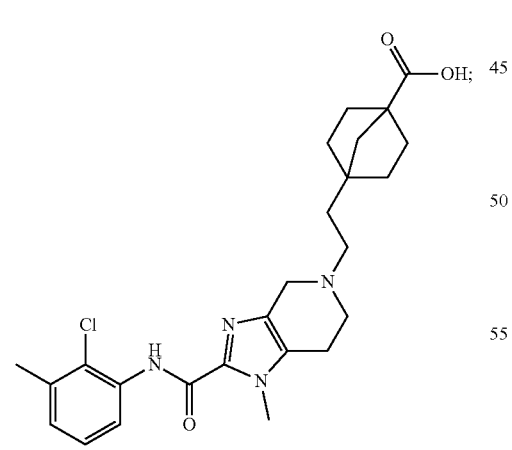

4-(2-(2-((2-chloro-2'-fluoro-3'-(5-(2-(4-(methoxymethyl)bicyclo[2.2.1]heptan-1-yl)ethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid,

114

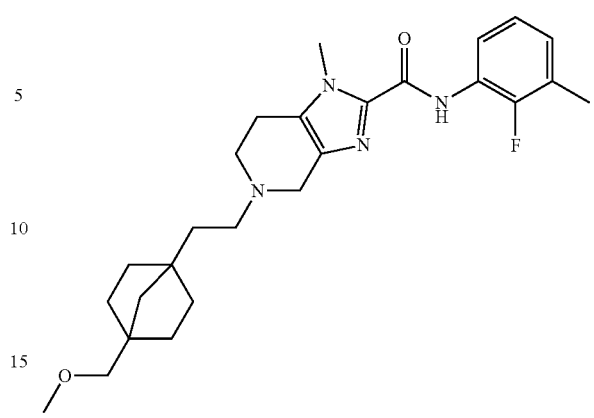

4-(2-(2-((2-chloro-3'-(5-(2-(4-((difluoromethoxy)methyl)bicyclo[2.2.1]heptan-1-yl)ethyl)-1-methyl-4,5,6,7-tetrahydro-1H-imidazo[4,5-c]pyridine-2-carboxamido)-2'-fluoro-[1,1'-biphenyl]-3-yl)carbamoyl)-1-methyl-1,4,6,7-tetrahydro-5H-imidazo[4,5-c]pyridin-5-yl)ethyl)bicyclo[2.2.1]heptane-1-carboxylic acid,

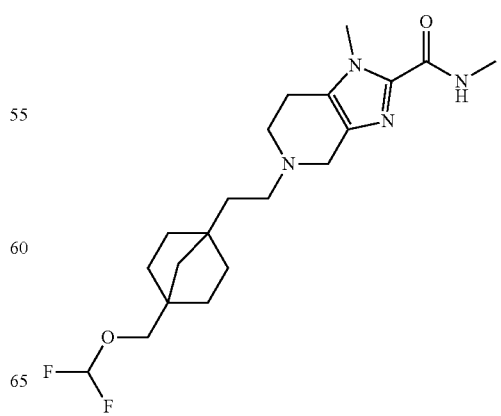

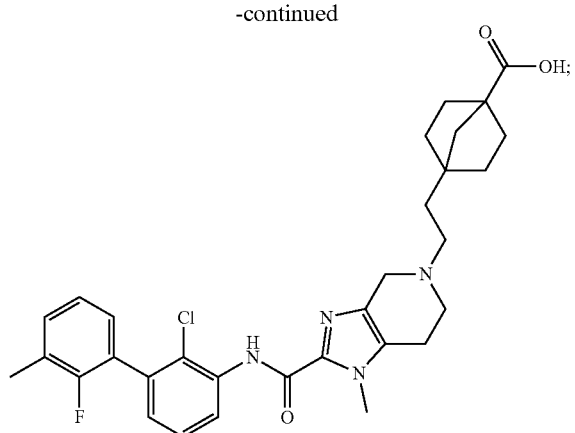

4-(2-(2-((2-chloro-2'-cyano-3'-(5-(2-(4-(methoxymethyl)
bicyclo[2.2.1]heptan-1-yl)ethyl)-1-methyl-4,5,6,7-tet-
rahydro-1H-imidazo[4,5-c]pyridine-2-carboxamido)-
[1,1'-biphenyl]-3-yl)carbamoyl)-1-methyl-1,4,6,7-
tetrahydro-5H-imidazo[4,5-c]pyridin-5-yl)ethyl)
bicyclo[2.2.1]heptane-1-carboxylic acid, and 4-((2-((2-chloro-3'-(5-(2-(4-(methoxymethyl)bicyclo
[2.2.1]heptan-1-yl)ethyl)-1-methyl-4,5,6,7-tetrahydro-
1H-imidazo[4,5-c]pyridine-2-carboxamido)-2'-methyl-
[1,1'-biphenyl]-3-yl)carbamoyl)-1-methyl-1,4,6,7-
tetrahydro-5H-imidazo[4,5-c]pyridin-5-yl)methyl)
bicyclo[2.2.1]heptane-1-carb oxylic acid,

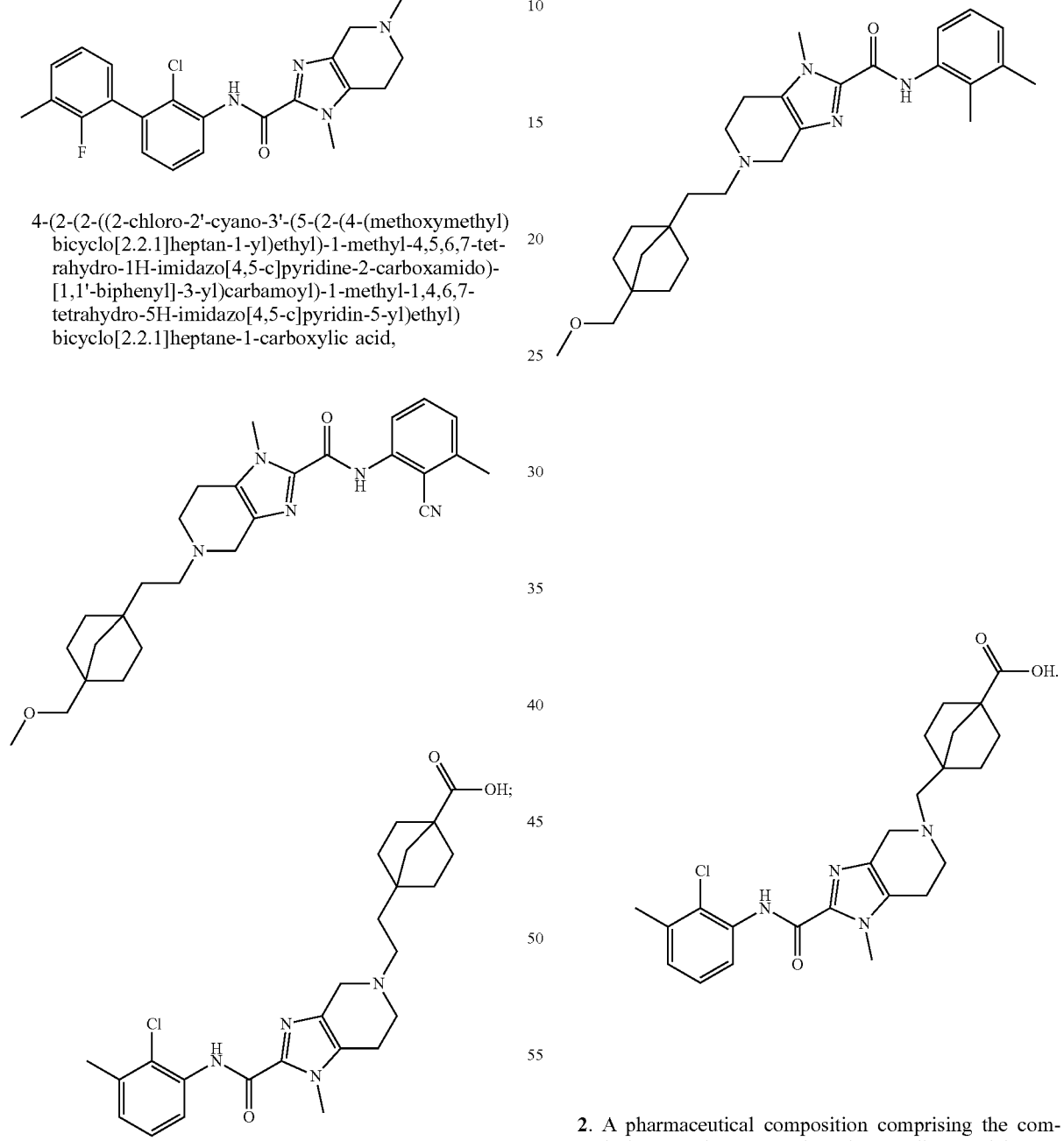

2. A pharmaceutical composition comprising the compound, the stereoisomer, or the salt according to claim 1.

* * * * *